(12) United States Patent
El-Deiry et al.

(10) Patent No.: US 11,203,598 B2
(45) Date of Patent: Dec. 21, 2021

(54) COMPOUNDS FOR REPRESSING CANCER CELL GROWTH

(71) Applicant: Institute For Cancer Research, Philadelphia, PA (US)

(72) Inventors: Wafik S. El-Deiry, Philadelphia, PA (US); Shengliang Zhang, Philadelphia, PA (US); Liz J. Hernandez Borrero, Philadelphia, PA (US)

(73) Assignee: Institute For Cancer Research, Philadelphia, PA (US)

( * ) Notice: Subject to any disclaimer, the term of this patent is extended or adjusted under 35 U.S.C. 154(b) by 0 days.

(21) Appl. No.: 16/255,204

(22) Filed: Jan. 23, 2019

(65) Prior Publication Data

US 2019/0225613 A1 Jul. 25, 2019

Related U.S. Application Data

(60) Provisional application No. 62/621,221, filed on Jan. 24, 2018, provisional application No. 62/711,142, filed on Jul. 27, 2018.

(51) Int. Cl.

| | |
|---|---|
| *C07D 473/08* | (2006.01) |
| *A61P 35/00* | (2006.01) |
| *A61K 45/06* | (2006.01) |
| *A61K 31/522* | (2006.01) |

(52) U.S. Cl.
CPC .......... *C07D 473/08* (2013.01); *A61K 31/522* (2013.01); *A61K 45/06* (2013.01); *A61P 35/00* (2018.01)

(58) Field of Classification Search
CPC ................................ C07D 473/08; A61P 35/00
See application file for complete search history.

(56) References Cited

PUBLICATIONS

Carlsson et al. J. Med. Chem. 2010, 53, 3748-3755 . (Year: 2010).*
Duffy et al. European Journal of Cancer 83 (2017) 258-265. (Year: 2017).*
Cancer Drug Design and Discovery, Neidle, Stephen,ed. (Elsevier/Academic Press), pp. 427-431. (Year: 2008).*
Zimmer et al. The Ohio Journal of Science. v63 No. 3 (May 1963), 97-102 (Year: 1963).*
Fang et al. Acta Pharmaceutica Sinica B 2020;10(7):1253e1278 .*
C. Richardson et al., "Small-molecule CB002 restores p53 pathway signaling and represses colorectal cancer cell growth", Cell Cycle, 2017, 16(18): 1719-1725.

* cited by examiner

*Primary Examiner* — Emily A Bernhardt
(74) *Attorney, Agent, or Firm* — Stradley Ronon Stevens & Young, LLP

(57) ABSTRACT

The disclosure generally relates to compounds, compositions, and methods for the treatment of cancer by restoring the P53 pathway signaling to repress cancer cell growth. In particular, the compounds comprise Formula I:

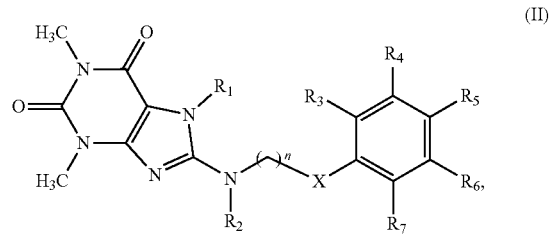

or a pharmaceutically acceptable salt thereof, wherein: $R_1$ is hydrogen or a haloalkyl group; and each $R_2$, $R_3$, $R_4$, $R_5$, $R_6$, and $R_7$ is, independently, hydrogen, halogen, hydroxyl, cyano, alkyl, alkenyl, alkoxy, substituted or unsubstituted aryl, heteroaryl, phosphate, phosphoramidate, amine, alkylamino, acylamino, aminoalkoxy, or alkylthio.

4 Claims, 42 Drawing Sheets

A

B

C

A

B

A

| CB002 (uM) | Ganetespib (nM) | Inhibitory Effect | Combination Index (CI) |
|---|---|---|---|
| 12.5 | 0.625 | 0.89 | 0.21086 |
| 12.5 | 1.25 | 0.87 | 0.21163 |
| 12.5 | 2.5 | 0.86 | 0.25625 |
| 12.5 | 5.0 | 0.83 | 0.29461 |
| 12.5 | 10.0 | 0.84 | 0.5204 |
| 12.5 | 20.0 | 0.77 | 0.54002 |
| 12.5 | 40.0 | 0.79 | 1.15133 |

B

| Analog #11 (uM) | Irinotecan (nM) | Inhibitory Effect | Combination Index (CI) |
|---|---|---|---|
| 25.0 | 1.56 | 0.86 | 0.44318 |
| 25.0 | 3.125 | 0.83 | 0.4849 |
| 25.0 | 6.25 | 0.75 | 0.45649 |
| 25.0 | 12.5 | 0.67 | 0.51057 |
| 25.0 | 25.0 | 0.61 | 0.6944 |
| 25.0 | 50.0 | 0.6 | 1.24133 |
| 25.0 | 100.0 | 0.53 | 1.77746 |

A

B

C

B

| Analog #4 (uM) | Bortezomib (nM) | Inhibitory Effect | Combination Index (CI) |
|---|---|---|---|
| 25.0 | 0.78 | 0.29 | 0.56354 |
| 25.0 | 1.56 | 0.28 | 0.59054 |
| 25.0 | 3.125 | 0.25 | 0.61458 |
| 25.0 | 6.25 | 0.17 | 0.57409 |
| 25.0 | 12.5 | 0.07 | 0.47641 |
| 25.0 | 25.0 | 0.02 | 0.41546 |
| 25.0 | 50.0 | 0.01 | 0.55471 |

C

COMPOUNDS FOR REPRESSING CANCER CELL GROWTH

STATEMENT OF GOVERNMENT SUPPORT

This invention was made with government support under Grant No. CN043302 awarded by the National Institutes of Health. The government has certain rights in the invention.

FIELD

The disclosure generally relates to compounds, compositions, and methods for the treatment of cancer by restoring the P53 pathway signaling to repress cancer cell growth. The disclosure provides novel P53 pathway restoring compounds, pharmaceutical compositions containing such compounds, and methods for using these compounds in the treatment of cancer.

BACKGROUND

Various publications, including patents, published applications, technical articles and scholarly articles are cited throughout the specification. Each of these cited publications is incorporated by reference herein, in its entirety and for all purposes.

The TP53 gene encodes the tumor suppressor protein p53, known as "the guardian of the genome," which ensures the fidelity of DNA replication and controls cell division, thereby preventing the formation and abnormal growth of cancerous cells. p53 becomes stimulated upon genotoxic and other cellular stress signals including DNA damage, loss of cell adhesion, spindle damage, oncogene activation, nutrient deprivation, ribonucleotide depletion, and hypoxia. Ultimately, such stresses lead to p53-mediated transcriptional activation of genes involved in DNA repair, cell cycle arrest, cellular senescence, and apoptosis. One of the most well studied outcomes of p53 has been apoptosis, owing to p53's irreversible capacity to induce programmed cell death. Among established p53 targets that participate in apoptosis are NOXA, PUMA, DR5, and Bax.

TP53 is mutated in more than 50% of all human cancers, and is one of the most explored cancer targets. TP53 mutation is a poor prognostic marker in various types of cancer. Unlike other tumor suppressors, missense mutations are the most common in TP53 and can result in the expression of a stable mutated p53 protein. TP53 mutations can result in loss of function (LOF), a dominant-negative phenotype, or gain of function (GOF) activity for the encoded mutant protein. Studies have shown in vitro and in vivo that introduction of certain types of p53 mutants in a p53-null background results in new phenotypes where tumor cells are more proliferative, invasive, resistant to therapy, or more metastatic.

In addition to mutant p53 acting in a dominant-negative fashion towards wild-type p53, mutant p53 has been shown to inhibit p53 family proteins p73 and p63. Consequently, p73 and p63 become incapable of exerting their tumor suppressive functions. p73 and p63 are transcription factors that share significant structural homology with p53. Similar to p53, p73 and p63 control the expression of genes involved in cell cycle arrest and apoptosis. It has been shown that p73 and p63 can functionally replace p53. Unlike p53, however, they are very rarely mutated in cancer. Therefore, restoration of the p53 pathway through its family members represents an attractive therapeutic approach.

Despite numerous efforts to identify small molecule compounds for mutant p53-targeted therapy, to date there is no approved drug that restores a functional p53 pathway in cancer cells with mutant p53. Given that TP53 is the most commonly mutated tumor suppressor, it is an attractive therapeutic strategy to identify such small molecules. With our current knowledge that p53 family members p73 and p63 can perform similar anti-tumor effects, our group and others have identified small molecules that restore the p53 pathway through the activation of p73. Using a luciferase-based p53-reporter, our group has previously identified several compounds that restore the p53 pathway including prodigiosin and NSC59984. These compounds have been reported to up-regulate p73 although the downstream mechanisms of action are believed to be different, and other regulatory activities of the molecules may be important. Furthermore, it is believed that mutant p53 protein degradation is necessary for optimal p73-mediated p53 pathway restoration. These findings support the pursuit of therapeutic strategies that target mutant p53 for degradation.

P53-targeted therapy is challenging because direct functional restoration of p53 activity as a DNA-binding transcription factor has been difficult to achieve using approaches whose goal is to modify p53 protein structure. Investigating small molecules that functionally restore the p53-signaling pathway instead of requiring direct p53 protein binding has begun. It is hypothesized that adequate p53 restoration in cancer cells carrying mutated p53 may involve the removal or inactivation of mutant p53 protein and activation of p53 family members p73 and p63. Accordingly, there is a need in the art for a compound or class of compounds that targets and restores the p53 pathway in p53-null, wild-type, or mutant p53-expressing cancer cells.

SUMMARY

The present disclosure provides compounds of Formula I:

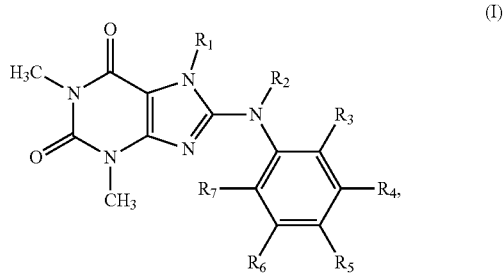

or a pharmaceutically acceptable salt thereof, wherein: $R_1$ is hydrogen or a substituted or unsubstituted haloalkyl group; and each $R_2$, $R_3$, $R_4$, $R_5$, $R_6$, and $R_7$ is, independently, hydrogen, halogen, hydroxyl, cyano, substituted or unsubstituted alkyl, substituted or unsubstituted alkenyl, substituted or unsubstituted alkoxy, substituted or unsubstituted aryl, substituted or unsubstituted heteroaryl, substituted or unsubstituted phosphate, substituted or unsubstituted phosphoramidate, substituted or unsubstituted amine, substituted or unsubstituted alkylamino, substituted or unsubstituted acylamino, substituted or unsubstituted aminoalkoxy, or substituted or unsubstituted alkylthio.

The present disclosure also provides pharmaceutical compositions comprising one or more of the compounds of Formula I and a pharmaceutically acceptable carrier.

The present disclosure also provides methods of treating a cancer in a mammal comprising administering to the mammal in need thereof a compound of Formula I.

The present disclosure also provides methods of restoring the tumor suppressor protein p53 signaling pathway within a tumor cell of a mammal comprising administering to the mammal in need thereof a compound of Formula I.

The present disclosure also provides compounds of Formula Ia:

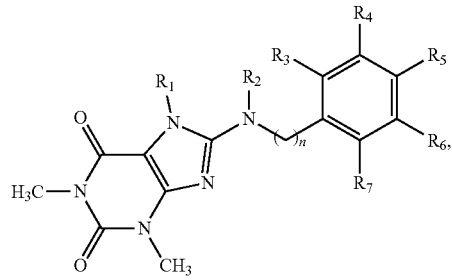

(Ia)

or a pharmaceutically acceptable salt thereof, wherein: $R_1$ is hydrogen or a substituted or unsubstituted alkyl; each $R_2$, $R_3$, $R_4$, $R_5$, $R_6$, and $R_7$ is, independently, hydrogen, halogen, hydroxyl, cyano, substituted or unsubstituted alkyl, substituted or unsubstituted alkenyl, substituted or unsubstituted haloalkyl, substituted or unsubstituted alkoxy, substituted or unsubstituted aryl, substituted or unsubstituted heteroaryl, substituted or unsubstituted phosphate, substituted or unsubstituted phosphoramidate, substituted or unsubstituted amine, substituted or unsubstituted alkylamino, substituted or unsubstituted acylamino, substituted or unsubstituted aminoalkoxy, or substituted or unsubstituted alkylthio; and n is an integer from 0 to 5. In some embodiments, the compound of Formula Ia is not

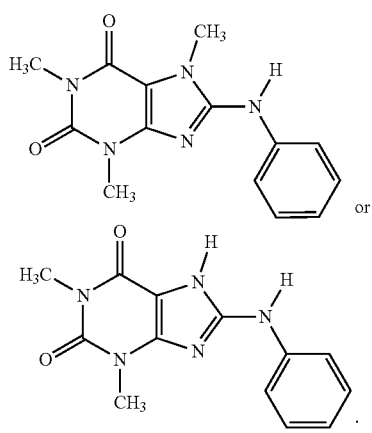

The present disclosure also provides pharmaceutical compositions comprising one or more of the compounds of Formula Ia and a pharmaceutically acceptable carrier.

The present disclosure also provides methods of treating a cancer in a mammal comprising administering to the mammal in need thereof a compound of Formula Ia.

The present disclosure also provides methods of restoring the tumor suppressor protein p53 signaling pathway within a tumor cell of a mammal comprising administering to the mammal in need thereof a compound of Formula Ia.

The present disclosure also provides compounds of Formula II:

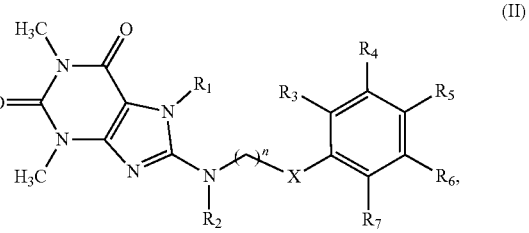

(II)

or a pharmaceutically acceptable salt thereof, wherein: $R_1$ is hydrogen or a substituted or unsubstituted alkyl group; each $R_2$, $R_3$, $R_4$, $R_5$, $R_6$, and $R_7$ is, independently, hydrogen, halogen, hydroxyl, substituted or unsubstituted alkyl, substituted or unsubstituted alkoxy, substituted or unsubstituted aryl, or substituted or unsubstituted amine; X is sulfur, oxygen, or —NH; and n is an integer from 0 to 5.

The present disclosure also provides pharmaceutical compositions comprising one or more of the compounds of Formula II and a pharmaceutically acceptable carrier.

The present disclosure also provides methods of treating a cancer in a mammal comprising administering to the mammal in need thereof a compound of Formula II.

The present disclosure also provides methods of restoring the tumor suppressor protein p53 signaling pathway within a tumor cell of a mammal comprising administering to the mammal in need thereof a compound of Formula II.

The present disclosure also provides compound of Formula III:

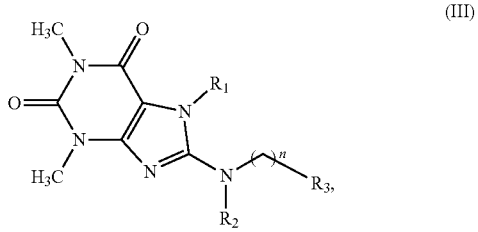

(III)

or a pharmaceutically acceptable salt thereof, wherein: $R_1$ and $R_2$ are, independently, hydrogen or a substituted or unsubstituted alkyl; $R_3$ is a substituted or unsubstituted heteroaryl; and n is an integer from 0 to 5.

The present disclosure also provides pharmaceutical compositions comprising one or more of the compounds of Formula III and a pharmaceutically acceptable carrier.

The present disclosure also provides methods of treating a cancer in a mammal comprising administering to the mammal in need thereof a compound of Formula III.

The present disclosure also provides methods of restoring the tumor suppressor protein p53 signaling pathway within a tumor cell of a mammal comprising administering to the mammal in need thereof a compound of Formula III.

DESCRIPTION OF EMBODIMENTS

Figure 1:
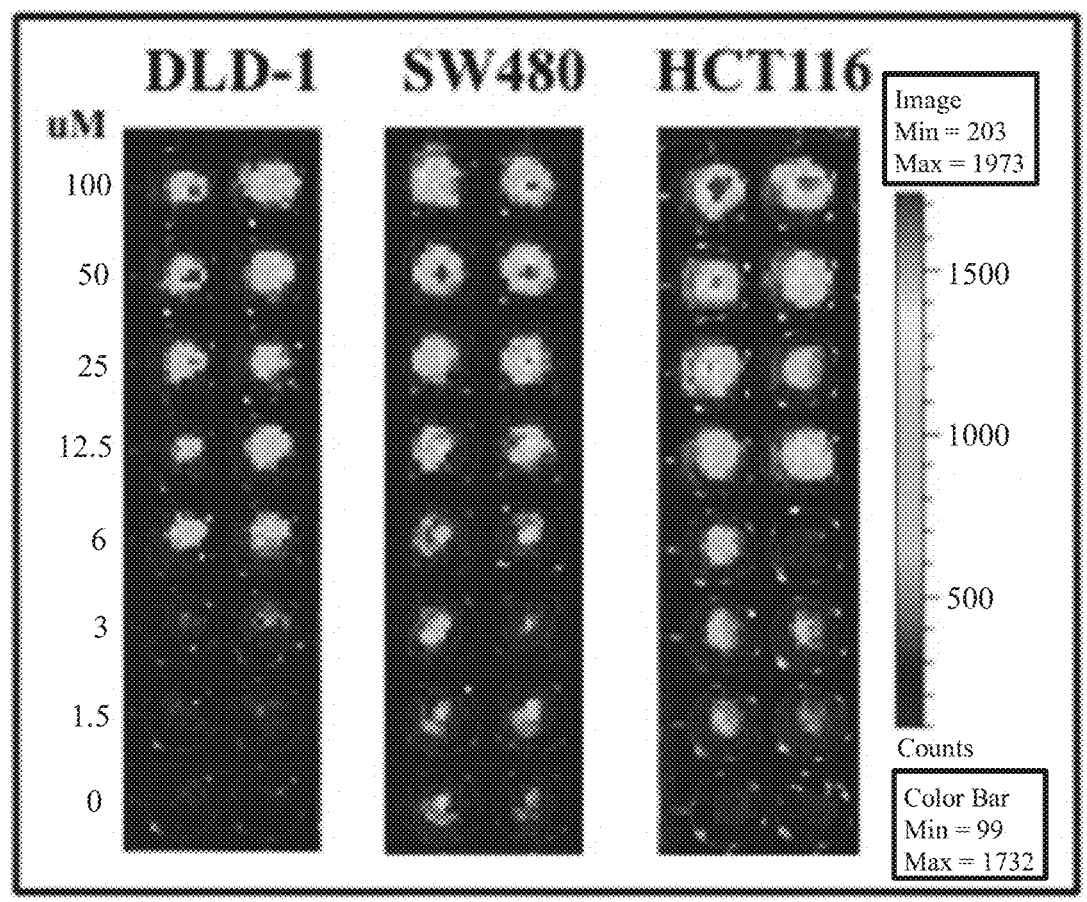
FIG. 1 (Panels A-E) shows CB002 activation of luciferase-based p53-reporter activity in three different human colorectal cancer cell lines in a dose-dependent manner.
Figure 1:
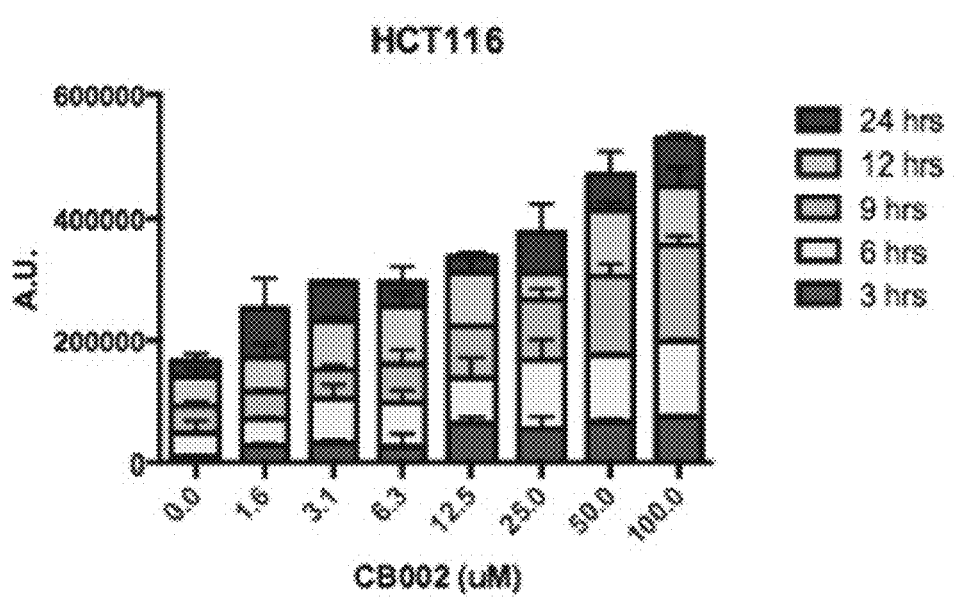
Figure 1:
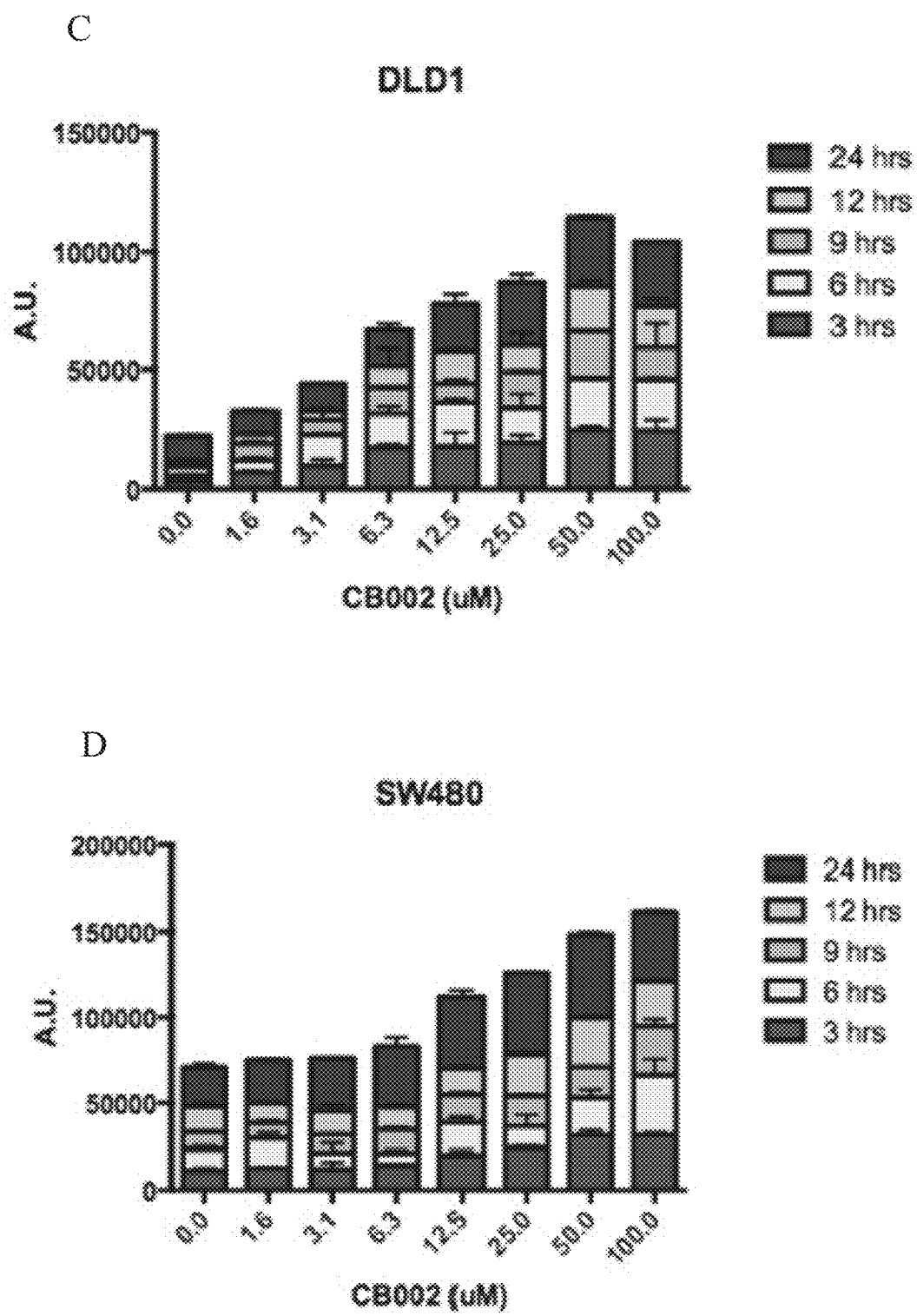
Figure 1:
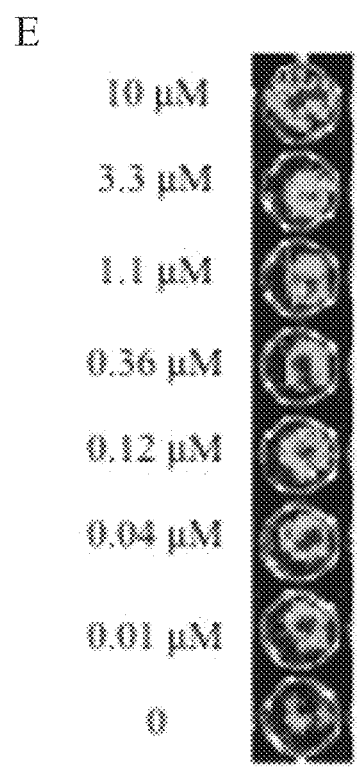

Various terms relating to aspects of the disclosure are used throughout the specification and claims. Such terms are to be given their ordinary meaning in the art, unless otherwise indicated. Other specifically defined terms are to be construed in a manner consistent with the definition provided herein. Unless defined otherwise, all technical and scientific terms have the same meaning as is commonly understood by one of ordinary skill in the art to which the disclosed embodiments belong.

As used herein, the terms "a" or "an" mean "at least one" or "one or more" unless the context clearly indicates otherwise.

As used herein, the term "about" means that the recited numerical value is approximate and small variations would not significantly affect the practice of the disclosed embodiments. Where a numerical value is used, unless indicated otherwise by the context, "about" means the numerical value can vary by ±10% and remain within the scope of the disclosed embodiments.

As used herein, the term "acylamino" means an amino group substituted by an acyl group. Examples of acylamino groups include, but are not limited to, —NHC(=O)H and —NHC(=O)CH$_3$. The phrase "lower acylamino" refers to an amino group substituted by a lower acyl group (e.g., —R—C(=O)—H or —R—C(=O)—C$_{1-6}$alkyl). Examples of lower acylamino groups include, but are not limited to, —NHC(=O)H, —NHC(=O)CH$_3$, —NHC(=O)CH$_2$CH$_3$, —NHC(=O)(CH$_2$)$_2$CH$_3$, —NHC(=O)(CH$_2$)$_3$CH$_3$, —NHC(=O)(CH$_2$)$_4$CH$_3$, and —NHC(=O)(CH$_2$)$_5$CH$_3$.

As used herein, the term "alkenyl" means a straight or branched alkyl group having 2 to 20 carbon atoms and having one or more double carbon-carbon bonds. In some embodiments, the alkenyl group has from 2 to 10 carbon atoms, from 2 to 8 carbon atoms, from 2 to 6 carbon atoms, from 2 to 4 carbon atoms, from 3 to 10 carbon atoms, from 3 to 8 carbon atoms, from 3 to 6 carbon atoms, or 3 or 4 carbon atoms. Examples of alkenyl groups include, but are not limited to, ethenyl, 1-propenyl, 2-methyl-1-propenyl, 2-propenyl, 1-butenyl, 2-butenyl, and the like.

As used herein, the term "alkoxy" means a straight or branched —O-alkyl group having 1 to 20 carbon atoms. In some embodiments, the alkoxy group has from 1 to 10 carbon atoms, from 1 to 8 carbon atoms, from 1 to 6 carbon atoms, from 1 to 4 carbon atoms, from 2 to 10 carbon atoms, from 2 to 8 carbon atoms, from 2 to 6 carbon atoms, or from 2 to 4 carbon atoms. Examples of alkoxy groups include, but are not limited to, methoxy, ethoxy, n-propoxy, isopropoxy, t-butoxy, and the like.

As used herein, the term "alkyl" means a saturated hydrocarbon group which is straight-chained or branched. In some embodiments, the alkyl group has from 1 to 20 carbon atoms, from 2 to 20 carbon atoms, from 1 to 10 carbon atoms, from 2 to 10 carbon atoms, from 1 to 8 carbon atoms, from 2 to 8 carbon atoms, from 1 to 6 carbon atoms, from 2 to 6 carbon atoms, from 1 to 4 carbon atoms, from 2 to 4 carbon atoms, from 1 to 3 carbon atoms, or 2 or 3 carbon atoms. Examples of alkyl groups include, but are not limited to, methyl (Me), ethyl (Et), propyl (e.g., n-propyl and isopropyl), butyl (e.g., n-butyl, t-butyl, isobutyl), pentyl (e.g., n-pentyl, isopentyl, neopentyl), hexyl, isohexyl, heptyl, octyl, nonyl, 4,4-dimethylpentyl, 2,2,4-trimethylpentyl, decyl, undecyl, dodecyl, 2-methyl-1-propyl, 2-methyl-2-propyl, 2-methyl-1-butyl, 3-methyl-1-butyl, 2-methyl-3-butyl, 2-methyl-1-pentyl, 2,2-dimethyl-1-propyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, and the like.

As used herein, the term "alkylamino" means an amino group substituted by an alkyl group. In some embodiments, the alkyl group is a lower alkyl group having from 1 to 6 carbon atoms. Alkylamino groups include, but are not limited to, —NHCH$_2$CH$_3$, —NH(CH$_2$)$_2$CH$_3$, —NH(CH$_2$)$_3$CH$_3$, —NH(CH$_2$)$_4$CH$_3$, and —NH(CH$_2$)$_5$CH$_3$, and the like.

As used herein, the term "alkylene" or "alkylenyl" means a divalent alkyl linking group. Example of alkylenes (or alkylenyls) include, but are not limited to, methylene or methylenyl (—CH$_2$—), ethylene or ethylenyl (—CH$_2$—CH$_2$—), and propylene or propylenyl (—CH$_2$—CH$_2$—CH$_2$—).

As used herein, the term "alkylthio" means an —S-alkyl group having from 1 to 6 carbon atoms. Alkylthio groups include, but are not limited to, —SCH$_2$CH$_3$, —S(CH$_2$)$_2$CH$_3$, —S(CH$_2$)$_3$CH$_3$, —S(CH$_2$)$_4$CH$_3$, and —S(CH$_2$)$_5$CH$_3$, and the like.

As used herein, the term "alkynyl" means a straight or branched alkyl group having 2 to 20 carbon atoms and one or more triple carbon-carbon bonds. In some embodiments, the alkynyl group has from 2 to 10 carbon atoms, from 2 to 8 carbon atoms, from 2 to 6 carbon atoms, or from 2 to 4 carbon atoms. Examples of alkynyl groups include, but are not limited to, acetylene, 1-propylene, 2-propylene, and the like.

As used herein, the term "amidino" means —C(=NH)NH$_2$.

As used herein, the term "amino" means —NH$_2$.

As used herein, the term "aminoalkoxy" means an alkoxy group substituted by an amino group. Examples of aminoalkoxy groups include, but are not limited to, —OCH$_2$NH$_2$, —OCH$_2$CH$_2$NH$_2$, —O(CH$_2$)$_3$NH$_2$, and —O(CH$_2$)$_4$NH$_2$, and the like.

As used herein, the term "aminoalkyl" means an alkyl group substituted by an amino group. Examples of aminoalkyl groups include, but are not limited to, —CH$_2$NH$_2$, —CH$_2$CH$_2$NH$_2$, —(CH$_2$)$_3$NH$_2$, —(CH$_2$)$_4$NH$_2$, and the like.

As used herein, the term "animal" includes, but is not limited to, mammals, humans and non-human vertebrates, such as wild, domestic, and farm animals.

As used herein, the terms "antagonize" and "antagonizing" mean reducing or completely eliminating one or more effects.

As used herein, the term "aryl" means a monocyclic, bicyclic, or polycyclic (e.g., having 2, 3 or 4 fused rings) aromatic hydrocarbon. In some embodiments, the aryl group has from 6 to 20 carbon atoms or from 6 to 10 carbon atoms. Examples of aryl groups include, but are not limited to, phenyl, naphthyl, anthracenyl, phenanthrenyl, indanyl, indenyl, and tetrahydronaphthyl, and the like.

As used herein, the term "arylalkyl" means an alkyl group substituted by an aryl. In some embodiments, the alkyl group is a C$_{1-6}$alkyl group.

As used herein, the term "arylamino" means an amino group substituted by an aryl group. Examples of arylamino groups include, but are not limited to, —NH(phenyl) and the like.

As used herein, the term "arylene" means an aryl linking group, i.e., an aryl group that links one group to another group in a molecule.

As used herein, the term "carrier" means a diluent, adjuvant, or excipient with which a compound is administered in a composition.

As used herein, the term, "compound" means all stereoisomers, tautomers, isotopes, and polymorphs of the compounds described herein.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive and open-ended and include the options following the terms, and do not exclude additional, unrecited elements or method steps.

As used herein, the term "contacting" means bringing together two compounds, molecules, or entities in an in vitro system or an in vivo system.

As used herein, the term "cyano" means —CN.

As used herein, the term "cycloalkyl" means non-aromatic cyclic hydrocarbons including cyclized alkyl, alkenyl, and alkynyl groups that have up to 20 ring-forming carbon atoms. Cycloalkyl groups have from 3 to 15 ring-forming carbon atoms, from 3 to 10 ring-forming carbon atoms, from 3 to 8 ring-forming carbon atoms, from 3 to 6 ring-forming carbon atoms, from 4 to 6 ring-forming carbon atoms, from 3 to 5 ring-forming carbon atoms, or 5 or 6 ring-forming carbon atoms. Ring-forming carbon atoms of a cycloalkyl group can be optionally substituted by oxo or sulfido. Cycloalkyl groups include, but are not limited to, monocyclic or polycyclic ring systems such as fused ring systems, bridged ring systems, and spiro ring systems. In some embodiments, polycyclic ring systems include 2, 3, or 4 fused rings. Examples of cycloalkyl groups include, but are not limited to, cyclopropyl, cyclobutyl, cyclopentyl, cyclohexyl, cycloheptyl, cyclooctyl, cyclononyl, cyclopentenyl, cyclohexenyl, cyclohexadienyl, cycloheptatrienyl, norbornyl, norpinyl, norcarnyl, adamantyl, and the like. Cycloalkyl groups can also have one or more aromatic rings fused (having a bond in common with) to the cycloalkyl ring such as, for example, benzo or thienyl derivatives of pentane, pentene, hexane, and the like (e.g., 2,3-dihydro-1H-indene-1-yl, or 1H-inden-2(3H)-one-1-yl).

As used herein, the term "halo" means halogen groups and includes, but is not limited to, fluoro, chloro, bromo, and iodo.

As used herein, the term "haloalkoxy" means an —O-haloalkyl group. Examples of haloalkoxy groups include, but are not limited to, —OCF$_3$ and —OCCl$_3$.

As used herein, the term "haloalkyl" means a C$_{1-6}$alkyl group having one or more halogen substituents. Examples of haloalkyl groups include, but are not limited to, —CF$_3$, —C$_2$F$_5$, —CHF$_2$, —CCl$_3$, —CHCl$_2$, —C$_2$Cl$_5$, —CH$_2$CF$_3$, and the like.

As used herein, the term "heteroaryl" means an aromatic heterocycle having up to 20 ring-forming atoms (e.g., C) and having at least one heteroatom ring member (ring-forming atom) such as sulfur, oxygen, or nitrogen. In some embodiments, the heteroaryl group has at least one or more heteroatom ring-forming atoms, each of which are, independently, sulfur, oxygen, or nitrogen. In some embodiments, the heteroaryl group has from 3 to 20 ring-forming atoms, from 3 to 10 ring-forming atoms, from 3 to 6 ring-forming atoms, or from 3 to 5 ring-forming atoms. In some embodiments, the heteroaryl group contains 2 to 14 carbon atoms, from 2 to 7 carbon atoms, or 5 or 6 carbon atoms. In some embodiments, the heteroaryl group has 1 to 4 heteroatoms, 1 to 3 heteroatoms, or 1 or 2 heteroatoms. Heteroaryl groups include monocyclic and polycyclic (e.g., having 2, 3 or 4 fused rings) systems. Examples of heteroaryl groups include, but are not limited to, pyridyl, pyrimidinyl, pyrazinyl, pyridazinyl, pyridinyl (including 2-aminopyridine), triazinyl, furyl, quinolyl, isoquinolyl, thienyl, imidazolyl, thiazolyl, indolyl (such as indol-3-yl), pyrryl, oxazolyl, benzofuryl, benzothienyl, pyrazolyl, benzthiazolyl, isoxazolyl, triazolyl (including 1,2,4-triazole, 1,2,3-triazole, and 5-amino-1,2,4-triazole), tetrazolyl, indazolyl, isothiazolyl, 1,2,4-thiadiazolyl, benzothienyl, purinyl, carbazolyl, isoxazolyl, benzimidazolyl, indolinyl, pyranyl, pyrazolyl, triazolyl, oxadiazolyl (including 1,2,3-oxadiazole, 1,2,4-oxadiazole, 1,2,5-oxadiazole, 3-amino-1,2,4-oxadiazole, 1,3,4-oxadiazole), thianthrenyl, indolizinyl, isoindolyl, isobenzofuranyl, pyrrolyl, benzoxazolyl, xanthenyl, 2H-pyrrolyl, 3H-indolyl, 4H-quinolizinyl, phthalazinyl, acridinyl, naphthyridinyl, quinazolinyl, phenanthridinyl, perimidinyl, phenanthrolinyl, phenazinyl, isothiazolyl, phenothiazinyl, isoxazolyl, furazanyl, phenoxazinyl groups, and the like.

As used herein, the term "heteroarylalkyl" means a $C_{1-6}$alkyl group substituted by a heteroaryl group.

As used herein, the term "heteroarylamino" means an amino group substituted by a heteroaryl group.

As used herein, the term "heteroarylene" means a heteroaryl linking group, i.e., a heteroaryl group that links one group to another group in a molecule.

As used herein, the term "heterocycle" or "heterocyclic ring" means a 5- to 7-membered monocyclic or 7- to 10-membered bicyclic ring system, any ring of which may be saturated or unsaturated, and which ring consists of carbon atoms and from one to three heteroatoms chosen from N, O and S, and wherein the N and S heteroatoms may optionally be oxidized, and the N heteroatom may optionally be quaternized, and including any bicyclic group in which any of the above-defined heterocyclic rings is fused to a benzene ring. Heterocycles include rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of heterocyclic groups include, but are not limited to, piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, pyridyl, imidazolidinyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, oxadiazolyl, and the like.

As used herein, the term "heterocycloalkyl" means nonaromatic heterocycles having up to 20 ring-forming atoms including cyclized alkyl, alkenyl, and alkynyl groups, where one or more of the ring-forming carbon atoms is replaced by a heteroatom, such as an O, N, or S atom. Hetercycloalkyl groups can be monocyclic or polycyclic (e.g., fused, bridged, or spiro systems). In some embodiments, the heterocycloalkyl group has from 1 to 20 carbon atoms or from 3 to 20 carbon atoms. In some embodiments, the heterocycloalkyl group contains 3 to 14 ring-forming atoms, 3 to 7 ring-forming atoms, or 5 or 6 ring-forming atoms. In some embodiments, the heterocycloalkyl group has 1 to 4 heteroatoms, 1 to 3 heteroatoms, or 1 or 2 heteroatoms. In some embodiments, the heterocycloalkyl group has 0 to 3 double bonds. In some embodiments, the heterocycloalkyl group has 0 to 2 triple bonds. Examples of heterocycloalkyl groups include, but are not limited to, morpholino, piperazinyl, thiomorpholino, tetrahydrofuranyl, tetrahydrothienyl, 2,3-dihydrobenzofuryl, piperidinyl, 1,3-benzodioxole, benzo-1,4-dioxane, pyrrolidinyl, isoxazolidinyl, oxazolidinyl, isothiazolidinyl, pyrazolidinyl, thiazolidinyl, imidazolidinyl, pyrrolidin-2-one-3-yl, and the like. In addition, ring-forming carbon atoms and heteroatoms of a heterocycloalkyl group can be optionally substituted by oxo or sulfido. For example, a ring-forming S atom can be substituted by 1 or 2 oxo (form a S(O) or S(O)$_2$). For another example, a ring-forming C atom can be substituted by oxo (form carbonyl). Heterocycloalkyl groups can also have one or more aromatic rings fused (having a bond in common with) to the nonaromatic heterocyclic ring including, but not limited to, pyridinyl, thiophenyl, phthalimidyl, naphthalimidyl, and benzo derivatives of heterocycles such as, for example, indolene, isoindolene, 5,6-dihydrothieno[2,3-c]pyridin-7(4H)-one-5-yl, isoindolin-1-one-3-yl, 4,5,6,7-tetrahydrothieno[2,3-c]pyridine-5-yl, and 3,4-dihydroisoquinolin-1(2H)-one-3yl groups. Ring-forming carbon atoms and heteroatoms of the heterocycloalkyl group can be optionally substituted by oxo or sulfido.

As used herein, the term "hydroxy" or "hydroxyl" means an —OH group.

As used herein, the term "hydroxyalkyl" or "hydroxylalkyl" means an alkyl group substituted by a hydroxyl group. Examples of hydroxylalkyl groups include, but are not limited to, —CH$_2$OH and —CH$_2$CH$_2$OH.

As used herein, the terms "individual," "subject," and "patient," used interchangeably, mean any animal described herein.

As used herein, the phrase "in need thereof" means that the "individual," "subject," or "patient" has been identified as having a need for the particular method, prevention, or treatment. In some embodiments, the identification can be by any means of diagnosis. In any of the methods, preventions, and treatments described herein, the "individual," "subject," or "patient" can be in need thereof. In some embodiments, the "individual," "subject," or "patient" is in an environment or will be traveling to an environment, or has traveled to an environment in which a particular disease, disorder, or condition is prevelant.

As used herein, the term "integer" means a numerical value that is a whole number. For example, an "integer from 1 to 5" means 1, 2, 3, 4, or 5.

As used herein, the term "isolated" means that the compounds, or pharmaceutically acceptable salts thereof, described herein are separated from other components of either: a) a natural source, such as a plant or cell, such as a bacterial culture, or b) a synthetic organic chemical reaction mixture, such as by conventional techniques.

As used herein, the term "mammal" means a rodent (i.e., a mouse, a rat, or a guinea pig), a monkey, a sheep, a cat, a dog, a cow, a horse, a pig, or a human. In some embodiments, the mammal is a human.

As used herein, the term "nitro" means —NO$_2$.

As used herein, the term "n-membered", where n is an integer, typically describes the number of ring-forming atoms in a moiety, where the number of ring-forming atoms is n. For example, pyridine is an example of a 6-membered heteroaryl ring and thiophene is an example of a 5-membered heteroaryl ring.

As used herein, the phrase "optionally substituted" means that a substitution is optional and, therefore, includes both unsubstituted and substituted atoms and moieties. A "substituted" atom or moiety indicates that any hydrogen atom on the designated compound or moiety can be replaced with a selection from the indicated substituent groups, provided that the normal valency of the designated compound or moiety is not exceeded, and that the substitution results in a stable compound. For example, if a methyl group is optionally substituted, then 1, 2, or 3 hydrogen atoms on the carbon atom within the methyl group can be replaced with 1, 2, or 3 of the recited substituent groups.

As used herein, the phrase "pharmaceutically acceptable" means that the compounds, materials, compositions, and/or dosage forms are within the scope of sound medical judgment and are suitable for use in contact with tissues of humans and other animals. In some embodiments, "pharmaceutically acceptable" means approved by a regulatory agency of the Federal government or a state government or listed in the U.S. Pharmacopeia or other generally recognized pharmacopeia for use in animals, and more particularly in humans. In some embodiments, the pharmaceutically acceptable compounds, materials, compositions, and/or dosage forms result in no persistent detrimental effect on the subject, or on the general health of the subject being treated. However, it will be recognized that transient effects, such as minor irritation or a "stinging" sensation, are common with administration of medicament and the existence of such transient effects is not inconsistent with the composition, formulation, or ingredient (e.g., excipient) in question.

As used herein, the phrase "pharmaceutically acceptable salt(s)," includes, but is not limited to, salts of acidic or basic groups. Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, thiosulfuric, citric, maleic, acetic, oxalic, hydrochloride, hydrobromide, hydroiodide, nitrate, sulfate, bisulfate, bisulfite, phosphate, acid phosphate, isonicotinate, borate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, bicarbonate, malonate, mesylate, esylate, napsydisylate, tosylate, besylate, orthophosphate, trifluoroacetate, and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, ammonium, sodium, lithium, zinc, potassium, and iron salts. Salts also includes quaternary ammonium salts of the compounds described herein, where the compounds have one or more tertiary amine moiety.

As used herein, the term "phenyl" means —$C_6H_5$. A phenyl group can be unsubstituted or substituted with one, two, or three suitable substituents.

As used herein, the terms "prevention" or "preventing" mean a reduction of the risk of acquiring a particular disease, condition, or disorder.

As used herein, the term "prodrug" means a derivative of a known direct acting drug, which derivative may have enhanced delivery characteristics and therapeutic value as compared to the active drug, and is transformed into the active drug by an enzymatic or chemical process.

As used herein, the term "purified" means that when isolated, the isolate contains at least 90%, at least 95%, at least 98%, at least 99%, or 100% of a compound described herein by weight of the isolate.

As used herein, the phrase "quaternary ammonium salts" means derivatives of the disclosed compounds with one or more tertiary amine moieties wherein at least one of the tertiary amine moieties in the parent compound is modified by converting the tertiary amine moiety to a quaternary ammonium cation via alkylation (and the cations are balanced by anions such as $Cl^-$, $CH_3COO^-$, and $CF_3COO^-$), for example methylation or ethylation.

As used herein, the phrase "solubilizing agent" means agents that result in formation of a micellar solution or a true solution of the drug.

As used herein, the term "solution/suspension" means a liquid composition wherein a first portion of the active agent is present in solution and a second portion of the active agent is present in particulate form, in suspension in a liquid matrix.

As used herein, the phrase "substantially isolated" means a compound that is at least partially or substantially separated from the environment in which it is formed or detected.

As used herein, the phrase "suitable substituent" or "substituent" means a group that does not nullify the synthetic or pharmaceutical utility of the compounds described herein or the intermediates useful for preparing them. Examples of suitable substituents include, but are not limited to: $C_1$-$C_6$alkyl, $C_1$-$C_6$alkenyl, $C_1$-$C_6$alkynyl, $C_5$-$C_6$aryl, $C_1$-$C_6$alkoxy, $C_3$-$C_5$heteroaryl, $C_3$-$C_6$cycloalkyl, $C_5$-$C_6$aryloxy, —CN, —OH, oxo, halo, haloalkyl, —$NO_2$, —$CO_2H$, —$NH_2$, —NH($C_1$-$C_8$alkyl), —N($C_1$-$C_8$alkyl)$_2$, —NH($C_6$aryl), —N($C_5$-$C_6$aryl)$_2$, —CHO, —CO($C_1$-$C_6$alkyl), —CO(($C_5$-$C_6$)aryl), —$CO_2$(($C_1$-$C_6$)alkyl), and —$CO_2$(($C_5$-$C_6$)aryl). One of skill in art can readily choose a suitable substituent based on the stability and pharmacological and synthetic activity of the compounds described herein.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor, or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be based on, for example, the age, health, size, and sex of the subject. Optimal amounts can also be determined based on monitoring of the subject's response to treatment.

As used herein, the terms "treat," "treated," or "treating" mean both therapeutic treatment and prophylactic or preventative measures wherein the object is to prevent or slow down (lessen) an undesired physiological condition, disorder or disease, or obtain beneficial or desired clinical results. For purposes herein, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response, optionally without excessive levels of side effects. Treatment also includes prolonging survival as compared to expected survival if not receiving treatment.

At various places herein, substituents of compounds may be disclosed in groups or in ranges. It is specifically intended that the disclosure include each and every individual sub-combination of the members of such groups and ranges. For example, the term "$C_{1-6}$alkyl" is specifically intended to individually disclose methyl, ethyl, propyl, $C_4$alkyl, $C_5$alkyl, and $C_6$alkyl.

For compounds in which a variable appears more than once, each variable can be a different moiety chosen from the Markush group providing options for the variable. For example, where a structure is described having two R groups that are simultaneously present on the same compound, the two R groups can represent different moieties chosen from the Markush group defined for R. In another example, when an optionally multiple substituent "R" is designated in the form, for example,

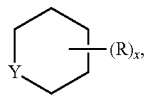

then it should be understood that substituent "R" can occur "x" number of times on the ring at any position(s), and "R" can be a different moiety at each occurrence. Further, in the above example, where the variable "Y" normally would include one or more hydrogens, such as when "Y" is $CH_2$, NH, etc., any H can be replaced with a substituent.

It should be appreciated that particular features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

It should be understood that stereoisomers (including diastereomers and enantiomers) of the compounds described herein, as well as mixtures thereof, are within the scope of the present disclosure. By way of non-limiting example, the mixture may be a racemate or the mixture may comprise unequal proportions of one particular stereoisomer over the other. Additionally, the compounds can be provided as a substantially pure stereoisomers. Diastereomers include, for example, cis-trans isomers, E-Z isomers, conformers, and rotamers. Methods of preparation of stereoisomers are known in the art, such as by resolution of racemic mixtures or by stereoselective synthesis. Many geometric isomers of olefins, C=N double bonds, and the like can also be present in the compounds described herein, and all such stable isomers are contemplated in the present disclosure. Cis and trans geometric isomers of the compounds are also included within the scope of the disclosure and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art, including, for example, fractional recrystallizaion using a chiral resolving acid which is an optically active, salt-forming organic acid. Suitable resolving agents for fractional recrystallization methods include, but are not limited to, optically active acids, such as the D and L forms of tartaric acid, diacetyltartaric acid, dibenzoyltartaric acid, mandelic acid, malic acid, lactic acid, and the various optically active camphorsulfonic acids such as β-camphor-sulfonic acid. Other resolving agents suitable for fractional crystallization methods include, but are not limited to, stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent compositions can be determined by one skilled in the art.

Appropriate compounds described herein may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two or more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

The compounds described herein also include hydrates and solvates, as well as anhydrous and non-solvated forms.

The compounds described herein can also include all isotopes of atoms occurring in the intermediates or final compounds. Isotopes include those atoms having the same atomic number but different mass numbers. For example, isotopes of hydrogen include tritium and deuterium. Carbon ($^{12}$C) can be replaced at any position with $^{13}$C or $^{14}$C. Nitrogen ($^{14}$N) can be replaced with $^{15}$N. Oxygen ($^{16}$O) can be replaced at any position with $^{17}$O or $^{18}$O. Sulfur ($^{32}$S) can be replaced with $^{33}$S, $^{34}$S or $^{36}$S. Chlorine ($^{35}$Cl) can be replaced with $^{37}$Cl. Bromine ($^{79}$Br) can be replaced with $^{81}$Br.

In some embodiments, the compounds, or salts thereof, are substantially isolated. Partial separation can include, for example, a composition enriched in any one or more of the compounds described herein. Substantial separation can include compositions containing at least about 50%, at least about 60%, at least about 70%, at least about 80%, at least about 90%, at least about 95%, at least about 97%, or at least about 99% by weight of any one or more of the compounds described herein, or salt thereof. Methods for isolating compounds and their salts are routine in the art.

The compounds described herein also include derivatives referred to as prodrugs, which can be prepared by modifying functional groups present in the compounds in such a way that the modifications are cleaved, either in routine manipulation or in vivo, to the parent compounds. Examples of prodrugs include compounds as described herein that contain one or more molecular moieties appended to a hydroxyl, amino, sulfhydryl, or carboxyl group of the compound, and that when administered to a patient, cleaves in vivo to form the free hydroxyl, amino, sulfhydryl, or carboxyl group, respectively. Examples of prodrugs include, but are not limited to, acetate, formate and benzoate derivatives of alcohol and amine functional groups in the compounds described herein. Preparation and use of prodrugs is discussed in T. Higuchi et al., "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference in their entireties.

Compounds containing an amine function can also form N-oxides. A reference herein to a compound that contains an amine function also includes the N-oxide. Where a compound contains several amine functions, one or more than one nitrogen atom can be oxidized to form an N-oxide. Examples of N-oxides include N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g., a peroxycarboxylic acid) (see, Advanced Organic Chemistry, by Jerry March, 4th Edition, Wiley Interscience).

The present disclosure provides compounds of Formula I:

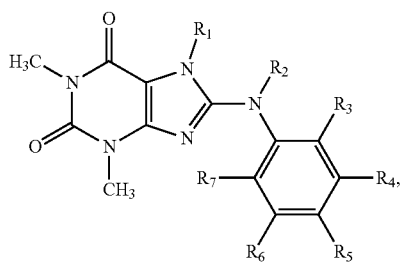

or a pharmaceutically acceptable salt thereof, wherein:
$R_1$ is hydrogen or a substituted or unsubstituted haloalkyl group; and
each of $R_2$, $R_3$, $R_4$, $R_5$, $R_6$, and $R_7$ is, independently, hydrogen, halogen, hydroxyl, cyano, substituted or unsubstituted alkyl, substituted or unsubstituted alkenyl, substituted or unsubstituted alkoxy, substituted or unsubstituted aryl, substituted or unsubstituted heteroaryl, substituted or unsubstituted phosphate, substituted or unsubstituted phosphoramidate, substituted or unsubstituted amine, substituted or unsubstituted alkylamino, substituted or unsubstituted acylamino, substituted or unsubstituted aminoalkoxy, or substituted or unsubstituted alkylthio.

In some embodiments, each of $R_2$, $R_3$, $R_4$, $R_5$, $R_6$, and $R_7$ is, independently, hydrogen, halogen, hydroxyl, substituted or unsubstituted alkyl, or substituted or unsubstituted alkoxy. In some embodiments, each of $R_2$, $R_3$, $R_4$, $R_5$, $R_6$, and $R_7$ is, independently, hydrogen, halogen, or substituted or unsubstituted alkyl. In some embodiments, each of $R_2$, $R_3$, $R_4$, $R_5$, $R_6$, and $R_7$ is hydrogen. In some embodiments, each of $R_2$, $R_3$, $R_4$, $R_5$, $R_6$, and $R_7$ is not hydrogen.

In some embodiments, $R_1$ is —$CF_3$, —$C_2F_5$, —$CHF_2$, —$CCl_3$, —$CHCl_2$, —$C_2Cl_5$, or —$CH_2CF_3$.

In some embodiments, $R_1$ is a substituted or unsubstituted haloalkyl group; and each of $R_2$, $R_3$, $R_4$, $R_5$, $R_6$, and $R_7$ is independently, hydrogen, halogen, hydroxyl, substituted or unsubstituted alkyl, or substituted or unsubstituted alkoxy.

In some embodiments, $R_1$ is —$CF_3$, —$C_2F_5$, —$CHF_2$, —$CCl_3$, —$CHCl_2$, —$C_2Cl_5$, or —$CH_2CF_3$; and each of $R_2$, $R_3$, $R_4$, $R_5$, $R_6$, and $R_7$ is independently, hydrogen, halogen, or substituted or unsubstituted alkyl.

In some embodiments, $R_1$ is —$CF_3$; and each of $R_2$, $R_3$, $R_4$, $R_5$, $R_6$, and $R_7$ is hydrogen.

In some embodiments, $R_1$ is —$CF_3$; and each of $R_2$, $R_3$, $R_4$, $R_5$, $R_6$, and $R_7$ is not hydrogen.

The present disclosure also provides compounds of Formula Ia:

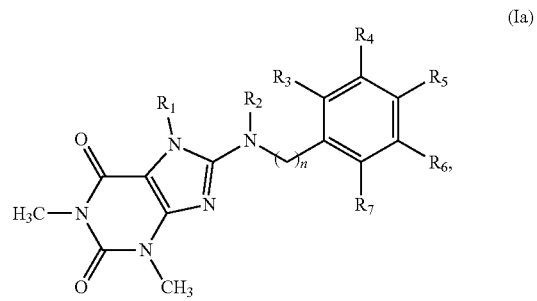

or a pharmaceutically acceptable salt thereof, wherein:
$R_1$ is hydrogen or a substituted or unsubstituted alkyl;
each $R_2$, $R_3$, $R_4$, $R_5$, $R_6$, and $R_7$ is, independently, hydrogen, halogen, hydroxyl, cyano, substituted or unsubstituted alkyl, substituted or unsubstituted alkenyl, substituted or unsubstituted haloalkyl, substituted or unsubstituted alkoxy, substituted or unsubstituted aryl, substituted or unsubstituted heteroaryl, substituted or unsubstituted phosphate, substituted or unsubstituted phosphoramidate, substituted or unsubstituted amine, substituted or unsubstituted alkylamino, substituted or unsubstituted acylamino, substituted or unsubstituted aminoalkoxy, or substituted or unsubstituted alkylthio; and
n is an integer from 0 to 5.

In some embodiments, the compound of Formula Ia is not

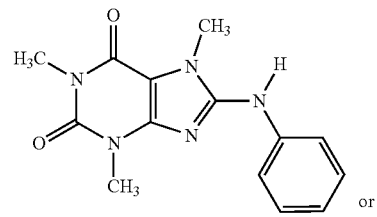

or

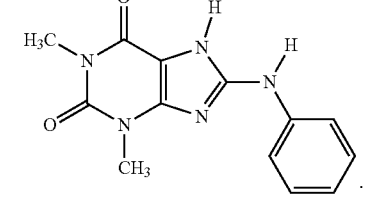

In some embodiments, $R_1$ is hydrogen, unsubstituted alkyl, —$CF_3$, —$C_2F_5$, —$CHF_2$, —$CCl_3$, —$CHCl_2$, —$C_2Cl_5$, or —$CH_2CF_3$. In some embodiments, $R_1$ is hydrogen or unsubstituted alkyl. In some embodiments, $R_1$ is hydrogen or methyl.

In some embodiments, each $R_2$, $R_3$, $R_4$, $R_5$, $R_6$, and $R_7$ is, independently, hydrogen, halogen, hydroxyl, cyano, substituted or unsubstituted alkyl, substituted or unsubstituted haloalkyl, or substituted or unsubstituted alkoxy. In some embodiments, each $R_2$, $R_3$, $R_4$, $R_5$, $R_6$, and $R_7$ is, independently, hydrogen, halogen, substituted or unsubstituted alkyl, substituted or unsubstituted haloalkyl, or substituted or unsubstituted alkoxy. In some embodiments, each $R_2$, $R_3$, $R_4$, $R_5$, $R_6$, and $R_7$ is, independently, hydrogen, halogen, unsubstituted alkyl, unsubstituted haloalkyl, or unsubstituted alkoxy. In some embodiments, each $R_2$, $R_3$, $R_4$, $R_5$, $R_6$, and $R_7$ is, independently, hydrogen, F, Cl, methyl, —$CF_3$, or methoxy.

In some embodiments, n is an integer from 0 to 3. In some embodiments, n is an integer from 0 to 2. In some embodiments, n is 0 or 1.

In some embodiments, $R_1$ is hydrogen, unsubstituted alkyl, —$CF_3$, —$C_2F_5$, —$CHF_2$, —$CCl_3$, —$CHCl_2$, —$C_2Cl_5$, or —$CH_2CF_3$; n is an integer from 0 to 3; and each $R_2$, $R_3$, $R_4$, $R_5$, $R_6$, and $R_7$ is, independently, hydrogen, halogen, hydroxyl, cyano, substituted or unsubstituted alkyl, substituted or unsubstituted haloalkyl, or substituted or unsubstituted alkoxy.

In some embodiments, $R_1$ is hydrogen or unsubstituted alkyl; n is an integer from 0 to 2; and each $R_2$, $R_3$, $R_4$, $R_5$, $R_6$, and $R_7$ is, independently, hydrogen, halogen, substituted or unsubstituted alkyl, substituted or unsubstituted haloalkyl, or substituted or unsubstituted alkoxy.

In some embodiments, $R_1$ is hydrogen or methyl; n is 0 or 1; and each $R_2$, $R_3$, $R_4$, $R_5$, $R_6$, and $R_7$ is, independently, hydrogen, halogen, unsubstituted alkyl, unsubstituted haloalkyl, or unsubstituted alkoxy.

In some embodiments, $R_1$ is hydrogen or methyl; n is 0 or 1; and each $R_2$, $R_3$, $R_4$, $R_5$, $R_6$, and $R_7$ is, independently, hydrogen, F, Cl, methyl, —$CF_3$, or methoxy.

In some embodiments, each $R_1$, $R_2$, $R_3$, $R_4$, $R_5$, $R_6$, and $R_7$ is hydrogen; and n is 0.

In some embodiments, each $R_1$, $R_2$, $R_3$, $R_5$, and $R_7$ is hydrogen; each $R_4$ and $R_6$ is methyl; and n is 0.

In some embodiments, each $R_1$, $R_2$, $R_3$, $R_4$, $R_6$, and $R_7$ is hydrogen; $R_5$ is methoxy; and n is 0.

In some embodiments, each $R_1$, $R_2$, $R_3$, $R_4$, $R_5$, and $R_7$ is hydrogen; $R_6$ is —$CF_3$; and n is 0.

In some embodiments, each $R_1$, $R_2$, $R_3$, $R_4$, $R_6$, and $R_7$ is hydrogen; $R_5$ is fluorine; and n is 1.

In some embodiments, each $R_1$, $R_2$, $R_3$, $R_4$, $R_6$, and $R_7$ is hydrogen; $R_5$ is methoxy; and n is 1.

In some embodiments, each $R_1$, $R_2$, $R_3$, $R_4$, $R_6$, and $R_7$ is hydrogen; $R_5$ is chlorine; and n is 1.

In some embodiments, $R_1$ is methyl; each $R_2$, $R_3$, $R_4$, $R_5$, $R_6$, and $R_7$ is hydrogen; and n is 0.

In some embodiments, $R_1$ is methyl; each $R_2$, $R_3$, $R_4$, and $R_7$ is hydrogen; $R_5$ and $R_6$ are methyl; and n is 0.

The present disclosure also provides compounds of Formula II:

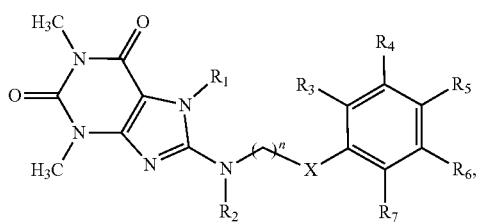

(II)

or a pharmaceutically acceptable salt thereof, wherein:
$R_1$ is hydrogen or a substituted or unsubstituted alkyl group;
each $R_2$, $R_3$, $R_4$, $R_5$, $R_6$, and $R_7$ is, independently, hydrogen, halogen, hydroxyl, substituted or unsubstituted alkyl, substituted or unsubstituted alkoxy, substituted or unsubstituted aryl, or substituted or unsubstituted amine;
X is sulfur, oxygen, or —NH; and
n is an integer from 0 to 5.

In some embodiments, $R_1$ is hydrogen or an unsubstituted alkyl. In some embodiments, $R_1$ is hydrogen or methyl. In some embodiments, $R_1$ is hydrogen.

In some embodiments, each $R_2$, $R_3$, $R_4$, $R_5$, $R_6$, and $R_7$ is, independently, hydrogen, halogen, hydroxyl, substituted or unsubstituted alkyl, substituted or unsubstituted alkoxy, substituted or unsubstituted aryl, or substituted or unsubstituted amine. In some embodiments, each $R_2$, $R_3$, $R_4$, $R_5$, $R_6$, and $R_7$ is, independently, hydrogen, halogen, or substituted or unsubstituted alkyl. In some embodiments, each $R_2$, $R_3$, $R_4$, $R_5$, $R_6$, and $R_7$ is, independently, hydrogen, halogen, or unsubstituted alkyl. In some embodiments, each $R_2$, $R_3$, $R_4$, $R_5$, $R_6$, and $R_7$ is, independently, hydrogen, halogen, or methyl.

In some embodiments, X is sulfur or oxygen. In some embodiments, X is sulfur.

In some embodiments, n is an integer from 0 to 3. In some embodiments, n is an integer from 0 to 2. In some embodiments, n is 1 or 2.

In some embodiments, $R_1$ is hydrogen or an unsubstituted alkyl; each $R_2$, $R_3$, $R_4$, $R_5$, $R_6$, and $R_7$ is, independently, hydrogen, halogen, hydroxyl, substituted or unsubstituted alkyl, substituted or unsubstituted alkoxy, substituted or unsubstituted aryl, or substituted or unsubstituted amine; X is sulfur or oxygen; and n is an integer from 0 to 3.

In some embodiments, $R_1$ is hydrogen or methyl; each $R_2$, $R_3$, $R_4$, $R_5$, $R_6$, and $R_7$ is, independently, hydrogen, halogen, or substituted or unsubstituted alkyl; X is sulfur or oxygen; and n is an integer from 0 to 2.

In some embodiments, $R_1$ is hydrogen; each $R_2$, $R_3$, $R_4$, $R_5$, $R_6$, and $R_7$ is, independently, hydrogen, halogen, or unsubstituted alkyl; X is sulfur; and n is 1 or 2.

In some embodiments, $R_1$ is hydrogen; each $R_2$, $R_3$, $R_4$, $R_5$, $R_6$, and $R_7$ is, independently, hydrogen, halogen, or methyl; X is sulfur; and n is 1 or 2.

In some embodiments, each $R_1$, $R_2$, $R_3$, $R_4$, $R_6$, and $R_7$ is hydrogen; $R_5$ is methyl; X is sulfur; and n is 2.

In some embodiments, each $R_1$, $R_2$, $R_3$, $R_4$, $R_6$, and $R_7$ is hydrogen; $R_5$ is chlorine; X is sulfur; and n is 2.

The present disclosure also provides compounds of Formula III:

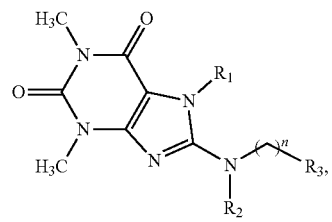

(III)

or a pharmaceutically acceptable salt thereof, wherein:
$R_1$ and $R_2$ are, independently, hydrogen or a substituted or unsubstituted alkyl;
$R_3$ is a substituted or unsubstituted heteroaryl; and
n is an integer from 0 to 5.

In some embodiments, $R_1$ and $R_2$ are, independently, hydrogen or an unsubstituted alkyl. In some embodiments, $R_1$ and $R_2$ are, independently, hydrogen or methyl. In some embodiments, $R_1$ and $R_2$ are hydrogen.

In some embodiments, n is an integer from 0 to 3. In some embodiments, n is an integer from 0 to 2. In some embodiments, n is 1.

In some embodiments, $R_3$ is an unsubstituted heteroaryl. In some embodiments, $R_3$ is unsubstituted heteroaryl having from 3 to 10 ring-forming atoms. In some embodiments, $R_3$ is unsubstituted heteroaryl having from 3 to 6 ring-forming atoms. In some embodiments, $R_3$ is unsubstituted heteroaryl having from 3 to 5 ring-forming atoms. In some embodiments, $R_3$ is pyridyl, pyrimidinyl, pyrazinyl, pyridazinyl, pyridinyl, triazinyl, furyl, quinolyl, thienyl, isoquinolyl, imidazolyl, thiazolyl, indolyl, pyrryl, oxazolyl, benzofuryl, benzothienyl, purinyl, pyrazolyl, benzthiazolyl, isoxazolyl, triazolyl, tetrazolyl, indazolyl, isothiazolyl, 1,2,4-thiadiazolyl, benzothienyl, carbazolyl, isoxazolyl, benzimidazolyl, indolinyl, pyranyl, pyrazolyl, triazolyl, oxadiazolyl, thianthrenyl, indolizinyl, isoindolyl, isobenzofuranyl, pyrrolyl, benzoxazolyl, xanthenyl, 2H-pyrrolyl, 3H-indolyl, 4H-quinolizinyl, phthalazinyl, acridinyl, naphthyridinyl, quinazolinyl, phenanthridinyl, perimidinyl, phenanthrolinyl, phenazinyl, isothiazolyl, phenothiazinyl, isoxazolyl, or furazanyl. In some embodiments, $R_3$ is pyridyl, pyrimidinyl, pyrazinyl, pyridazinyl, pyridinyl, triazinyl, furyl, quinolyl, thienyl, isoquinolyl, imidazolyl, thiazolyl, indolyl, pyrryl, oxazolyl, purinyl, benzimidazolyl, indolinyl, pyranyl, pyrazolyl, triazolyl, oxadiazolyl, thianthrenyl, or pyrrolyl. In some embodiments, $R_3$ is 2-thienyl or 3-thienyl.

In some embodiments, $R_1$ and $R_2$ are, independently, hydrogen or an unsubstituted alkyl; n is an integer from 0 to 3; and $R_3$ is an unsubstituted heteroaryl.

In some embodiments, $R_1$ and $R_2$ are, independently, hydrogen or an unsubstituted alkyl; n is an integer from 0 to 3; and $R_3$ is unsubstituted heteroaryl having from 3 to 10 ring-forming atoms.

In some embodiments, $R_1$ and $R_2$ are, independently, hydrogen or methyl; n is an integer from 0 to 2; and $R_3$ is unsubstituted heteroaryl having from 3 to 6 ring-forming atoms.

In some embodiments, $R_1$ and $R_2$ are, independently, hydrogen or methyl; n is an integer from 0 to 2; and $R_3$ is unsubstituted heteroaryl having from 3 to 5 ring-forming atoms.

In some embodiments, $R_1$ and $R_2$ are hydrogen; n is an integer from 0 to 2; and $R_3$ is pyridyl, pyrimidinyl, pyrazinyl, pyridazinyl, pyridinyl, triazinyl, furyl, quinolyl, isoquinolyl, thienyl, imidazolyl, thiazolyl, indolyl, pyrryl, oxazolyl, benzofuryl, benzothienyl, pyrazolyl, benzthiazolyl, isoxazolyl, triazolyl, tetrazolyl, indazolyl, isothiazolyl, 1,2,4-thiadiazolyl, benzothienyl, purinyl, carbazolyl, isoxazolyl, benzimidazolyl, indolinyl, pyranyl, pyrazolyl, triazolyl, oxadiazolyl, thianthrenyl, indolizinyl, isoindolyl, isobenzofuranyl, pyrrolyl, benzoxazolyl, xanthenyl, 2H-pyrrolyl, 3H-indolyl, 4H-quinolizinyl, phthalazinyl, acridinyl, naphthyridinyl, quinazolinyl, phenanthridinyl, perimidinyl, phenanthrolinyl, phenazinyl, isothiazolyl, phenothiazinyl, isoxazolyl, or furazanyl.

In some embodiments, $R_1$ and $R_2$ are hydrogen; n is 1; and $R_3$ is pyridyl, pyrimidinyl, pyrazinyl, pyridazinyl, pyridinyl, triazinyl, furyl, quinolyl, isoquinolyl, thienyl, imidazolyl, thiazolyl, indolyl, pyrryl, oxazolyl, purinyl, benzimidazolyl, indolinyl, pyranyl, pyrazolyl, triazolyl, oxadiazolyl, thianthrenyl, or pyrrolyl.

In some embodiments, $R_1$ and $R_2$ are hydrogen; n is 1; and $R_3$ is 2-thienyl or 3-thienyl.

In some embodiments, $R_1$ and $R_2$ are hydrogen; $R_3$ is -2-thienyl; and n is 1.

Compound formulas are as follows:

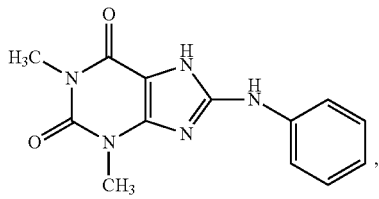
CB002

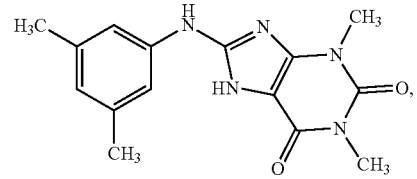
Analog 2

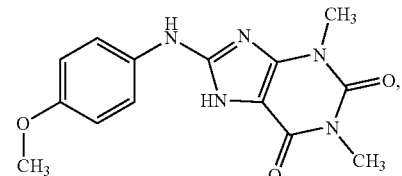
Analog 3

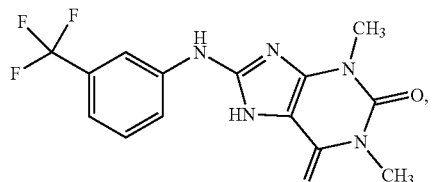
Analog 4

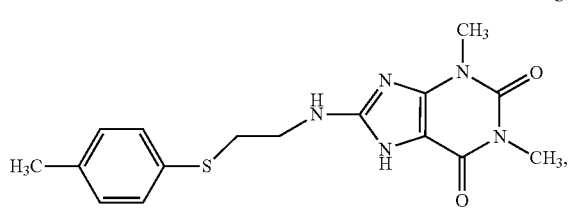
Analog 5

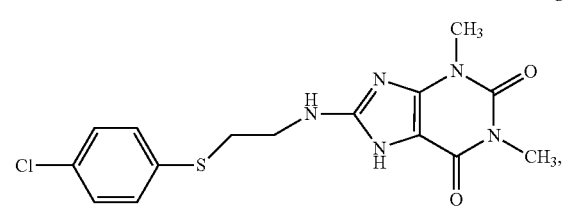
Analog 6

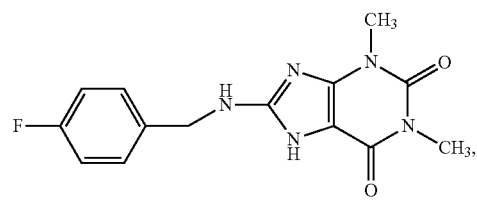
Analog 7

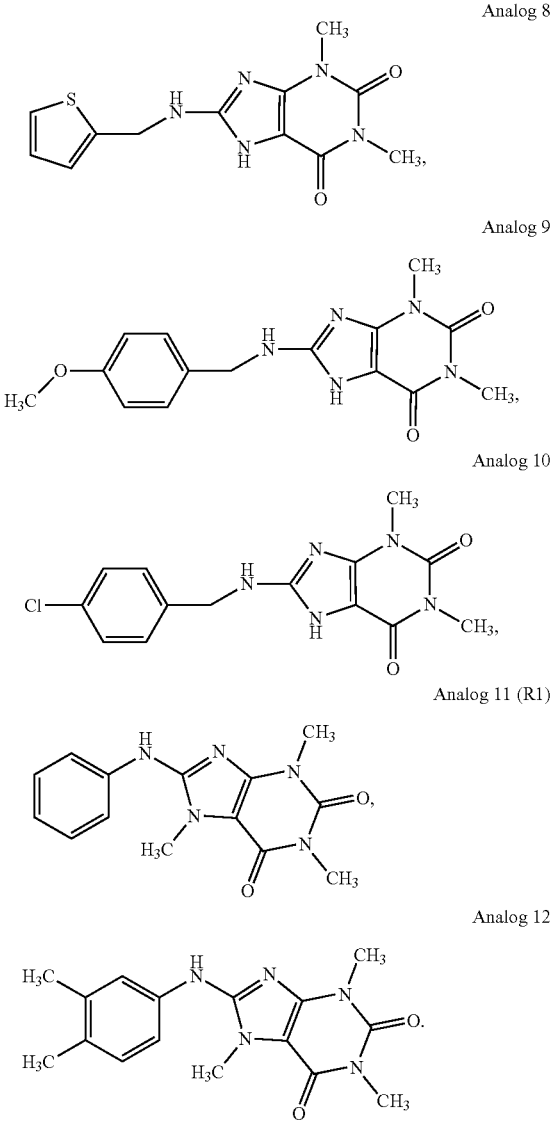

Analog 8

Analog 9

Analog 10

Analog 11 (R1)

Analog 12

In some embodiments, the compound is any one or more of Analog 1, Analog 2, Analog 3, Analog 4, Analog 5, Analog 6, Analog 7, Analog 8, Analog 9, Analog 10, Analog 11, or Analog 12, or any combination thereof. In some embodiments, the compound is Analog 4. In some embodiments, the compound is Analog 11.

In some embodiments, the compound(s) of Formula I or a pharmaceutically acceptable salt thereof are a component of a pharmaceutical composition further comprising a pharmaceutically acceptable carrier. In some embodiments, the compound(s) of Formula Ia or a pharmaceutically acceptable salt thereof are a component of a pharmaceutical composition further comprising a pharmaceutically acceptable carrier. In some embodiments, the compound(s) of Formula II or a pharmaceutically acceptable salt thereof are a component of a pharmaceutical composition further comprising a pharmaceutically acceptable carrier. In some embodiments, the compound(s) of Formula III or a pharmaceutically acceptable salt thereof are a component of a pharmaceutical composition further comprising a pharmaceutically acceptable carrier.

The pharmaceutical composition my optionally comprise a neoadjuvant therapeutic agent, a chemotherapeutic agent, an immunotherapeutic agent, a lysosome inhibitor, or a calpain inhibitor, or any combination thereof.

Neoadjuvant therapeutic agents include all forms of treatment of cancer including, but not limited to, traditional chemotherapy (i.e., anti-cancer agents or chemotherapeutic agents, whether they are administered parenterally or orally), immunotherapy, small molecule enzyme or kinase inhibitors, intravesical therapies, antibody inhibitors of receptors or kinases, antibody-drug conjugates, and radiation therapy.

Examples of chemotherapeutic agents include, without limitation, methotrexate, taxol, mercaptopurine, thioguanine, hydroxyurea, cytarabine, mitomycin, cyclophosphamide, ifosfamide, nitrosourea, cisplatin, carboplatin, oxaliplatin, nedaplatin, triplatin tetranitrate, phenanthriplatin, picoplatin, satraplatin, dacarbazine, procarbizine, an etoposide, a campathecin, bleomycin, doxorubicin, idarubicin, daunorubicin, dactinomycin, distamycin A, etidium, netropsin, auristatin, amsacrine, prodigiosin, bortexomib, pibenzimol, tomaymycin, duocarmycin SA, plicamycin, mitoxantrone, asparaginase, vinblastine, vincristine, MG132, tunicamycin, oligomycin, vinorelbine, paclitaxel, docetaxel, CPT-11, gleevec, erlotinib, gefitinib, ibrutinib, crizotinib, ceritinib, flavopiridol, gemcitabine, lapatinib, navitoclax, sorafenib, regorafenib, ganetespib, irinotecan, or 5-fluorouracil, or any combination thereof. In some embodiments, the chemotherapeutic agent is a combination of agents, such as, for example, methotrexate/vincristine/doxorubicin/cisplatin (MVAC) or gemcitabine/cisplatin.

In some embodiments, the neoadjuvant agent is an immunotherapeutic agent such as, for example, OPDIVO® (nivolumab), KEYTRUDA® (pembrolizumab), TECENTRIQ® (atezolizumab), IMFINZI® (durvalab), YERVOY® (ipilumumab), BAVENCIO® (avelumab), ERBITUX® (cetuxumab), AVASTIN® (bevacizumab), or HERCEPTIN® (trastuzumab), or any combination thereof.

An example of a lysosome inhibitor is chloroquine.

Examples of calpain inhibitors include, without limitation, AK275, MDL28170, PD150606, SJA6017, ABT-705253, or SNJ-1945, or any combination thereof.

In some embodiments, the ratio of the compound to the chemotherapeutic agent, the lysosome inhibitor, the immunotherapy agent, or the calpain inhibitor in the pharmaceutical composition is from about 0.01:1 to about 100:1 w/w.

The compositions may be prepared to provide from about 0.05 mg to about 500 mg of the compound, or pharmaceutically acceptable salt thereof. The compositions may comprise from about 1 mg to about 200 mg of the compound, may comprise from about 10 mg to about 200 mg of the compound, may comprise from about 10 mg to about 100 mg of the compound, may comprise from about 50 mg to about 100 mg of the compound, may comprise from about 20 mg to about 400 mg of the compound, may comprise from about 100 mg to about 300 mg of the compound, and may comprise from about 50 mg to about 250 mg of the compound, or pharmaceutically acceptable salt thereof.

The pharmaceutical compositions described herein can be administered to a patient in need thereof in an oral formulation, an intravenous formulation, a topical formulation, an intraperitoneal formulation, an intrapleural formulation, an intravesical formulation, or an intrathecal formulation. The compositions may be formulated in a suitable controlled-release vehicle, with an adjuvant, or as a depot formulation.

Preparations for parenteral administration include sterile solutions ready for injection, sterile dry soluble products ready to be combined with a solvent just prior to use, including hypodermic tablets, sterile suspensions ready for injection, sterile dry insoluble products ready to be combined with a vehicle just prior to use and sterile emulsions.

Solid dosage forms include tablets, pills, powders, bulk powders, capsules, granules, and combinations thereof. Solid dosage forms may be prepared as compressed, chewable lozenges and tablets which may be enteric-coated, sugar coated or film-coated. Solid dosage forms may be hard or encased in soft gelatin, and granules and powders may be provided in non-effervescent or effervescent form. Solid dosage forms may be prepared for dissolution or suspension in a liquid or semi-liquid vehicle prior to administration. Solid dosage forms may be prepared for immediate release, controlled release, or any combination thereof. Controlled release includes, but is not limited to delayed release, sustained release, timed pulsatile release, and location-specific pulsatile release, and combinations thereof.

Liquid dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions may be oil-in water or water-in-oil emulsions.

In some embodiments, the oral formulation is a pill, tablet, capsule, cachet, gel-cap, pellet, powder, granule, or liquid.

Pharmaceutically acceptable excipients utilized in solid dosage forms include coatings, binders, lubricants, diluents, disintegrating agents, coloring agents, flavoring agents, preservatives, sweeteners, and wetting agents. Enteric-coated tablets, due to their enteric-coating, resist the action of stomach acid and dissolve or disintegrate in the neutral or alkaline intestines. Other examples of coatings include sugar coatings and polymer coatings. Sweetening agents are especially useful in the formation of chewable tablets and lozenges. Pharmaceutically acceptable excipients used in liquid dosage forms includes solvents, suspending agents, dispersing agents, emulsifying agents, surfactants, emollients, coloring agents, flavoring agents, preservatives, and sweeteners.

Non-limiting examples of binders include glucose solution, acacia mucilage, gelatin solution, sucrose and starch paste. Non-limiting examples of lubricants include talc, starch, magnesium or calcium stearate, lycopodium and stearic acid. Non-limiting examples of diluents include lactose, sucrose, starch, kaolin, salt, mannitol and dicalcium phosphate. Non-limiting examples of disintegrating agents include corn starch, potato starch, bentonite, methylcellulose, agar and carboxymethylcellulose. Non-limiting examples of emulsifying agents include gelatin, acacia, tragacanth, bentonite, and surfactants such as polyoxyethylene sorbitan monooleate. Non-limiting examples of suspending agents include sodium carboxymethylcellulose, pectin, tragacanth, veegum and acacia.

Non-limiting examples of coloring agents include any of the approved certified water soluble FD and C dyes, mixtures thereof, and water insoluble FD and D dyes suspended on alumina hydrate. Non-limiting examples of sweetening agents include dextrose, sucrose, fructose, lactose, mannitol and artificial sweetening agents such as saccharin, aspartame, sucralose, acelsulfame potassium, and other artificial sweeteners. Non-limiting examples of flavoring agents include synthetic flavors and natural flavors extracted from plants such as fruits and mints, and synthetic blends of compounds which produce a pleasant sensation. Non-limiting examples of wetting agents include propylene glycol monostearate, sorbitan monooleate, diethylene glycol monolaurate and polyoxyethylene laural ether. Non-limiting examples of enteric-coatings include fatty acids, fats, waxes, shellac, ammoniated shellac and cellulose acetate phthalates. Non-limiting examples of film coatings include hydroxyethylcellulose, sodium carboxymethylcellulose, polyethylene glycol 4000 and cellulose acetate phthalate. Non-limiting examples of preservatives include glycerin, methyl and propylparaben, ethylparaben, butylparaben, isobutylparaben, isopropylparaben, benzylparaben, citrate, benzoic acid, sodium benzoate and alcohol.

Elixirs include clear, sweetened, hydroalcoholic preparations. Pharmaceutically acceptable carriers used in elixirs include solvents. Syrups include concentrated aqueous solutions of a sugar, for example, sucrose, and may contain a preservative. An emulsion is a two-phase system in which one liquid is dispersed throughout another liquid. Pharmaceutically acceptable carriers used in emulsions may include emulsifying agents and preservatives. Suspensions may use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substance used in effervescent granules, to be reconstituted into a liquid oral dosage form, include organic acids and a source of carbon dioxide. Sources of carbon dioxide include sodium bicarbonate and sodium carbonate. Coloring and flavoring agents may be used in all such dosage forms.

Additional excipients that may be included in any dosage forms include, but are not limited to antimicrobial agents, isotonic agents, buffers, antioxidants, local anesthetic agents, sequestering or chelating agents, analgesic agents, antiemetic agents, and other agents to enhance selected characteristics of the formulation.

Antimicrobial agents may be cidal or static, and may be antimicrobial, antifungal, antiparasitic, or antiviral. Non-limiting examples of commonly used antimicrobial agents include phenols or cresols, mercurials, benzyl alcohol, chlorobutanol, methyl and propyl p-hydroxybenzoic acid esters, thimerosal, benzalkonium chloride and benzethonium chloride. Acidic or basic pH may be used for antimicrobial effects in some aspects. Non-limiting examples of isotonic agents include sodium chloride and dextrose. Non-limiting examples of buffers include phosphate and citrate buffers. A non-limiting example of a chelating agent for metal ions is EDTA.

The present disclosure also provides methods for treating a cancer in a mammal. The methods comprise administering to the mammal in need thereof a compound of Formula I:

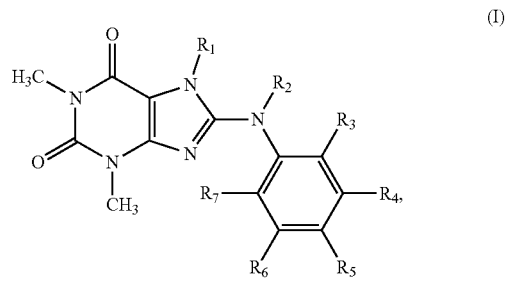

or a pharmaceutically acceptable salt thereof, wherein:
$R_1$ is hydrogen or a substituted or unsubstituted haloalkyl group; and
each $R_2$, $R_3$, $R_4$, $R_5$, $R_6$, and $R_7$ is, independently, hydrogen, halogen, hydroxyl, cyano, substituted or unsubstituted alkyl, substituted or unsubstituted alkenyl, substituted or unsubstituted alkoxy, substituted or unsubstituted aryl, substituted or unsubstituted heteroaryl, substituted or unsubstituted phosphate, substituted or unsubstituted phosphoramidate, substituted or unsubstituted amine, substituted or unsubstituted alkylamino, substituted or unsubstituted acylamino, substituted or unsubstituted aminoalkoxy, or substituted or unsubstituted alkylthio.

In some embodiments, each of $R_2$, $R_3$, $R_4$, $R_5$, $R_6$, and $R_7$ is, independently, hydrogen, halogen, hydroxyl, substituted or unsubstituted alkyl, or substituted or unsubstituted alkoxy. In some embodiments, each of $R_2$, $R_3$, $R_4$, $R_5$, $R_6$, and $R_7$ is, independently, hydrogen, halogen, or substituted or unsubstituted alkyl. In some embodiments, each of $R_2$, $R_3$, $R_4$, $R_5$, $R_6$, and $R_7$ is hydrogen. In some embodiments, each of $R_2$, $R_3$, $R_4$, $R_5$, $R_6$, and $R_7$ is not hydrogen.

In some embodiments, $R_1$ is —$CF_3$, —$C_2F_5$, —$CHF_2$, —$CCl_3$, —$CHCl_2$, —$C_2Cl_5$, or —$CH_2CF_3$.

In some embodiments, $R_1$ is a substituted or unsubstituted haloalkyl group; and each of $R_2$, $R_3$, $R_4$, $R_5$, $R_6$, and $R_7$ is independently, hydrogen, halogen, hydroxyl, substituted or unsubstituted alkyl, or substituted or unsubstituted alkoxy.

In some embodiments, $R_1$ is —$CF_3$, —$C_2F_5$, —$CHF_2$, —$CCl_3$, —$CHCl_2$, —$C_2Cl_5$, or —$CH_2CF_3$; and each of $R_2$, $R_3$, $R_4$, $R_5$, $R_6$, and $R_7$ is independently, hydrogen, halogen, or substituted or unsubstituted alkyl.

In some embodiments, $R_1$ is —$CF_3$; and each of $R_2$, $R_3$, $R_4$, $R_5$, $R_6$, and $R_7$ is hydrogen.

In some embodiments, $R_1$ is —$CF_3$; and each of $R_2$, $R_3$, $R_4$, $R_5$, $R_6$, and $R_7$ is not hydrogen.

The present disclosure also provides methods of treating a cancer in a mammal comprising administering to the mammal in need thereof a compound of Formula Ia:

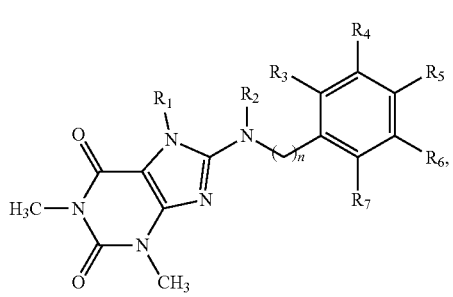

(Ia)

or a pharmaceutically acceptable salt thereof, wherein:

$R_1$ is hydrogen or a substituted or unsubstituted alkyl;

each $R_2$, $R_3$, $R_4$, $R_5$, $R_6$, and $R_7$ is, independently, hydrogen, halogen, hydroxyl, cyano, substituted or unsubstituted alkyl, substituted or unsubstituted alkenyl, substituted or unsubstituted haloalkyl, substituted or unsubstituted alkoxy, substituted or unsubstituted aryl, substituted or unsubstituted heteroaryl, substituted or unsubstituted phosphate, substituted or unsubstituted phosphoramidate, substituted or unsubstituted amine, substituted or unsubstituted alkylamino, substituted or unsubstituted acylamino, substituted or unsubstituted aminoalkoxy, or substituted or unsubstituted alkylthio; and n is an integer from 0 to 5.

In some embodiments, the compound of Formula Ia is not

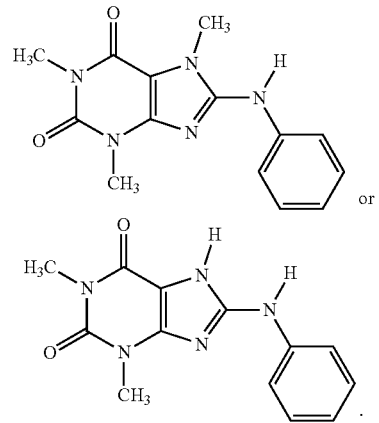

or

In some embodiments, $R_1$ is hydrogen, unsubstituted alkyl, —$CF_3$, —$C_2F_5$, —$CHF_2$, —$CCl_3$, —$CHCl_2$, —$C_2Cl_5$, or —$CH_2CF_3$. In some embodiments, $R_1$ is hydrogen or unsubstituted alkyl. In some embodiments, $R_1$ is hydrogen or methyl.

In some embodiments, each $R_2$, $R_3$, $R_4$, $R_5$, $R_6$, and $R_7$ is, independently, hydrogen, halogen, hydroxyl, cyano, substituted or unsubstituted alkyl, substituted or unsubstituted haloalkyl, or substituted or unsubstituted alkoxy. In some embodiments, each $R_2$, $R_3$, $R_4$, $R_5$, $R_6$, and $R_7$ is, independently, hydrogen, halogen, substituted or unsubstituted alkyl, substituted or unsubstituted haloalkyl, or substituted or unsubstituted alkoxy. In some embodiments, each $R_2$, $R_3$, $R_4$, $R_5$, $R_6$, and $R_7$ is, independently, hydrogen, halogen, unsubstituted alkyl, unsubstituted haloalkyl, or unsubstituted alkoxy. In some embodiments, each $R_2$, $R_3$, $R_4$, $R_5$, $R_6$, and $R_7$ is, independently, hydrogen, F, Cl, methyl, —$CF_3$, or methoxy.

In some embodiments, n is an integer from 0 to 3. In some embodiments, n is an integer from 0 to 2. In some embodiments, n is 0 or 1.

In some embodiments, $R_1$ is hydrogen, unsubstituted alkyl, —$CF_3$, —$C_2F_5$, —$CHF_2$, —$CCl_3$, —$CHCl_2$, —$C_2Cl_5$, or —$CH_2CF_3$; n is an integer from 0 to 3; and each $R_2$, $R_3$, $R_4$, $R_5$, $R_6$, and $R_7$ is, independently, hydrogen, halogen, hydroxyl, cyano, substituted or unsubstituted alkyl, substituted or unsubstituted haloalkyl, or substituted or unsubstituted alkoxy.

In some embodiments, $R_1$ is hydrogen or unsubstituted alkyl; n is an integer from 0 to 2; and each $R_2$, $R_3$, $R_4$, $R_5$, $R_6$, and $R_7$ is, independently, hydrogen, halogen, substituted or unsubstituted alkyl, substituted or unsubstituted haloalkyl, or substituted or unsubstituted alkoxy.

In some embodiments, $R_1$ is hydrogen or methyl; n is 0 or 1; and each $R_2$, $R_3$, $R_4$, $R_5$, $R_6$, and $R_7$ is, independently, hydrogen, halogen, unsubstituted alkyl, unsubstituted haloalkyl, or unsubstituted alkoxy.

In some embodiments, $R_1$ is hydrogen or methyl; n is 0 or 1; and each $R_2$, $R_3$, $R_4$, $R_5$, $R_6$, and $R_7$ is, independently, hydrogen, F, Cl, methyl, —$CF_3$, or methoxy.

In some embodiments, each $R_1$, $R_2$, $R_3$, $R_4$, $R_5$, $R_6$, and $R_7$ is hydrogen; and n is 0.

In some embodiments, each $R_1$, $R_2$, $R_3$, $R_5$, and $R_7$ is hydrogen; each $R_4$ and $R_6$ is methyl; and n is 0.

In some embodiments, each $R_1$, $R_2$, $R_3$, $R_4$, $R_6$, and $R_7$ is hydrogen; $R_5$ is methoxy; and n is 0.

In some embodiments, each $R_1$, $R_2$, $R_3$, $R_4$, $R_5$, and $R_7$ is hydrogen; $R_6$ is —CF$_3$; and n is 0.

In some embodiments, each $R_1$, $R_2$, $R_3$, $R_4$, $R_6$, and $R_7$ is hydrogen; $R_5$ is fluorine; and n is 1.

In some embodiments, each $R_1$, $R_2$, $R_3$, $R_4$, $R_6$, and $R_7$ is hydrogen; $R_5$ is methoxy; and n is 1.

In some embodiments, each $R_1$, $R_2$, $R_3$, $R_4$, $R_6$, and $R_7$ is hydrogen; $R_5$ is chlorine; and n is 1.

In some embodiments, $R_1$ is methyl; each $R_2$, $R_3$, $R_4$, $R_5$, $R_6$, and $R_7$ is hydrogen; and n is 0.

In some embodiments, $R_1$ is methyl; each $R_2$, $R_3$, $R_4$, and $R_7$ is hydrogen; $R_5$ and $R_6$ are methyl; and n is 0.

The present disclosure also provides methods of treating a cancer in a mammal comprising administering to the mammal in need thereof a compound of Formula II:

(II)

or a pharmaceutically acceptable salt thereof, wherein:

$R_1$ is hydrogen or a substituted or unsubstituted alkyl group;

each $R_2$, $R_3$, $R_4$, $R_5$, $R_6$, and $R_7$ is, independently, hydrogen, halogen, hydroxyl, substituted or unsubstituted alkyl, substituted or unsubstituted alkoxy, substituted or unsubstituted aryl, or substituted or unsubstituted amine;

X is sulfur, oxygen, or —NH; and n is an integer from 0 to 5.

In some embodiments, $R_1$ is hydrogen or an unsubstituted alkyl. In some embodiments, $R_1$ is hydrogen or methyl. In some embodiments, $R_1$ is hydrogen.

In some embodiments, each $R_2$, $R_3$, $R_4$, $R_5$, $R_6$, and $R_7$ is, independently, hydrogen, halogen, hydroxyl, substituted or unsubstituted alkyl, substituted or unsubstituted alkoxy, substituted or unsubstituted aryl, or substituted or unsubstituted amine. In some embodiments, each $R_2$, $R_3$, $R_4$, $R_5$, $R_6$, and $R_7$ is, independently, hydrogen, halogen, or substituted or unsubstituted alkyl. In some embodiments, each $R_2$, $R_3$, $R_4$, $R_5$, $R_6$, and $R_7$ is, independently, hydrogen, halogen, or unsubstituted alkyl. In some embodiments, each $R_2$, $R_3$, $R_4$, $R_5$, $R_6$, and $R_7$ is, independently, hydrogen, halogen, or methyl.

In some embodiments, X is sulfur or oxygen. In some embodiments, X is sulfur.

In some embodiments, n is an integer from 0 to 3. In some embodiments, n is an integer from 0 to 2. In some embodiments, n is 1 or 2.

In some embodiments, $R_1$ is hydrogen or an unsubstituted alkyl; each $R_2$, $R_3$, $R_4$, $R_5$, $R_6$, and $R_7$ is, independently, hydrogen, halogen, hydroxyl, substituted or unsubstituted alkyl, substituted or unsubstituted alkoxy, substituted or unsubstituted aryl, or substituted or unsubstituted amine; X is sulfur or oxygen; and n is an integer from 0 to 3.

In some embodiments, $R_1$ is hydrogen or methyl; each $R_2$, $R_3$, $R_4$, $R_5$, $R_6$, and $R_7$ is, independently, hydrogen, halogen, or substituted or unsubstituted alkyl; X is sulfur or oxygen; and n is an integer from 0 to 2.

In some embodiments, $R_1$ is hydrogen; each $R_2$, $R_3$, $R_4$, $R_5$, $R_6$, and $R_7$ is, independently, hydrogen, halogen, or unsubstituted alkyl; X is sulfur; and n is 1 or 2.

In some embodiments, $R_1$ is hydrogen; each $R_2$, $R_3$, $R_4$, $R_5$, $R_6$, and $R_7$ is, independently, hydrogen, halogen, or methyl; X is sulfur; and n is 1 or 2.

In some embodiments, each $R_1$, $R_2$, $R_3$, $R_4$, $R_6$, and $R_7$ is hydrogen; $R_5$ is methyl; X is sulfur; and n is 2.

In some embodiments, each $R_1$, $R_2$, $R_3$, $R_4$, $R_6$, and $R_7$ is hydrogen; $R_5$ is chlorine; X is sulfur; and n is 2.

The present disclosure also provides methods of treating a cancer in a mammal comprising administering to the mammal in need thereof a compound of Formula III:

(III)

or a pharmaceutically acceptable salt thereof, wherein:

$R_1$ and $R_2$ are, independently, hydrogen or a substituted or unsubstituted alkyl;

$R_3$ is a substituted or unsubstituted heteroaryl; and n is an integer from 0 to 5.

In some embodiments, $R_1$ and $R_2$ are, independently, hydrogen or an unsubstituted alkyl. In some embodiments, $R_1$ and $R_2$ are, independently, hydrogen or methyl. In some embodiments, $R_1$ and $R_2$ are hydrogen.

In some embodiments, n is an integer from 0 to 3. In some embodiments, n is an integer from 0 to 2. In some embodiments, n is 1.

In some embodiments, $R_3$ is an unsubstituted heteroaryl. In some embodiments, $R_3$ is unsubstituted heteroaryl having from 3 to 10 ring-forming atoms. In some embodiments, $R_3$ is unsubstituted heteroaryl having from 3 to 6 ring-forming atoms. In some embodiments, $R_3$ is unsubstituted heteroaryl having from 3 to 5 ring-forming atoms. In some embodiments, $R_3$ is pyridyl, pyrimidinyl, pyrazinyl, pyridazinyl, pyridinyl, triazinyl, furyl, quinolyl, isoquinolyl, thienyl, imidazolyl, thiazolyl, indolyl, pyrryl, oxazolyl, benzofuryl, benzothienyl, pyrazolyl, benzthiazolyl, isoxazolyl, triazolyl, tetrazolyl, indazolyl, isothiazolyl, 1,2,4-thiadiazolyl, benzothienyl, purinyl, carbazolyl, isoxazolyl, benzimidazolyl, indolinyl, pyranyl, pyrazolyl, triazolyl, oxadiazolyl, thianthrenyl, indolizinyl, isoindolyl, isobenzofuranyl, pyrrolyl, benzoxazolyl, xanthenyl, 2H-pyrrolyl, 3H-indolyl, 4H-quinolizinyl, phthalazinyl, acridinyl, naphthyridinyl, quinazolinyl, phenanthridinyl, perimidinyl, phenanthrolinyl, phenazinyl, isothiazolyl, phenothiazinyl, isoxazolyl, or furazanyl. In some embodiments, $R_3$ is pyridyl, pyrimidinyl, pyrazinyl, pyridazinyl, pyridinyl, triazinyl, furyl, quinolyl, isoquinolyl, thienyl, imidazolyl, thiazolyl, indolyl, pyrryl, oxazolyl, purinyl, benzimidazolyl, indolinyl, pyranyl, pyrazolyl, triazolyl, oxadiazolyl, thianthrenyl, or pyrrolyl. In some embodiments, $R_3$ is 2-thienyl or 3-thienyl.

In some embodiments, $R_1$ and $R_2$ are, independently, hydrogen or an unsubstituted alkyl; n is an integer from 0 to 3; and $R_3$ is an unsubstituted heteroaryl.

In some embodiments, $R_1$ and $R_2$ are, independently, hydrogen or an unsubstituted alkyl; n is an integer from 0 to 3; and $R_3$ is unsubstituted heteroaryl having from 3 to 10 ring-forming atoms.

In some embodiments, $R_1$ and $R_2$ are, independently, hydrogen or methyl; n is an integer from 0 to 2; and $R_3$ is unsubstituted heteroaryl having from 3 to 6 ring-forming atoms.

In some embodiments, $R_1$ and $R_2$ are, independently, hydrogen or methyl; n is an integer from 0 to 2; and $R_3$ is unsubstituted heteroaryl having from 3 to 5 ring-forming atoms.

In some embodiments, $R_1$ and $R_2$ are hydrogen; n is an integer from 0 to 2; and $R_3$ is pyridyl, pyrimidinyl, pyrazinyl, pyridazinyl, pyridinyl, triazinyl, furyl, quinolyl, isoquinolyl, thienyl, imidazolyl, thiazolyl, indolyl, pyrryl, oxazolyl, benzofuryl, benzothienyl, pyrazolyl, benzthiazolyl, isoxazolyl, triazolyl, tetrazolyl, indazolyl, isothiazolyl, 1,2,4-thiadiazolyl, benzothienyl, purinyl, carbazolyl, isoxazolyl, benzimidazolyl, indolinyl, pyranyl, pyrazolyl, triazolyl, oxadiazolyl, thianthrenyl, indolizinyl, isoindolyl, isobenzofuranyl, pyrrolyl, benzoxazolyl, xanthenyl, 2H-pyrrolyl, 3H-indolyl, 4H-quinolizinyl, phthalazinyl, acridinyl, naphthyridinyl, quinazolinyl, phenanthridinyl, perimidinyl, phenanthrolinyl, phenazinyl, isothiazolyl, phenothiazinyl, isoxazolyl, or furazanyl.

In some embodiments, $R_1$ and $R_2$ are hydrogen; n is 1; and $R_3$ is pyridyl, pyrimidinyl, pyrazinyl, pyridazinyl, pyridinyl, triazinyl, furyl, quinolyl, isoquinolyl, thienyl, imidazolyl, thiazolyl, indolyl, pyrryl, oxazolyl, purinyl, benzimidazolyl, indolinyl, pyranyl, pyrazolyl, triazolyl, oxadiazolyl, thianthrenyl, or pyrrolyl.

In some embodiments, $R_1$ and $R_2$ are hydrogen; n is 1; and $R_3$ is 2-thienyl or 3-thienyl.

In some embodiments, $R_1$ and $R_2$ are hydrogen; $R_3$ is -2-thienyl; and n is 1.

The present disclosure also provides methods for restoring the tumor suppressor protein p53 signaling pathway within a tumor cell of a mammal comprising administering to the mammal in need thereof a compound of Formula I:

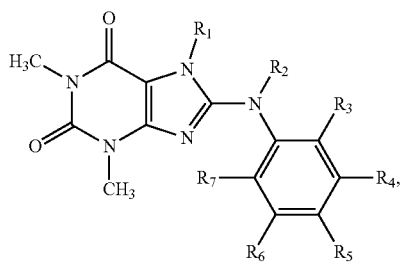

(I)

or a pharmaceutically acceptable salt thereof, wherein:

$R_1$ is hydrogen or a substituted or unsubstituted haloalkyl group; and each $R_2$, $R_3$, $R_4$, $R_5$, $R_6$, and $R_7$ is, independently, hydrogen, halogen, hydroxyl, cyano, substituted or unsubstituted alkyl, substituted or unsubstituted alkenyl, substituted or unsubstituted alkoxy, substituted or unsubstituted aryl, substituted or unsubstituted heteroaryl, substituted or unsubstituted phosphate, substituted or unsubstituted phosphoramidate, substituted or unsubstituted amine, substituted or unsubstituted alkylamino, substituted or unsubstituted acylamino, substituted or unsubstituted aminoalkoxy, or substituted or unsubstituted alkylthio.

In some embodiments, each of $R_2$, $R_3$, $R_4$, $R_5$, $R_6$, and $R_7$ is, independently, hydrogen, halogen, hydroxyl, substituted or unsubstituted alkyl, or substituted or unsubstituted alkoxy. In some embodiments, each of $R_2$, $R_3$, $R_4$, $R_5$, $R_6$, and $R_7$ is, independently, hydrogen, halogen, or substituted or unsubstituted alkyl. In some embodiments, each of $R_2$, $R_3$, $R_4$, $R_5$, $R_6$, and $R_7$ is hydrogen. In some embodiments, each of $R_2$, $R_3$, $R_4$, $R_5$, $R_6$, and $R_7$ is not hydrogen.

In some embodiments, $R_1$ is $-CF_3$, $-C_2F_5$, $-CHF_2$, $-CCl_3$, $-CHCl_2$, $-C_2Cl_5$, or $-CH_2CF_3$.

In some embodiments, $R_1$ is a substituted or unsubstituted haloalkyl group; and each of $R_2$, $R_3$, $R_4$, $R_5$, $R_6$, and $R_7$ is independently, hydrogen, halogen, hydroxyl, substituted or unsubstituted alkyl, or substituted or unsubstituted alkoxy.

In some embodiments, $R_1$ is $-CF_3$, $-C_2F_5$, $-CHF_2$, $-CCl_3$, $-CHCl_2$, $-C_2Cl_5$, or $-CH_2CF_3$; and each of $R_2$, $R_3$, $R_4$, $R_5$, $R_6$, and $R_7$ is independently, hydrogen, halogen, or substituted or unsubstituted alkyl.

In some embodiments, $R_1$ is $-CF_3$; and each of $R_2$, $R_3$, $R_4$, $R_5$, $R_6$, and $R_7$ is hydrogen.

In some embodiments, $R_1$ is $-CF_3$; and each of $R_2$, $R_3$, $R_4$, $R_5$, $R_6$, and $R_7$ is not hydrogen.

The present disclosure also provides methods of restoring the tumor suppressor protein p53 signaling pathway within a tumor cell of a mammal comprising administering to the mammal in need thereof a compound of Formula Ia:

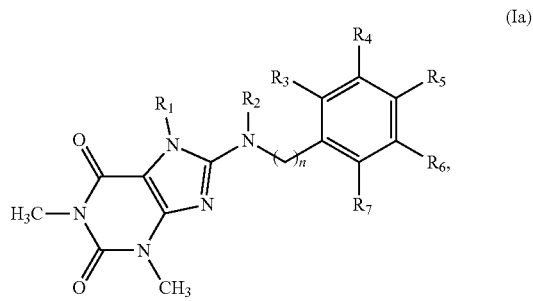

(Ia)

or a pharmaceutically acceptable salt thereof, wherein:

$R_1$ is hydrogen or a substituted or unsubstituted alkyl;

each $R_2$, $R_3$, $R_4$, $R_5$, $R_6$, and $R_7$ is, independently, hydrogen, halogen, hydroxyl, cyano, substituted or unsubstituted alkyl, substituted or unsubstituted alkenyl, substituted or unsubstituted haloalkyl, substituted or unsubstituted alkoxy, substituted or unsubstituted aryl, substituted or unsubstituted heteroaryl, substituted or unsubstituted phosphate, substituted or unsubstituted phosphoramidate, substituted or unsubstituted amine, substituted or unsubstituted alkylamino, substituted or unsubstituted acylamino, substituted or unsubstituted aminoalkoxy, or substituted or unsubstituted alkylthio; and n is an integer from 0 to 5.

In some embodiments, the compound of Formula Ia is not

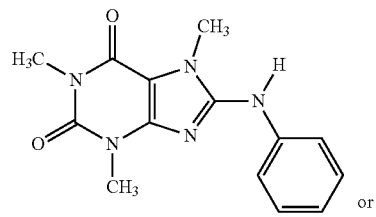

or

-continued

In some embodiments, $R_1$ is hydrogen, unsubstituted alkyl, —$CF_3$, —$C_2F_5$, —$CHF_2$, —$CCl_3$, —$CHCl_2$, —$C_2Cl_5$, or —$CH_2CF_3$. In some embodiments, $R_1$ is hydrogen or unsubstituted alkyl. In some embodiments, $R_1$ is hydrogen or methyl.

In some embodiments, each $R_2$, $R_3$, $R_4$, $R_5$, $R_6$, and $R_7$ is, independently, hydrogen, halogen, hydroxyl, cyano, substituted or unsubstituted alkyl, substituted or unsubstituted haloalkyl, or substituted or unsubstituted alkoxy. In some embodiments, each $R_2$, $R_3$, $R_4$, $R_5$, $R_6$, and $R_7$ is, independently, hydrogen, halogen, substituted or unsubstituted alkyl, substituted or unsubstituted haloalkyl, or substituted or unsubstituted alkoxy. In some embodiments, each $R_2$, $R_3$, $R_4$, $R_5$, $R_6$, and $R_7$ is, independently, hydrogen, halogen, unsubstituted alkyl, unsubstituted haloalkyl, or unsubstituted alkoxy. In some embodiments, each $R_2$, $R_3$, $R_4$, $R_5$, $R_6$, and $R_7$ is, independently, hydrogen, F, Cl, methyl, —$CF_3$, or methoxy.

In some embodiments, n is an integer from 0 to 3. In some embodiments, n is an integer from 0 to 2. In some embodiments, n is 0 or 1.

In some embodiments, $R_1$ is hydrogen, unsubstituted alkyl, —$CF_3$, —$C_2F_5$, —$CHF_2$, —$CCl_3$, —$CHCl_2$, —$C_2Cl_5$, or —$CH_2CF_3$; n is an integer from 0 to 3; and each $R_2$, $R_3$, $R_4$, $R_5$, $R_6$, and $R_7$ is, independently, hydrogen, halogen, hydroxyl, cyano, substituted or unsubstituted alkyl, substituted or unsubstituted haloalkyl, or substituted or unsubstituted alkoxy.

In some embodiments, $R_1$ is hydrogen or unsubstituted alkyl; n is an integer from 0 to 2; and each $R_2$, $R_3$, $R_4$, $R_5$, $R_6$, and $R_7$ is, independently, hydrogen, halogen, substituted or unsubstituted alkyl, substituted or unsubstituted haloalkyl, or substituted or unsubstituted alkoxy.

In some embodiments, $R_1$ is hydrogen or methyl; n is 0 or 1; and each $R_2$, $R_3$, $R_4$, $R_5$, $R_6$, and $R_7$ is, independently, hydrogen, halogen, unsubstituted alkyl, unsubstituted haloalkyl, or unsubstituted alkoxy.

In some embodiments, $R_1$ is hydrogen or methyl; n is 0 or 1; and each $R_2$, $R_3$, $R_4$, $R_5$, $R_6$, and $R_7$ is, independently, hydrogen, F, Cl, methyl, —$CF_3$, or methoxy.

In some embodiments, each $R_1$, $R_2$, $R_3$, $R_4$, $R_5$, $R_6$, and $R_7$ is hydrogen; and n is 0.

In some embodiments, each $R_1$, $R_2$, $R_3$, $R_5$, and $R_7$ is hydrogen; each $R_4$ and $R_6$ is methyl; and n is 0.

In some embodiments, each $R_1$, $R_2$, $R_3$, $R_4$, $R_6$, and $R_7$ is hydrogen; $R_5$ is methoxy; and n is 0.

In some embodiments, each $R_1$, $R_2$, $R_3$, $R_4$, $R_5$, and $R_7$ is hydrogen; $R_6$ is —$CF_3$; and n is 0.

In some embodiments, each $R_1$, $R_2$, $R_3$, $R_4$, $R_6$, and $R_7$ is hydrogen; $R_5$ is fluorine; and n is 1.

In some embodiments, each $R_1$, $R_2$, $R_3$, $R_4$, $R_6$, and $R_7$ is hydrogen; $R_5$ is methoxy; and n is 1.

In some embodiments, each $R_1$, $R_2$, $R_3$, $R_4$, $R_6$, and $R_7$ is hydrogen; $R_5$ is chlorine; and n is 1.

In some embodiments, $R_1$ is methyl; each $R_2$, $R_3$, $R_4$, $R_5$, $R_6$, and $R_7$ is hydrogen; and n is 0.

In some embodiments, $R_1$ is methyl; each $R_2$, $R_3$, $R_4$, and $R_7$ is hydrogen; $R_5$ and $R_6$ are methyl; and n is 0.

The present disclosure also provides methods of restoring the tumor suppressor protein p53 signaling pathway within a tumor cell of a mammal comprising administering to the mammal in need thereof a compound of Formula II:

(II)

or a pharmaceutically acceptable salt thereof, wherein:
$R_1$ is hydrogen or a substituted or unsubstituted alkyl group;
each $R_2$, $R_3$, $R_4$, $R_5$, $R_6$, and $R_7$ is, independently, hydrogen, halogen, hydroxyl, substituted or unsubstituted alkyl, substituted or unsubstituted alkoxy, substituted or unsubstituted aryl, or substituted or unsubstituted amine;
X is sulfur, oxygen, or —NH; and
n is an integer from 0 to 5.

In some embodiments, $R_1$ is hydrogen or an unsubstituted alkyl. In some embodiments, $R_1$ is hydrogen or methyl. In some embodiments, $R_1$ is hydrogen.

In some embodiments, each $R_2$, $R_3$, $R_4$, $R_5$, $R_6$, and $R_7$ is, independently, hydrogen, halogen, hydroxyl, substituted or unsubstituted alkyl, substituted or unsubstituted alkoxy, substituted or unsubstituted aryl, or substituted or unsubstituted amine. In some embodiments, each $R_2$, $R_3$, $R_4$, $R_5$, $R_6$, and $R_7$ is, independently, hydrogen, halogen, or substituted or unsubstituted alkyl. In some embodiments, each $R_2$, $R_3$, $R_4$, $R_5$, $R_6$, and $R_7$ is, independently, hydrogen, halogen, or unsubstituted alkyl. In some embodiments, each $R_2$, $R_3$, $R_4$, $R_5$, $R_6$, and $R_7$ is, independently, hydrogen, halogen, or methyl.

In some embodiments, X is sulfur or oxygen. In some embodiments, X is sulfur.

In some embodiments, n is an integer from 0 to 3. In some embodiments, n is an integer from 0 to 2. In some embodiments, n is 1 or 2.

In some embodiments, $R_1$ is hydrogen or an unsubstituted alkyl; each $R_2$, $R_3$, $R_4$, $R_5$, $R_6$, and $R_7$ is, independently, hydrogen, halogen, hydroxyl, substituted or unsubstituted alkyl, substituted or unsubstituted alkoxy, substituted or unsubstituted aryl, or substituted or unsubstituted amine; X is sulfur or oxygen; and n is an integer from 0 to 3.

In some embodiments, $R_1$ is hydrogen or methyl; each $R_2$, $R_3$, $R_4$, $R_5$, $R_6$, and $R_7$ is, independently, hydrogen, halogen, or substituted or unsubstituted alkyl; X is sulfur or oxygen; and n is an integer from 0 to 2.

In some embodiments, $R_1$ is hydrogen; each $R_2$, $R_3$, $R_4$, $R_5$, $R_6$, and $R_7$ is, independently, hydrogen, halogen, or unsubstituted alkyl; X is sulfur; and n is 1 or 2.

In some embodiments, $R_1$ is hydrogen; each $R_2$, $R_3$, $R_4$, $R_5$, $R_6$, and $R_7$ is, independently, hydrogen, halogen, or methyl; X is sulfur; and n is 1 or 2.

In some embodiments, each $R_1$, $R_2$, $R_3$, $R_4$, $R_6$, and $R_7$ is hydrogen; $R_5$ is methyl; X is sulfur; and n is 2.

In some embodiments, each $R_1$, $R_2$, $R_3$, $R_4$, $R_6$, and $R_7$ is hydrogen; $R_5$ is chlorine; X is sulfur; and n is 2.

The present disclosure also provides methods of restoring the tumor suppressor protein p53 signaling pathway within a tumor cell of a mammal comprising administering to the mammal in need thereof a compound of Formula III:

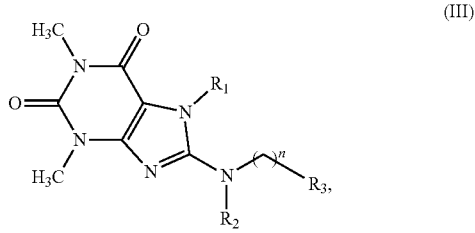

(III)

or a pharmaceutically acceptable salt thereof, wherein:

$R_1$ and $R_2$ are, independently, hydrogen or a substituted or unsubstituted alkyl;

$R_3$ is a substituted or unsubstituted heteroaryl; and n is an integer from 0 to 5.

In some embodiments, $R_1$ and $R_2$ are, independently, hydrogen or an unsubstituted alkyl. In some embodiments, $R_1$ and $R_2$ are, independently, hydrogen or methyl. In some embodiments, $R_1$ and $R_2$ are hydrogen.

In some embodiments, n is an integer from 0 to 3. In some embodiments, n is an integer from 0 to 2. In some embodiments, n is 1.

In some embodiments, $R_3$ is an unsubstituted heteroaryl. In some embodiments, $R_3$ is unsubstituted heteroaryl having from 3 to 10 ring-forming atoms. In some embodiments, $R_3$ is unsubstituted heteroaryl having from 3 to 6 ring-forming atoms. In some embodiments, $R_3$ is unsubstituted heteroaryl having from 3 to 5 ring-forming atoms. In some embodiments, $R_3$ is pyridyl, pyrimidinyl, pyrazinyl, pyridazinyl, pyridinyl, triazinyl, furyl, quinolyl, isoquinolyl, thienyl, imidazolyl, thiazolyl, indolyl, pyrryl, oxazolyl, benzofuryl, benzothienyl, pyrazolyl, benzthiazolyl, isoxazolyl, triazolyl, tetrazolyl, indazolyl, isothiazolyl, 1,2,4-thiadiazolyl, benzothienyl, purinyl, carbazolyl, isoxazolyl, benzimidazolyl, indolinyl, pyranyl, pyrazolyl, triazolyl, oxadiazolyl, thianthrenyl, indolizinyl, isoindolyl, isobenzofuranyl, pyrrolyl, benzoxazolyl, xanthenyl, 2H-pyrrolyl, 3H-indolyl, 4H-quinolizinyl, phthalazinyl, acridinyl, naphthyridinyl, quinazolinyl, phenanthridinyl, perimidinyl, phenanthrolinyl, phenazinyl, isothiazolyl, phenothiazinyl, isoxazolyl, or furazanyl. In some embodiments, $R_3$ is pyridyl, pyrimidinyl, pyrazinyl, pyridazinyl, pyridinyl, triazinyl, furyl, quinolyl, isoquinolyl, thienyl, imidazolyl, thiazolyl, indolyl, pyrryl, oxazolyl, purinyl, benzimidazolyl, indolinyl, pyranyl, pyrazolyl, triazolyl, oxadiazolyl, thianthrenyl, or pyrrolyl. In some embodiments, $R_3$ is 2-thienyl or 3-thienyl.

In some embodiments, $R_1$ and $R_2$ are, independently, hydrogen or an unsubstituted alkyl; n is an integer from 0 to 3; and $R_3$ is an unsubstituted heteroaryl.

In some embodiments, $R_1$ and $R_2$ are, independently, hydrogen or an unsubstituted alkyl; n is an integer from 0 to 3; and $R_3$ is unsubstituted heteroaryl having from 3 to 10 ring-forming atoms.

In some embodiments, $R_1$ and $R_2$ are, independently, hydrogen or methyl; n is an integer from 0 to 2; and $R_3$ is unsubstituted heteroaryl having from 3 to 6 ring-forming atoms.

In some embodiments, $R_1$ and $R_2$ are, independently, hydrogen or methyl; n is an integer from 0 to 2; and $R_3$ is unsubstituted heteroaryl having from 3 to 5 ring-forming atoms.

In some embodiments, $R_1$ and $R_2$ are hydrogen; n is an integer from 0 to 2; and $R_3$ is pyridyl, pyrimidinyl, pyrazinyl, pyridazinyl, pyridinyl, triazinyl, furyl, quinolyl, isoquinolyl, thienyl, imidazolyl, thiazolyl, indolyl, pyrryl, oxazolyl, benzofuryl, benzothienyl, pyrazolyl, benzthiazolyl, isoxazolyl, triazolyl, tetrazolyl, indazolyl, isothiazolyl, 1,2,4-thiadiazolyl, benzothienyl, purinyl, carbazolyl, isoxazolyl, benzimidazolyl, indolinyl, pyranyl, pyrazolyl, triazolyl, oxadiazolyl, thianthrenyl, indolizinyl, isoindolyl, isobenzofuranyl, pyrrolyl, benzoxazolyl, xanthenyl, 2H-pyrrolyl, 3H-indolyl, 4H-quinolizinyl, phthalazinyl, acridinyl, naphthyridinyl, quinazolinyl, phenanthridinyl, perimidinyl, phenanthrolinyl, phenazinyl, isothiazolyl, phenothiazinyl, isoxazolyl, or furazanyl.

In some embodiments, $R_1$ and $R_2$ are hydrogen; n is 1; and $R_3$ is pyridyl, pyrimidinyl, pyrazinyl, pyridazinyl, pyridinyl, triazinyl, furyl, quinolyl, isoquinolyl, thienyl, imidazolyl, thiazolyl, indolyl, pyrryl, oxazolyl, purinyl, benzimidazolyl, indolinyl, pyranyl, pyrazolyl, triazolyl, oxadiazolyl, thianthrenyl, or pyrrolyl.

In some embodiments, $R_1$ and $R_2$ are hydrogen; n is 1; and $R_3$ is 2-thienyl or 3-thienyl.

In some embodiments, $R_1$ and $R_2$ are hydrogen; $R_3$ is -2-thienyl; and n is 1.

In some embodiments, the cancer is a tumor suppressor protein p53 mutated associated cancer, a tumor suppressor protein Rb mutated associated cancer, a tumor suppressor protein NF1 mutated associated cancer, a tumor suppressor protein p16 mutated associated cancer, a tumor suppressor protein p27 mutated associated cancer, or a tumor suppressor protein VHL mutated associated cancer.

In some embodiments, the tumor suppressor protein p53 mutated associated cancer is breast cancer, pancreatic cancer, prostate cancer, lung cancer, liver cancer, oesophagus cancer, stomach cancer, binary tract cancer, head and neck cancer, bladder cancer, kidney cancer, mesothelioma, thyroid cancer, uterine cancer, ovarian cancer, brain cancer, lymphoma, myeloma, leukemia, or colon cancer.

In embodiments where the cancer is colon cancer, the colon cancer is colon adenocarcinoma, a mutated KRAS tumor, a mutated NRAS tumor, a mutated BRAF tumor, or a tumor with or without microsatellite instability.

The amount of compound to be administered may be that amount which is therapeutically effective. The dosage to be administered may depend on the characteristics of the subject being treated, e.g., the particular animal treated, age, weight, health, types of concurrent treatment, if any, and frequency of treatments, and on the nature and extent of the disease, condition, or disorder, and can be easily determined by one skilled in the art (e.g., by the clinician). The selection of the specific dose regimen can be selected or adjusted or titrated by the clinician according to methods known to the clinician to obtain the desired clinical response. In addition, in vitro or in vivo assays may optionally be employed to help identify optimal dosage ranges. The precise dose to be employed in the compositions may also depend on the route of administration, and should be decided according to the judgment of the practitioner and each patient's circumstances.

Suitable dosage ranges for oral administration include, but are not limited to, from about 0.001 mg/kg body weight to about 200 mg/kg body weight, from about 0.01 mg/kg body weight to about 100 mg/kg body weight, from about 0.01 mg/kg body weight to about 70 mg/kg body weight, from about 0.1 mg/kg body weight to about 50 mg/kg body weight, from 0.5 mg/kg body weight to about 20 mg/kg body weight, or from about 1 mg/kg body weight to about 10 mg/kg body weight. In some embodiments, the oral dose is about 5 mg/kg body weight.

Suitable dosage ranges for intravenous administration include, but are not limited to, from about 0.01 mg/kg body weight to about 500 mg/kg body weight, from about 0.1 mg/kg body weight to about 100 mg/kg body weight, from about 1 mg/kg body weight to about 50 mg/kg body weight, or from about 10 mg/kg body weight to about 35 mg/kg body weight.

Suitable dosage ranges for other routes of administration can be calculated based on the forgoing dosages as known by one skilled in the art. For example, recommended dosages for intradermal, intramuscular, intraperitoneal, subcutaneous, epidural, sublingual, intracerebral, transdermal, or inhalation are in the range from about 0.001 mg/kg body weight to about 200 mg/kg body weight, from about 0.01 mg/kg body weight to about 100 mg/kg body weight, from about 0.1 mg/kg body weight to about 50 mg/kg body weight, or from about 1 mg/kg body weight to about 20 mg/kg body weight. Effective doses may be extrapolated from dose-response curves derived from in vitro or animal model test systems. Such animal models and systems are well known in the art.

In some embodiments, the amount of the compound of Formula I administered to the mammal is from about 0.1 mg to about 500 mg. In some embodiments, the amount of the compound of Formula Ia administered to the mammal is from about 0.1 mg to about 500 mg. In some embodiments, the amount of the compound of Formula II administered to the mammal is from about 0.1 mg to about 500 mg. In some embodiments, the amount of the compound of Formula III administered to the mammal is from about 0.1 mg to about 500 mg.

Co-administration of the compositions described herein with other means of treatment is also contemplated. For example, a human in need of cancer treatment may also be administered radiation therapy, a chemotherapeutic agent, an immunotherapeutic agent, a lysosome inhibitor, or a calpain inhibitor, or any combination thereof.

In some embodiments, the chemotherapeutic agent is methotrexate, taxol, mercaptopurine, thioguanine, hydroxyurea, cytarabine, mitomycin, cyclophosphamide, ifosfamide, nitrosourea, cisplatin, carboplatin, oxaliplatin, nedaplatin, triplatin tetranitrate, phenanthriplatin, picoplatin, satraplatin, dacarbazine, procarbizine, an etoposide, a campathecin, bleomycin, doxorubicin, idarubicin, daunorubicin, dactinomycin, distamycin A, etidium, netropsin, auristatin, amsacrine, prodigiosin, bortexomib, pibenzimol, tomaymycin, duocarmycin SA, plicamycin, mitoxantrone, asparaginase, vinblastine, vincristine, MG132, tunicamycin, oligomycin, vinorelbine, paclitaxel, docetaxel, CPT-11, gleevec, erlotinib, gefitinib, ibrutinib, crizotinib, ceritinib, flavopiridol, gemcitabine, lapatinib, navitoclax, sorafenib, regorafenib, ganetespib, irinotecan, or 5-fluorouracil, or any combination thereof.

In some embodiments, a chemotherapeutic agent is also administered and the chemotherapeutic agent is CPT-11 or 5-fluorouracil.

In some embodiments, a lysosome inhibitor is also administered and the lysosome inhibitor is chloroquine.

In some embodiments, an immunotherapeutic agent is also administered and the immunotherapeutic agent is OPDIVO® (nivolumab), KEYTRUDA® (pembrolizumab), TECENTRIQ® (atezolizumab), IMFINZI® (durvalab), YERVOY® (ipilumumab), BAVENCTO® (avelumab), ERBITUX® (cetuxumab), AVASTIN® (bevacizumab), or HERCEPTIN® (trastuzumab), or any combination thereof.

In some embodiments, a calpain inhibitor is also administered and the calpain inhibitor is AK275, MDL28170, PD150606, SJA6017, ABT-705253, or SNJ-1945, or any combination thereof.

In some embodiments, the compound of Formula I, or its pharmaceutically acceptable salt, is administered prior to the radiation therapy or prior to administration of the chemotherapeutic agent, lysosome inhibitor, immunotherapeutic agent, or calpain inhibitor, or the compound of Formula I is administered after the radiation therapy or after administration of the chemotherapeutic agent, lysosome inhibitor, immunotherapeutic agent, or calpain inhibitor.

In some embodiments, the compound of Formula I, or its pharmaceutically acceptable salt, is administered concurrently with radiation therapy or concurrently with administration of the chemotherapeutic agent, lysosome inhibitor, immunotherapeutic agent, or calpain inhibitor.

In some embodiments, the compound of Formula Ia, or its pharmaceutically acceptable salt, is administered prior to the radiation therapy or prior to administration of the chemotherapeutic agent, lysosome inhibitor, immunotherapeutic agent, or calpain inhibitor, or the compound of Formula I is administered after the radiation therapy or after administration of the chemotherapeutic agent, lysosome inhibitor, immunotherapeutic agent, or calpain inhibitor.

In some embodiments, the compound of Formula Ia, or its pharmaceutically acceptable salt, is administered concurrently with radiation therapy or concurrently with administration of the chemotherapeutic agent, lysosome inhibitor, immunotherapeutic agent, or calpain inhibitor.

In some embodiments, the compound of Formula II, or its pharmaceutically acceptable salt, is administered prior to the radiation therapy or prior to administration of the chemotherapeutic agent, lysosome inhibitor, immunotherapeutic agent, or calpain inhibitor, or the compound of Formula I is administered after the radiation therapy or after administration of the chemotherapeutic agent, lysosome inhibitor, immunotherapeutic agent, or calpain inhibitor.

In some embodiments, the compound of Formula II, or its pharmaceutically acceptable salt, is administered concurrently with radiation therapy or concurrently with administration of the chemotherapeutic agent, lysosome inhibitor, immunotherapeutic agent, or calpain inhibitor.

In some embodiments, the compound of Formula III, or its pharmaceutically acceptable salt, is administered prior to the radiation therapy or prior to administration of the chemotherapeutic agent, lysosome inhibitor, immunotherapeutic agent, or calpain inhibitor, or the compound of Formula I is administered after the radiation therapy or after administration of the chemotherapeutic agent, lysosome inhibitor, immunotherapeutic agent, or calpain inhibitor.

In some embodiments, the compound of Formula III, or its pharmaceutically acceptable salt, is administered concurrently with radiation therapy or concurrently with administration of the chemotherapeutic agent, lysosome inhibitor, immunotherapeutic agent, or calpain inhibitor.

In some embodiments, the compound of Formula I, or its pharmaceutically acceptable salt, and the chemotherapeutic agent, lysosome inhibitor, immunotherapeutic agent, or calpain inhibit are present in the same pharmaceutical composition.

In some embodiments, the compound of Formula Ia, or its pharmaceutically acceptable salt, and the chemotherapeutic agent, lysosome inhibitor, immunotherapeutic agent, or calpain inhibit are present in the same pharmaceutical composition.

In some embodiments, the compound of Formula II, or its pharmaceutically acceptable salt, and the chemotherapeutic agent, lysosome inhibitor, immunotherapeutic agent, or calpain inhibit are present in the same pharmaceutical composition.

In some embodiments, the compound of Formula III, or its pharmaceutically acceptable salt, and the chemotherapeutic agent, lysosome inhibitor, immunotherapeutic agent, or calpain inhibit are present in the same pharmaceutical composition.

In some embodiments, there is a synergistic efficacy of compounds of Formula I and traditional chemotherapeutics CPT-11 and 5-FU.

In some embodiments, there may be a synergistic efficacy of compounds of Formula Ia and traditional chemotherapeutics CPT-11 and 5-FU.

In some embodiments, there may be a synergistic efficacy of compounds of Formula II and traditional chemotherapeutics CPT-11 and 5-FU.

In some embodiments, there may be a synergistic efficacy of compounds of Formula III and traditional chemotherapeutics CPT-11 and 5-FU.

The methods described herein, in addition to treating cancer, can also reduce cancer growth and/or progression, inhibit tumor growth, or prevent the spread or metastasis of cancer in a mammal comprising administering to the mammal in need thereof a therapeutically effective amount of a compound described herein or pharmaceutically acceptable salt thereof, or a pharmaceutical composition comprising the compound described herein or pharmaceutically acceptable salt thereof. In some embodiments, one or more compounds may be combined in the same composition for any of the methods disclosed herein.

The present disclosure also provides methods for killing or inhibiting growth of a cancer cell comprising contacting the cancer cell with an effective amount of a compound or pharmaceutically acceptable salt thereof, or a pharmaceutical composition comprising the compound or salt.

Thus, the compounds can be used as anti-cancer and anti-tumor agents, e.g., the compounds can kill or inhibit the growth of cancer cells. The compounds can also be used in methods of reducing cancer in an animal, or in methods of treating or preventing the spread or metastasis of cancer in an animal, or in methods of treating an animal afflicted with cancer. The compounds can also be used in methods of killing or inhibiting the growth of a cancer cell, or in methods of inhibiting tumor growth.

The compounds can be tested for anti-cancer activity by methods known to those of skill in the art. Examples of anti-cancer assays include, but are not limited to, standard cell viability assays, such as the XTT assay, or by metabolic activity assays.

Generally, cancer refers to any malignant growth or tumor caused by abnormal and uncontrolled cell division; it may spread to other parts of the body through the lymphatic system or the blood stream. Cancers include both solid tumors and blood-borne tumors.

Cancers that are treatable are broadly divided into the categories of carcinoma, lymphoma and sarcoma. Examples of carcinomas include, but are not limited to: adenocarcinoma, acinic cell adenocarcinoma, adrenal cortical carcinomas, alveoli cell carcinoma, anaplastic carcinoma, basaloid carcinoma, basal cell carcinoma, bronchiolar carcinoma, bronchogenic carcinoma, renaladinol carcinoma, embryonal carcinoma, anometroid carcinoma, fibrolamolar liver cell carcinoma, follicular carcinomas, giant cell carcinomas, hepatocellular carcinoma, intraepidermal carcinoma, intraepithelial carcinoma, leptomanigio carcinoma, medullary carcinoma, melanotic carcinoma, menigual carcinoma, mesometonephric carcinoma, oat cell carcinoma, squamal cell carcinoma, sweat gland carcinoma, transitional cell carcinoma, and tubular cell carcinoma. Sarcomas include, but are not limited to: ameliosblastic sarcoma, angiolithic sarcoma, botryoid sarcoma, endometrial stroma sarcoma, ewing sarcoma, fascicular sarcoma, giant cell sarcoma, granulositic sarcoma, immunoblastic sarcoma, juxaccordial osteogenic sarcoma, coppices sarcoma, leukocytic sarcoma (leukemia), lymphatic sarcoma (lympho sarcoma), medullary sarcoma, myeloid sarcoma (granulocitic sarcoma), austiogenci sarcoma, periosteal sarcoma, reticulum cell sarcoma (histiocytic lymphoma), round cell sarcoma, spindle cell sarcoma, synovial sarcoma, and telangiectatic audiogenic sarcoma. Lymphomas include, but are not limited to: Hodgkin's disease and lymphocytic lymphomas, such as Burkitt's lymphoma, NPDL, NML, NH and diffuse lymphomas.

Thus, examples of cancers that can be treated using the compounds described herein include, but are not limited to, Hodgkin's disease, non-Hodgkin's lymphomas, acute lymphocytic leukemia, multiple myeloma, breast carcinomas, ovarian carcinomas, lung carcinomas, Wilms' tumor, testicular carcinomas, soft-tissue sarcomas, chronic lymphocytic leukemia, primary macroglobulinemia, bladder carcinomas, chronic granulocytic leukemia, primary brain carcinomas, malignant melanoma, small-cell lung carcinomas, stomach carcinomas, colon carcinomas, malignant pancreatic insulinoma, malignant carcinoid carcinomas, malignant melanomas, choriocarcinomas, mycosis fungoides, head and neck carcinomas, osteogenic sarcoma, pancreatic carcinomas, acute granulocytic leukemia, hairy cell leukemia, rhabdomyosarcoma, Kaposi's sarcoma, genitourinary carcinomas, thyroid carcinomas, esophageal carcinomas, malignant hypercalcemia, renal cell carcinomas, endometrial carcinomas, polycythemia vera, essential thrombocytosis, adrenal cortex carcinomas, skin cancer, and prostatic carcinomas.

In some embodiments, the cancer is lung cancer (such as non-small cell lung cancer), breast cancer, prostate cancer, ovarian cancer, testicular cancer, colon cancer, renal cancer, bladder cancer, pancreatic cancer, glioblastoma, neuroblastoma, sarcomas such as Kaposi's sarcoma and Ewing's sarcoma, hemangiomas, solid tumors, blood-borne tumors, rhabdomyosarcoma, CNS cancer (such as brain cancer), retinoblastoma, neuroblastoma, leukemia, melanoma, kidney or renal cancer, and osteosarcoma.

The compounds can be used in methods of killing or inhibiting the growth of cancer cells, either in vivo or in vitro, or inhibiting the growth of a cancerous tumor.

The present disclosure also provides pharmaceutical packs or kits comprising one or more containers filled with one or more compounds of Formula I described herein. The present disclosure also provides pharmaceutical packs or kits comprising one or more containers filled with one or more compounds of Formula Ia described herein. The present disclosure also provides pharmaceutical packs or kits comprising one or more containers filled with one or more compounds of Formula II described herein. The present disclosure also provides pharmaceutical packs or kits comprising one or more containers filled with one or more compounds of Formula III described herein.

Optionally associated with such container(s) can be a notice in the form prescribed by a governmental agency regulating the manufacture, use or sale of pharmaceuticals or biological products, which notice reflects approval by the agency of manufacture, use or sale for human administration for treating a condition, disease, or disorder described herein. In some embodiments, the kit contains more than one compound described herein. In some embodiments, the kit comprises a compound described herein in a single injectable dosage form, such as a single dose within an injectable device such as a syringe with a needle.

The kits may further comprise a chemotherapeutic agent, a lysosome inhibitor, an immunotherapeutic agent, or calpain inhibitor.

In order that the subject matter disclosed herein may be more efficiently understood, examples are provided below. It should be understood that these examples are for illustrative purposes only and are not to be construed as limiting the claimed subject matter in any manner.

EXAMPLES

Example 1: Cell-Based Drug Screening for p53 Pathway-Restoring Small Molecules Materials and Methods High-throughput screening was performed using a non-invasive bioluminescence imaging in human colorectal cancer cell lines that stably express a p53-regulated luciferase reporter. Cells were seeded in 96-well plates (Greiner Bio-One) at a density of $1 \times 10^4$ cells per well. p53 transcriptional activity was imaged using an IVIS imaging system for a period of 3-4 hours.

Cell Lines and Culture Conditions

DLD-1, SW480, HCT116, and HCT116 p53$^{-/-}$ colorectal cancer cell lines that stably express a p53-regulated luciferase reporter were previously generated in our laboratory. RXF393 renal cancer cell lines, and WI38 and MRC5 normal lung cell fibroblasts were purchased from ATCC. Cell lines were maintained in HyClone™ Dulbecco's High Glucose Modified Eagles Medium (DMEM, GE Healthcare), HyClone™ McCoy's 5A (GE Healthcare), HyClone™ RPMI 1640 (GE Healthcare), or Eagle's Minimum Essential Medium (EMEM, ATCC) containing 10% fetal bovine serum and 1% penicillin/streptomycin (complete media) at 37° C. in 5% $CO_2$, as recommended by ATCC.

CellTiter-Glo® Luminescent Cell Viability Assay

Cells were seeded in 96-well plates at a density of $5 \times 10^3$ cells per well. 20 µL of CellTiter-Glo® Reagent was added directly to the wells, following the manufacturer's protocol, and bioluminescence signal was determined using an IVIS imaging system.

Knockdown Expression of p73, DR5, ATG5, and FADD Using siRNA

A total of $1 \times 10^5$ cells/well were plated per well in a 12-well plate in medium with 10% FBS without antibiotic. Forward transfection of p73 siRNA (s14319, Ambion®), DR5 (sc-40237, Santa Cruz Biotechnology), atg5 (137766, Ambion®), FADD (S16706, Ambion®) was performed using the Lipofectamine® RNAiMAX Transfection Reagent (Life Technologies) and incubated for 48 hours before treatment.

Overexpression of p53 R175H Mutant by Lentivirus Infection

HCT116 p53$^{-/-}$ cells (previously obtained from the Vogelstein Laboratory, Johns Hopkins University) were infected with a lentivirus vector containing the p53 R175H mutant (pLenti6/V5-p53_R175H, Addgene). Cells were selected with blasticidin (8 µg/mL) containing media cultured for 10 days. Blasticidin-resistant clones (pooled clones) were screened for expression of the p53 R175H mutation by Western blot analysis with p53 DO-1 antibody.

Knockdown Expression of NOXA by Lentivirus Infection

A NOXA shRNA plasmid construct was amplified according to the manufacturer's recommendation (TRC Lentiviral Human PMAIP1 shRNA, Dharmacon). Plasmid DNA was isolated using the PureLink® HiPure Plasmid Filter Maxiprep Kit (Invitrogen) according to the manufacturer's instructions. Lentivirus production was performed by transfecting HEK293T cells at a density of $8 \times 10^6$ cells per 10 cm dish with 1.6 µg pMD2.G envelope plasmid, 3.2 µg psPAX2 packaging vector, 3.2 µg plasmid DNA, and 24 µL of Lipofectamine® Transfection reagent 2000 (Life Technologies) in a total volume of reaction of 1 mL of antibiotic free DMEM media for a period of 6-10 hours. Media was then replaced with antibiotic free DMEM. Lentiviral particles were collected between 48-72 hours. SW480 cells ($2.3 \times 10^6$ cells per well in a 12-well plate) were infected 1:1 (virus containing media: antibiotic free DMEM media, total volume 1 mL) for a period of 24 hours. Then, media was replaced with DMEM complete media for an additional 24 hours. At this point, cells were split and seeded (20% confluent) for selection in a 10 cm dish with puromycin (2.5 µg/mL)-containing complete DMEM media and cultured for 10 days. Puromycin containing complete media was replaced every 2-3 days. Puromycin-resistant clones were screened for knockdown of NOXA by Western blot analysis with NOXA antibody.

Colony Formation Assay

Cells were seeded in 6-well plates at a density of 500 cells per well. Cells were treated with CB002 small molecule for 24 hours. Then, cells were cultured in drug-free complete media for 15 days. During the course of 15 days, the media was changed every 2-3 days. At the end of the two weeks, media was removed, wells were washed twice with Dulbecco's phosphate buffered saline (PBS) and the colonies were fixed and stained with 10% methanol and 0.25% crystal violet (Sigma-Aldrich) for 30 minutes. Wells were then carefully washed with distilled and deionized water and allowed to dry.

Apoptosis Assay

Apoptotic cells were quantified by sub-G1 analysis. Cells were seeded at a density of $2.5 \times 10^5$ to $5 \times 10^5$ in a 6-well plate and treated for 48-72 hours. After treatment, adherent cells were trypsinized and collected along with floating cells, washed with PBS and fixed in 70% ethanol. Cells were then incubated in a Phosphate-citric acid buffer (0.2 M $Na_2HPO_4$+0.1 M Citric Acid, pH 7.8) at room temperature for 5 minutes, spun down and resuspended for staining with 50 µg/mL propidium iodide (PI) in the presence of 250 µg/mL pancreatic ribonuclease (RNase A). Sub-G1 analyses were performed using an Epics Elite Epics flow cytometer (Coulter-Beckman).

Immunoblotting

After treatment, cells were harvested by trypsinization, washed with PBS, and lysed with RIPA buffer (Sigma-Aldrich) for 30 minutes to 1 hour at 4° C. Protein lysates were spun down and supernatant was collected. Protein quantification was performed using a Pierce™ BCA Protein Assay Kit (Thermo Fisher Scientific). 1×NuPAGE® LDS sample buffer (Thermo Fisher Scientific) and 2-Mercaptoethanol as the reducing agent (Sigma-Aldrich) were added to protein lysates, followed by boiling for 15 minutes at 95° C.

Equal total protein amounts samples were loaded into NuPAGE™ Novex™ 4-12% Bis-Tris Protein Gels (1.5 mm, Thermo Fisher Scientific) and gel eletrophoresis was performed with NuPAGE™ MES SDS Running Buffer. Proteins were transferred onto an Immobilon-P membrane (PVDF, EMD Millipore) using a Bio-Rad system with a 10% Tris-Glycine and 10% methanol transfer buffer diluted in distilled and deionized water. After transfer, membranes were blocked with 10% milk in TBST solution and then incubated overnight with primary antibody, washed with TBST and incubated with secondary antibody for 1 hour. Incubations were performed in 5% milk in TBST solution. Signal was detected by using a chemiluminescent detection kit, followed by autoradiography. The following antibodies were used: p53 (DO-1, 1:1000, Santa Cruz), p73 (1:1000, Bethyl Laboratories), p21 and NOXA (1:250, EMD Millipore), DR5, FADD, cleaved caspase 3, cleaved caspase 8, cleaved PARP, and LC3B (1:1000, Cell Signaling), and β-actin (1:10000, Sigma).

Statistical Analysis

Data are presented as means±SEM (three biological replicates). To assess the statistical significance of the differences, Two-way ANOVA for two comparisons was performed, with $p<0.05$ defined as statistically significant. Comparisons were made against the DMSO vehicle control.

Bioluminescence Assay

Cell-based screening of p53 transcriptional activity for small molecule CB002 was accomplished using noninvasive bioluminescence imaging in human colorectal cancer cell lines SW480, DLD-1, DLD-1 p73$^{-/-}$, HCT116, and HCT116 p53$^{-/-}$. These cell lines stably express a p53 reporter, PG13-luc. Cells were seeded in opaque 96-well culture at a density of $5\times10^4$ cells/well. The cells were treated with CB002 at ranging doses with DMSO controls. Bioluminescence in cells was imaged for p53 transcriptional activity at 2 hours and 24 hours using IVIS imaging system (Xenogen).

Cell Titer-Glo luminescent Cell viability assay

Cell lines at a concentration of $4\times10^3$ cells/well were seeded out on an opaque 96-well plate and treated with CB002 and Analog 11 in ranging doses starting from 200 μmol/L with DMSO controls. At 72 hours after treatment, cells were mixed with 30 μL Cell Titer-Glo reagent and after ten minutes of room temperature incubation were imaged using IVIS imaging system (Xenogen).

FACS Assay

Cells were seeded out at $1\times10^6$ cells/well on six well plates and treated with CB002 and Analog 11 at ranging doses with DMSO controls. Cells were harvested after 72 hours of treatment, all cells including floating cells were fixed with ethanol and stained with Propidium Iodide and then analyzed using Epics Elite flow cytometer to measure the DNA content of the stained cells.

Western Immunoblot Analysis

Proteins were isolated using NP40 Lysis Buffer (20 mmol/L Tris-HCl (pH 7.4), 150 mmol/L NaCl, 5 mmol/L EDTA, 50 mmol/L NaF, 1 mmol/L glycerophosphate, 5 mmol/L $Na_4P_2O_7$, 0.5% NP40, and complete protease inhibitor cocktail (Roche)) and electrophoresed through 4-12% SDS-PAGE followed by semi-dry transfer to PVDF membranes. The PVDF membranes were incubated with different antibodies including p21 (OP64-100UG, EMD Millipore (world wide web at emdmillipore.com/US/en/product/Antip21WAF1-(Ab-1)-Mouse-mAb-(EA10), EMD_BIO-OP64)), PUMA (12450S, Cell Signaling Technology, world wide web at cellsignal.com/products/primary-antibodies/puma-d30c10-rabbit-mab/12450), DR5 (3696S, Cell Signaling Technology, world wide web at cellsignal.com/products/primary-antibodies/dr5-antibody/3696?N=4294956287&Ntt=3696s&fromPage=plp&requestid=541668), p53(sc-126, Santa Cruz, world wide web at scbt.com/scbt/fr/product/p53-antibody-do-1), and RAN (610341, BD Transduction Laboratories, world wide web at bdbiosciences.com/us/reagents/research/antibodies-buffers/cell-biologyreagents/cell-biology-antibodies/purified-mouse-anti-ran-20ran/p/610341) in blocking buffer at 4° C. overnight. Bound antibody will be detected using IRDye secondary antibodies (LI-COR Biosciences,) in Odyssey blocking buffer for 1 hour then imaged using the ODYSSEY infrared imaging system.

Example 2: CB002 Restores p53-Dependent Transcriptional Reporter Activity

In order to identify small molecules that could restore the p53 signaling pathway, 50,000 small molecules from the Chembridge Library were screened using a firefly luciferase human p53 reporter assay system. SW480 colorectal cancer cells that stably express the human p53 reporter were treated with compounds at various concentrations from 0-100 μM for 2 and 24 hours. This initial screen identified CB002 (ID 7745998, IUPAC name: 8-anilino-1,3-dimethyl-3,7-dihydro-1H-purine-2,6-dione) as a small molecule capable of activating the luciferase reporter in a dose-dependent manner. To further validate the effects of CB002, the screening was expanded by testing effects on p53-dependent reporter activity in DLD-1, wild-type HCT116, and p53-null colorectal cancer HCT116 cell lines. In all three cell lines tested the activity of the reporter was induced in a dose-dependent manner at 3 and 24 hours (see, FIG. 1). Referring to FIG. 1, representative images of luciferase-based p53-reporter activity assays are shown at 3 hours (Panel A). Quantification of the luciferase-based p53-reporter activity assays in three different cell lines incubated from 3-24 hours with CB002 are shown (Panels B-D). p53-reporter activity assays are shown at 2 hours for HCT116 p53-null cells (Panel E). Three replicates were performed for each concentration of CB002 as indicated in the figure panels. These results document that CB002 restores the p53-dependent transcriptional activity of a reporter gene.

Example 3: A Favorable Therapeutic Index is Observed with CB002 Using Human Tumor and Normal Cell Lines To begin establishing the potential of CB002 as a candidate therapeutic agent, its therapeutic index was determined by treating cancer (DLD-1, SW480, and RXF393) and normal (WI38 and MRC5) cell lines with concentrations of CB002 ranging from 0-500 μM for a period of 72 hours and assessing cell viability by the CellTiter-Glo® luminescence assay (see, FIG. 2). $IC_{50}$ values were determined using GraphPad analyses and are listed in Table 1. CB002 has a significant therapeutic index among the cells tested. Normal cell lines have an $IC_{50}$ value of approximately 650 μM while in the panel of cancer cell lines tested $IC_{50}$ values ranged from 96 μM-400 μM. SW480 was observed to be the most sensitive cell line, followed by DLD-1, and RXF393 is the least sensitive.

TABLE 1

Figure 2:
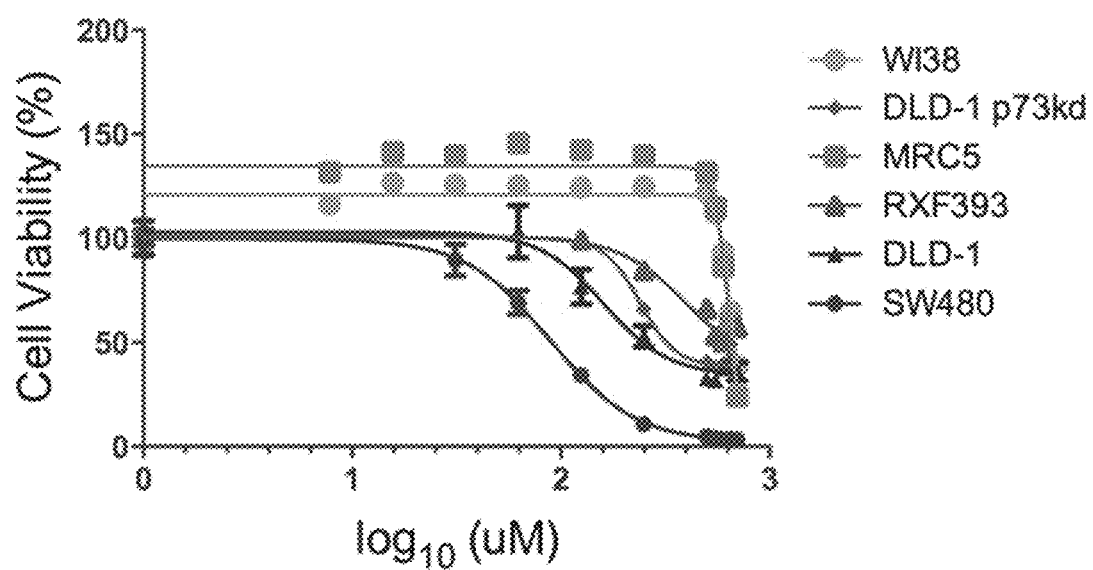
FIG. 2 shows CB002 has a favorable therapeutic index in cancer cell lines.

CB002 IC$_{50}$ values determined using GraphPad analyses
for the cell lines tested in FIG. 2

| Cell Line | IC$_{50}$ (μM) | 95% CI | R$^2$ |
|---|---|---|---|
| SW480 | 96.47 | 82.92-96.52 | 0.991 |
| DLD-1 | 161.1 | 135.8-190.0 | 0.946 |
| DLD-1 p73kd | 239.7 | 230.2-249.6 | 0.992 |
| RXF393 | 399.5 | 259.4-615.5 | 0.928 |
| MRC5 | 647.0 | 578.3-723.8 | 0.906 |
| WI38 | 641.7 | 606.6-678.9 | 0.921 |

Figure 3:
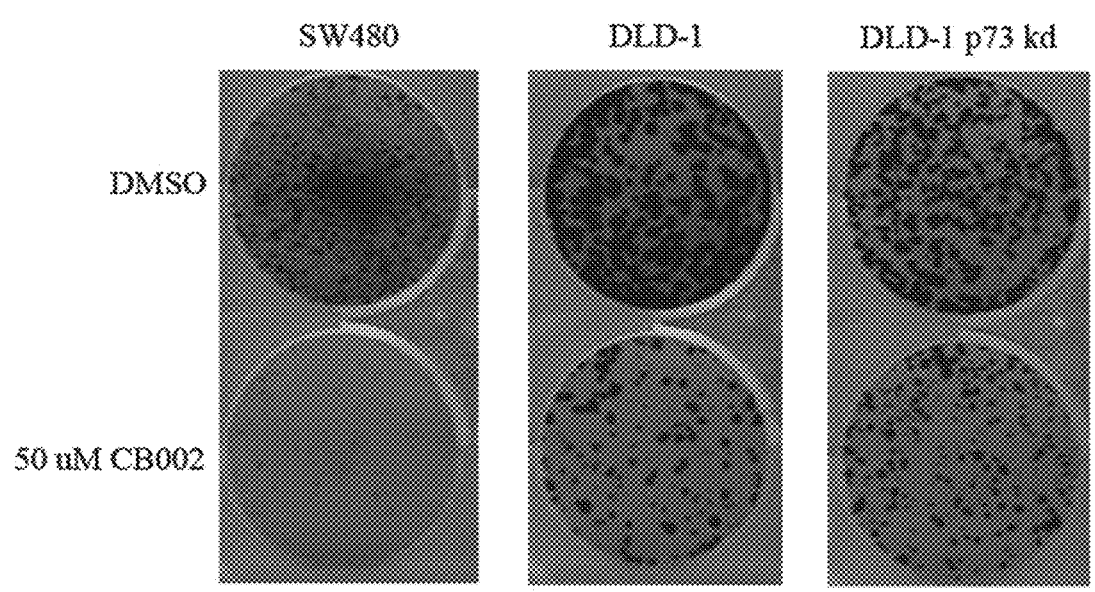
FIG. 3 shows CB002 qualitatively decreases colony formation in SW480, DLD-1, and DLD-1 stable p73 knockdown colorectal cancer cell lines.

Example 4: CB002 Qualitatively Decreases Colony Formation by Colorectal Cancer Cell Lines To further validate CB002 as a candidate therapeutic, its capability to affect cell growth was determined by analyzing cancer cell colony formation. Colony formation assays are widely used to determine the ability of a single cell to proliferate and form a colony in culture. This method offers the advantage of elucidating the sensitivity of cells towards cytotoxic agents in a long-term assay that may mimic the response seen in mouse models. CB002 was observed to significantly decreases colony formation in SW480, DLD-1, and p73 DLD-1 stable knockdown cells (see, FIG. 3). Referring to FIG. 3, cells were treated with 50 μM of CB002 for a period of 24 hours, at which point media was replaced with complete media for a period of 15 days. Images are from one of three replicates. These results suggest that CB002 has cytotoxic effects against human cancer cells in a long-term assay and that the effects may not depend on p73.

Example 5: CB002 Induces Apoptotic Cell Death of Tumor Cells

Figure 4:
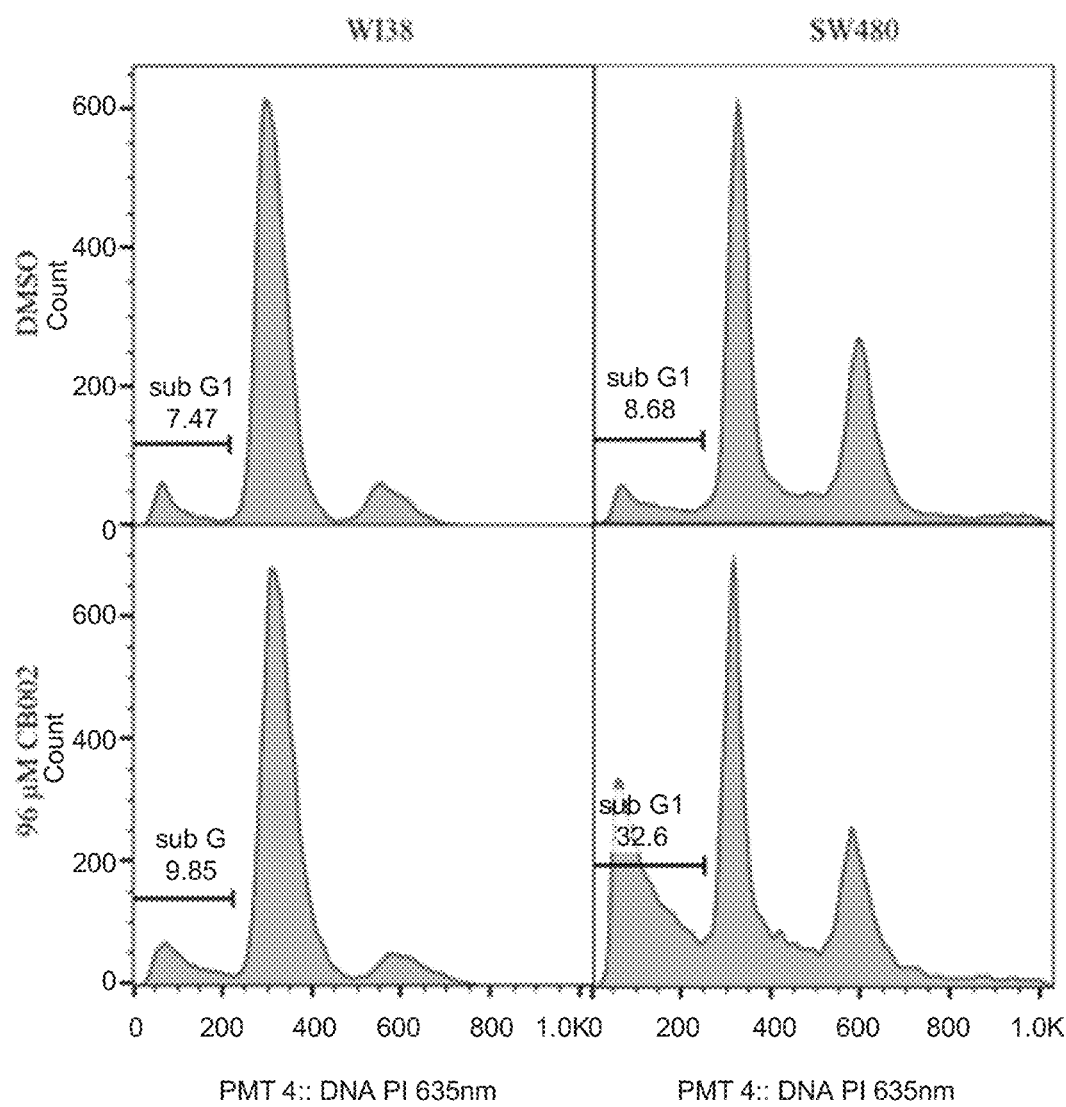
FIG. 4 shows CB002 treatment for 48 hours increases apoptotic cells as indicated by the sub-G1 content in SW480 cancer cells but not in normal WI38 cells.
Figure 4:
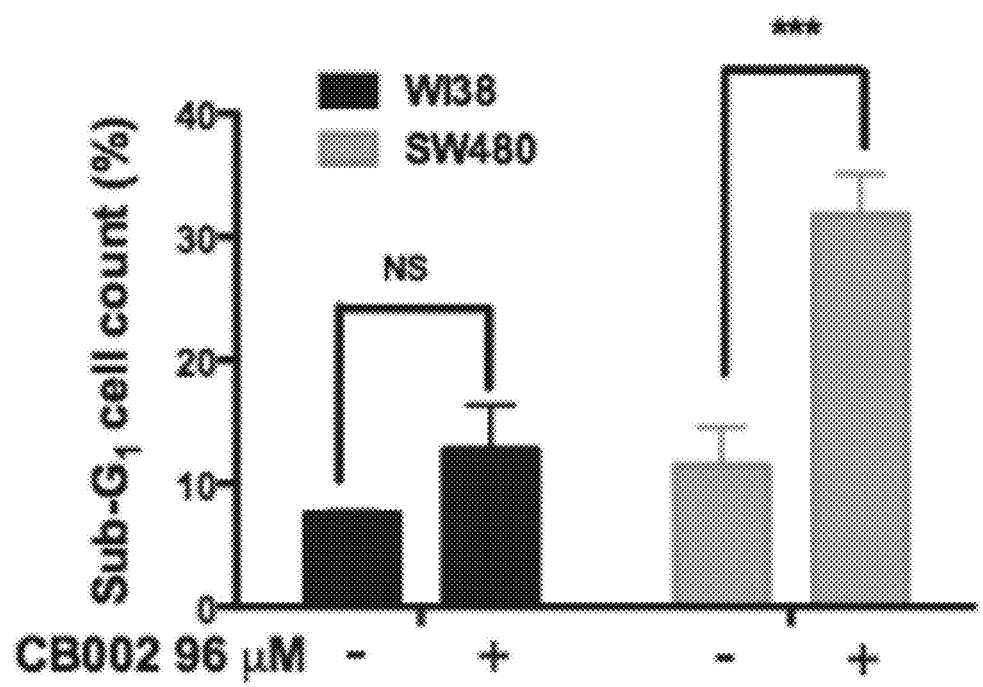

To determine whether CB002 promotes cancer cell death through apoptosis, SW480 cells were treated for 48 hours and subjected to sub-G1 analyses. Referring to FIG. 4, a two-way ANOVA statistical analysis was performed, with $p<0.05$ against DMSO vehicle control. Three replicates were performed, and a representative histogram is shown. SW480 DMSO vehicle control sub-G1 population was 8.7% whereas treatment with 96 μM CB002 showed a population of 32.6% (see, FIG. 4, right panels). This significant increase in sub-G1 content upon CB002 treatment indicates an augmentation in apoptotic cells. Furthermore, 96 μM CB002 treated WI38 normal cells showed a sub-G1 population of 9.8% as compared to the DMSO control where the sub-G1 content was 7.6% (see, FIG. 4, left panels). The increase in Sub-G1 population in WI38 cells was determined not to be statistically significant (see, FIG. 4, bottom panel). Thus, CB002 induces cell death through apoptosis specifically in cancer cell lines but not in normal cells.

Figure 5:
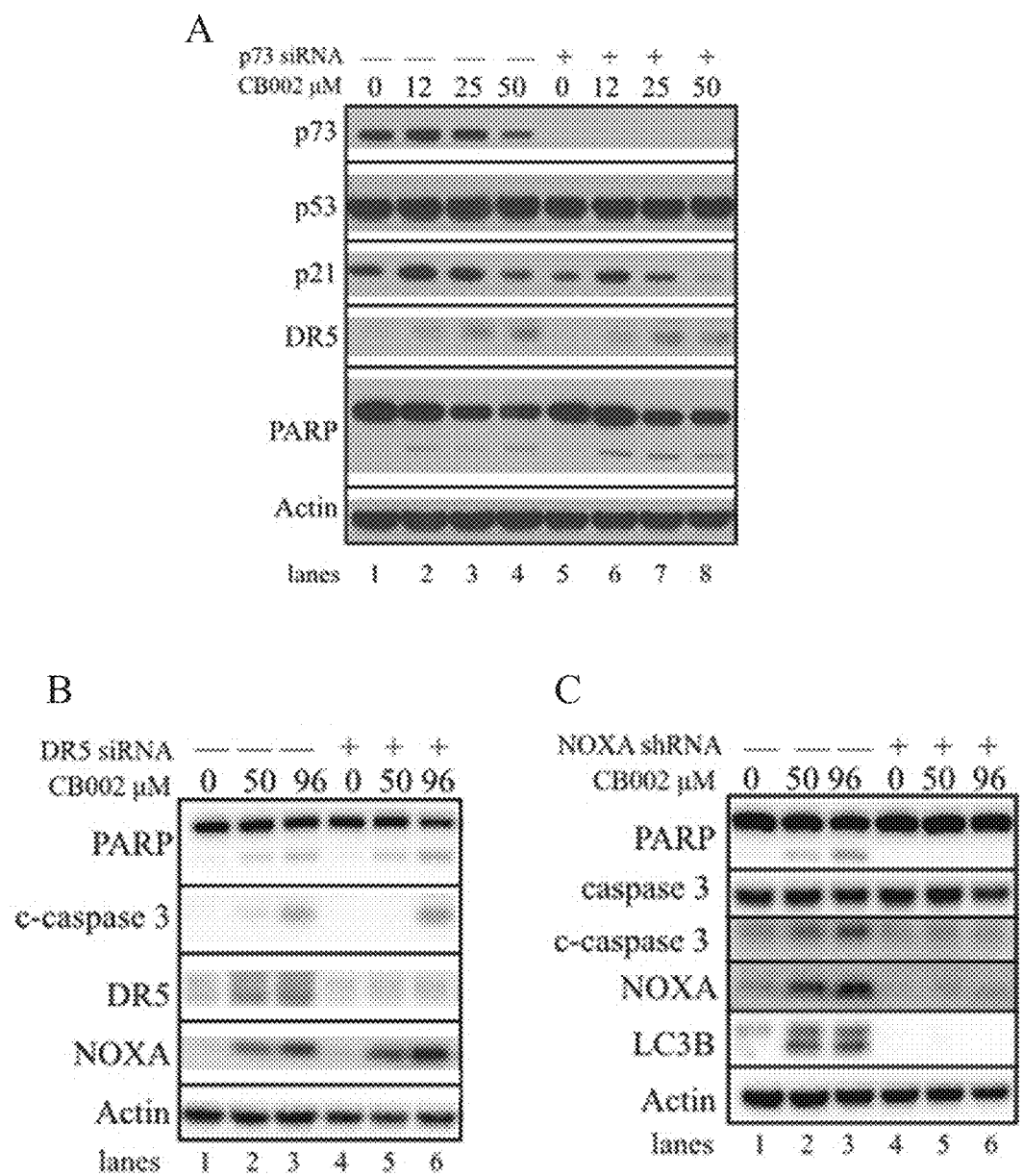
FIG. 5 (Panels A-E) shows CB002 induces expression of p53 target genes independently of p73 and NOXA is required for CB002-mediated apoptosis.
Figure 5:
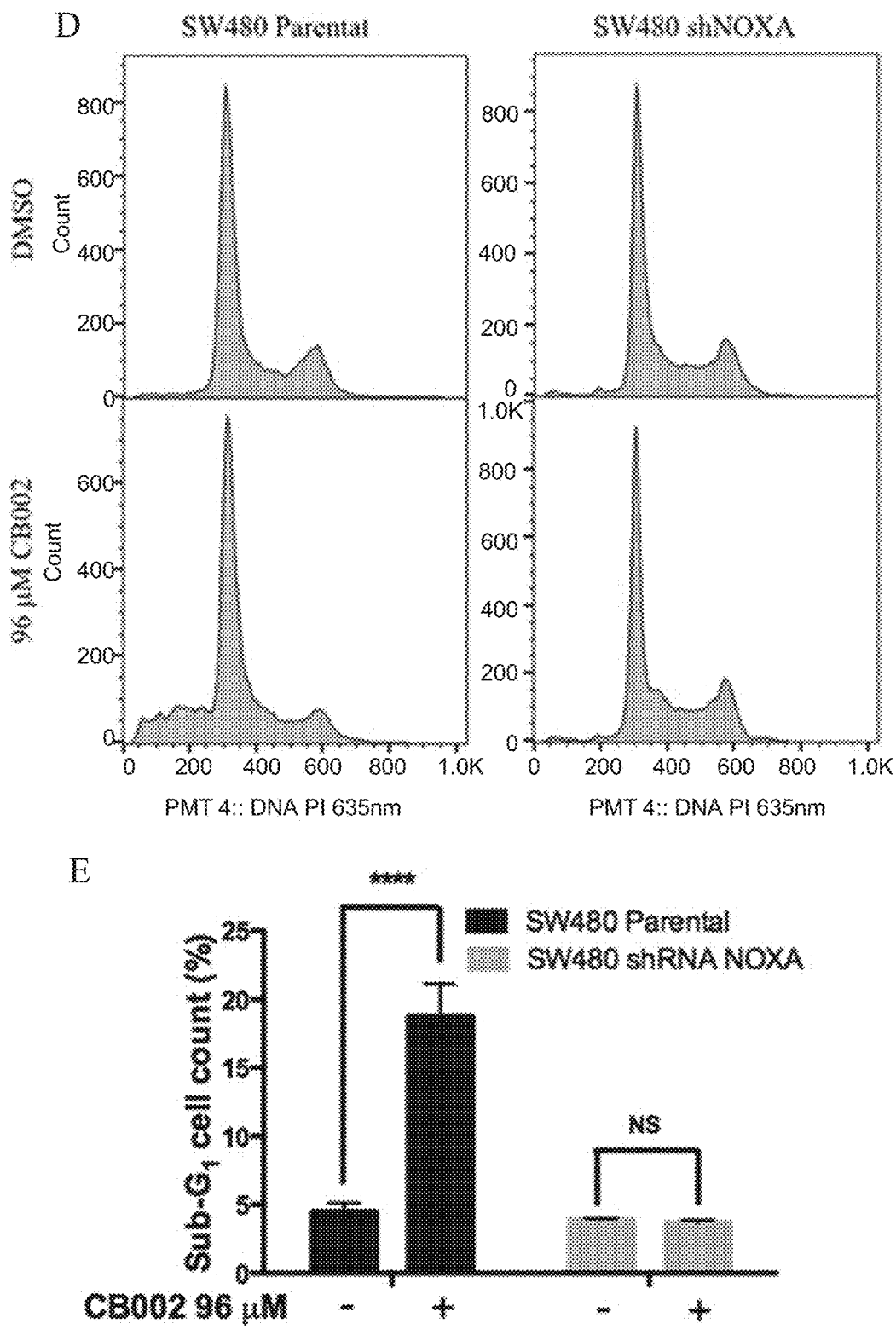

Example 6: CB002 Induces the Expression of Endogenous p53 Target Genes in Mutant p53-Expressing Tumor Cells and Apoptotic Cell Death To further investigate the potential of CB002 as a p53 pathway-restoring compound, various cancer cell lines were treated and probed for expression of endogenous p53 target genes, as well as for markers of apoptotic cell death. SW480 cells were treated with DMSO, 12, 25, and 50 μM CB002 as concentrations below the IC$_{50}$ value. Referring to FIG. 5, whole cell lysates were subjected to Western blot analysis. p73 was knocked-down by siRNA in SW480 cells followed by CB002 treatment for 16 hours (Panel A). DR5 was knocked-down by siRNA in DLD-1 cells followed by CB002 treatment for 16 hours (Panel B). NOXA was knocked-down by shRNA in SW480 cells followed by CB002 treatment for 16 hours (Panel C). Parental SW480 and SW480 NOXA stable knockdown cells treated with CB002 for 48 hours were subjected to a sub-G1 analysis (Panels D and E). A two-way ANOVA statistical analysis was performed for results from Panel D, $p<0.05$ against DMSO vehicle control (Panel E). Three replicates were performed, and a representative histogram is shown. c-caspase 3 corresponds to the cleaved form of full-length caspase-3.

As shown in FIG. 5, panel A, CB002 was found to increase the expression of proteins involved in p53-dependent cell cycle arrest and apoptosis, including p21 and DR5 (compare lane 1 to 2, 3, and 4). NOXA, a pro-apoptotic protein, was found to be increased by CB002 concentrations below the IC$_{50}$ (50 μM) and at the IC$_{50}$ (96 μM) in SW480 cells (see, FIG. 5, panel B, compare lane 1 to 2, and 3). Altogether, these data indicate that the p53 pathway is activated by CB002 as demonstrated by the induction of endogenous p53 target genes.

To validate that cell death was mediated through apoptosis, PARP cleavage was further assessed. Upon CB002 treatment, cleaved PARP expression was observed to increase upon CB002 treatment as compared to vehicle control (see, FIG. 5, panel A, compare lane 1 to 2, 3, and 4). Taken together, these data indicate that CB002 induces the expression of p53 target genes and cell death in the SW480 cell line. Similar results were observed in DLD-1 cells (data not shown). To further investigate the mechanism of CB002 in restoring the p53 pathway, p73 protein expression was efficiently knocked down (see, FIG. 5, panel A, see lanes 5-8) and p53 target gene expression was assessed.

CB002 treatment was found to increase the expression of p53 target genes p21 and DR5, and associated PARP cleavage in p73-knockdown cells (see, FIG. 5, panel A, compare lane 5 to 6, 7, and 8). Overall these data suggest that p73 may not play a critical role in the mechanism of CB002 p53 pathway restoration or cell death. In addition, CB002 treatment groups showed constant p53 protein expression levels as the DMSO control (see, FIG. 5, panel A, compare lane 1 to 2, 3, and 4). This indicates that CB002 might not have an effect on mutant p53 protein expression in SW480 cells. Nonetheless, further experiments were performed to corroborate this finding suggest some degradation effects towards certain p53 mutants (refer to FIG. 6 section).

Example 7: NOXA Protein is Required for CB002-Induced Cell Death of Tumor Cells To determine the role of p53 target genes DR5 and NOXA in CB002-mediated cell death, DR5 was knocked down by siRNA and a SW480 cell line stably transfected with NOXA shRNA plasmid construct was generated. Adequate DR5 knockdown was achieved as shown in FIG. 5, panel B (refer to lanes 4-6). DR5 knockdown in SW480 cells treated with 50 and 96 μM CB002 continued to induce the expression of cleaved caspase 3 (c-caspase 3) and cleaved PARP (see, FIG. 5, panel B, compare lane 4 to 5 and 6) as efficiently as the scrambled siRNA-treated cells (see, FIG. 5, panel B, compare lanes 2 and 3 to 5 and 6). Therefore, DR5 appears dispensable for CB002-mediated cell death in the tumor cell lines that were tested.

By contrast, when NOXA was efficiently knocked down (see, FIG. 5, panel B, lanes 4-6), 50 and 96 µM CB002 treatment did not induce the expression of apoptotic markers c-caspase 3 and cleaved PARP (see, FIG. 5, panel B, lanes 5-6). The requirement for NOXA in tumor cell apoptosis induction after exposure to CB002 was verified by conducting sub-G1 analyses. As expected, 96 µM CB002 treatment in parental SW480 cells caused an increase in sub-G1 content (19%) as compared to DMSO treatment (4.5%). Nonetheless, 96 µM CB002 treatment in SW480 where NOXA was stably knockeddown, failed to increase the content of sub-G1 cells (3.7%) when compared to DMSO treatment (3.93%) (see, FIG. 5, panels D and E). These data denote NOXA as the primary mediator in the mechanism of action of CB002-mediated cell death, in the tumor cell lines tested under the described experimental conditions.

In addition to CB002 increasing the expression of apoptotic markers, it was found to induce the expression of LC3B, a marker of autophagy (see, FIG. 5, panel C, compare lane 1 to 2 and 3). NOXA knock-down cells treated with 50 and 96 µM CB002 failed to induce LC3B expression (see, FIG. 5, panel C, lanes 5 and 6), indicating that NOXA is required for autophagy induction. The role of autophagy is further addressed below (see, FIG. 8).

Example 8: CB002 Treatment of Tumor Cells Destabilizes the R175H p53 Mutant

Figure 6:
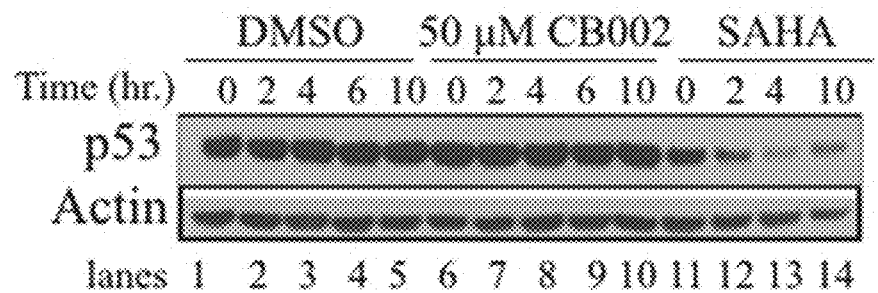
FIG. 6 (Panels A-C) shows CB002 does not reduce mutant p53 stability in SW480 and DLD-1 cells.
Figure 6:
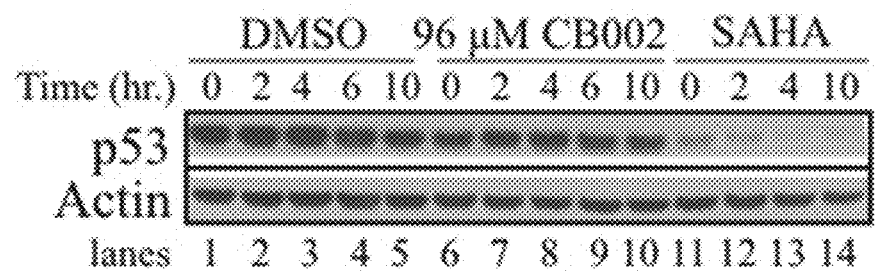
Figure 6:
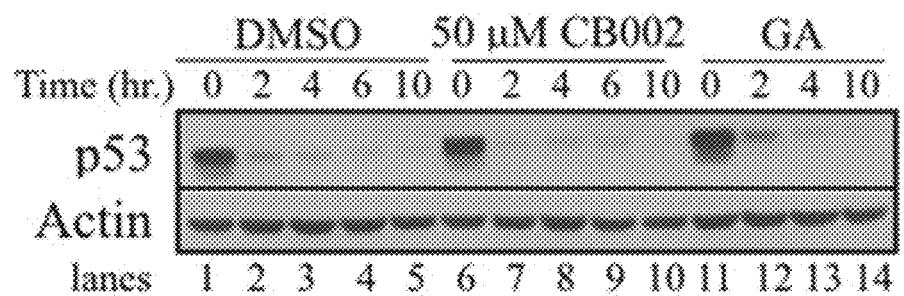

As mutant p53 can acquire a gain-of-function activity, targeting mutant p53 for degradation has been explored as a therapeutic strategy. To investigate the capability of CB002 to impact on mutant p53 protein expression, Western blot analysis was used. CB002 treatments showed no alteration in p53 protein expression levels with the DMSO control (see, FIG. 5, panel A, compare lane 1 to 2, 3, and 4). To confirm these findings, a cycloheximide chase assay was performed. Cells were treated with vehicle control or CB002 for a period of 24 hours. Subsequently, 100 µg/mL cycloheximide was added to the wells and protein lysates were collected at different time points between 0-10 hours. CB002 treatment did not affect mutant p53 stability in SW480 and DLD-1 cells (see, FIG. 6, compare lanes 1-5 to 6-10). Referring to FIG. 6, experiments with SW480 cells (Panels A and B) and analysis of DLD-1 colorectal cancer cells (Panel C) are shown. Cells were treated for a 24 hour period with DMSO, CB002 or positive control followed by 100 µg/mL of cycloheximide addition, and protein stability was evaluated in a time course ranging from 0-10 hours. Histone deacetylase inhibitor, SAHA and Hsp90 inhibitor Geldanamycin (1 µM GA) were used as positive controls.

Figure 7:
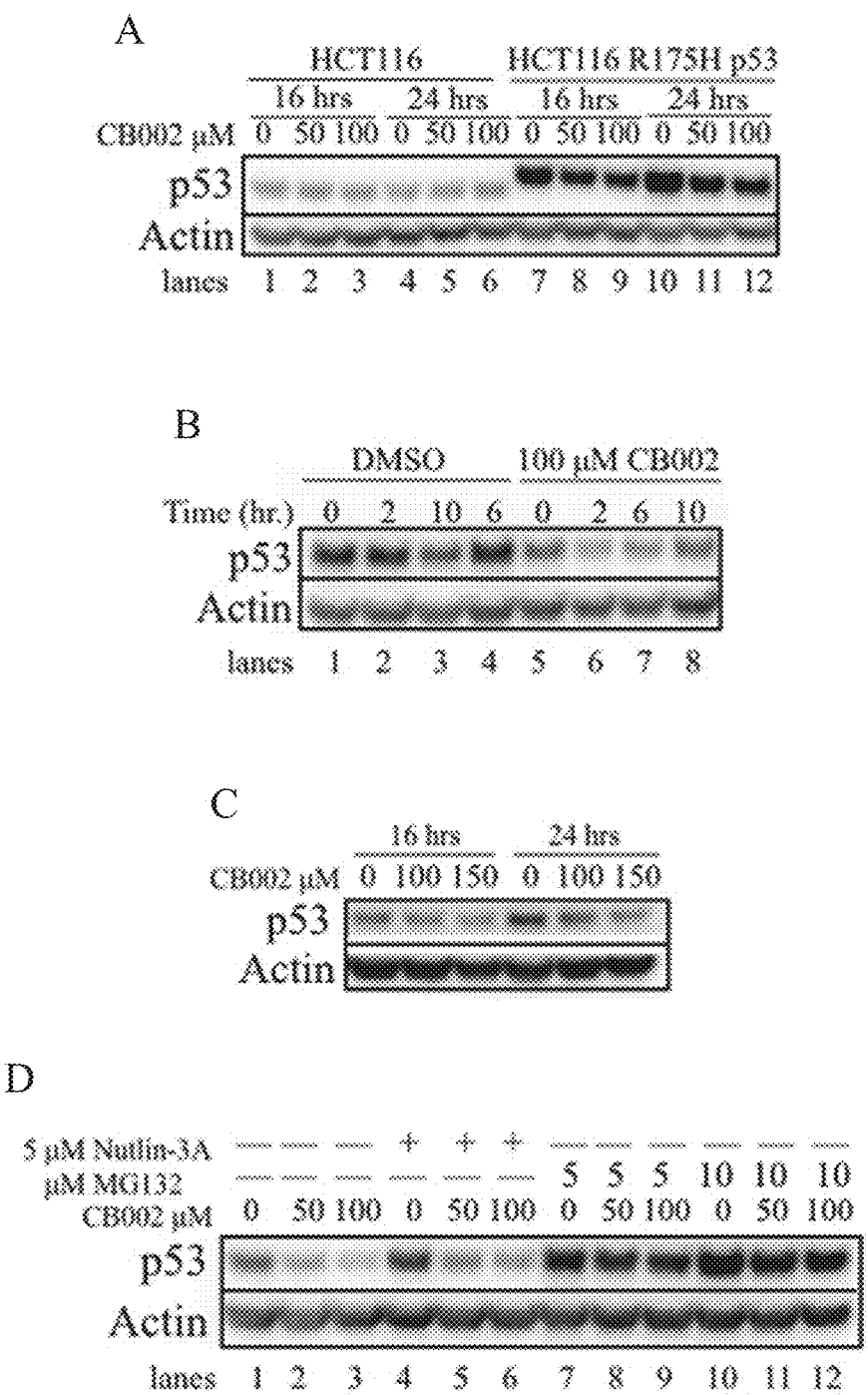
FIG. 7 (Panels A-D) shows CB002 treatment reduces the stability of the R175H p53 mutant.

CB002 treatment at 50 and 100 µM in HCT116 p53-null cells that exogenously expressed the R175H p53 mutant showed a decrease in mutant p53 protein expression compared to the DMSO control at 16 and 24 hours (see, FIG. 7, panel A, compare lanes 7 to 8 and 9, and 10 to 11 and 12). To validate this result, a cycloheximide chase experiment was performed, as shown in FIG. 7, panel B. Using 100 µM CB002 treatment decreased the stability of mutant p53 compared to the vehicle control (see, FIG. 7, panel B, compare lanes 1-4 to 5-8). To investigate that the data observed was not an effect that is specific for exogenously expressed protein, RXF393 renal cancer cells that endogenously express R175H p53 were treated with 100 and 150 µM CB002. Both concentrations of CB002 at 16 and 24 hours were found to decrease R175H p53 mutant expression as compared to the vehicle control (see, FIG. 7, panel C). Altogether, the data suggests that CB002 is capable of decreasing mutant p53 expression but potentially in a mutation-selective manner. In addition, CB002 p53 degradation was specific to mutant p53 as it was unable to decrease the expression of wild-type p53 (see, FIG. 7, panel A, lanes 1-6).

Referring to FIG. 7, CB002 reduced the protein expression of the exogenous R175H mutant in HCT116 p53-null cells and not the HCT116 wild-type p53 cells (Panel A). HCT116 R175H p53 cells were treated for 24 hours with DMSO or CB002 followed by 100 µg/mL cycloheximide addition. Protein stability was evaluated from 0-10 hours (Panel B). CB002 reduced the protein expression of the endogenous R175H mutant p53 in RXF393 renal cancer cells (Panel C). Co-treatment for 24 hours with proteasome inhibitor MG132 and CB002 rescued the expression of the R175H mutant p53, suggesting the involvement of the ubiquitin proteasome system in CB002-mediated mutant p53 degradation (Panel D).

Example 9: CB002-Dependent R175H Mutant p53 Degradation in Tumor Cells is Rescued by MG132

Mutant p53 can be degraded by various mechanisms including via MDM2-mediated degradation through the ubiquitin proteasome system. In order to explore the route by which the R175H p53 mutant was being degraded in response to CB002, HCT116 p53 R175H cells were pre-treated with the MDM2 inhibitor Nutlin-3A and the proteasome inhibitor MG132 prior to CB002 treatment. After 1 hour of incubation, cells were simultaneously treated with CB002 and Nutlin-3A or MG132. Co-treatment using 50 or 100 µM CB002 along with Nutlin-3A for 24 hours still resulted in reduction of R175H p53 mutant protein expression (see, FIG. 7, panel D, compare lane 4 to 5 and 6). These results suggest that MDM2 may not be required for the decreased R175H mutant p53 stability in the presence of CB002. On the other hand, treatment with CB002 and two different concentrations of MG132 (5 and 10 µM) appeared to rescue R175H mutant p53 protein expression (see, FIG. 7, compare lanes 7 to 8 and 9, and 10 to 11 and 12). The data suggest that the R175H mutant p53 protein is degraded in human cancer cells in response to CB002 in a manner that is dependent on the ubiquitin proteasome system.

Figure 8:
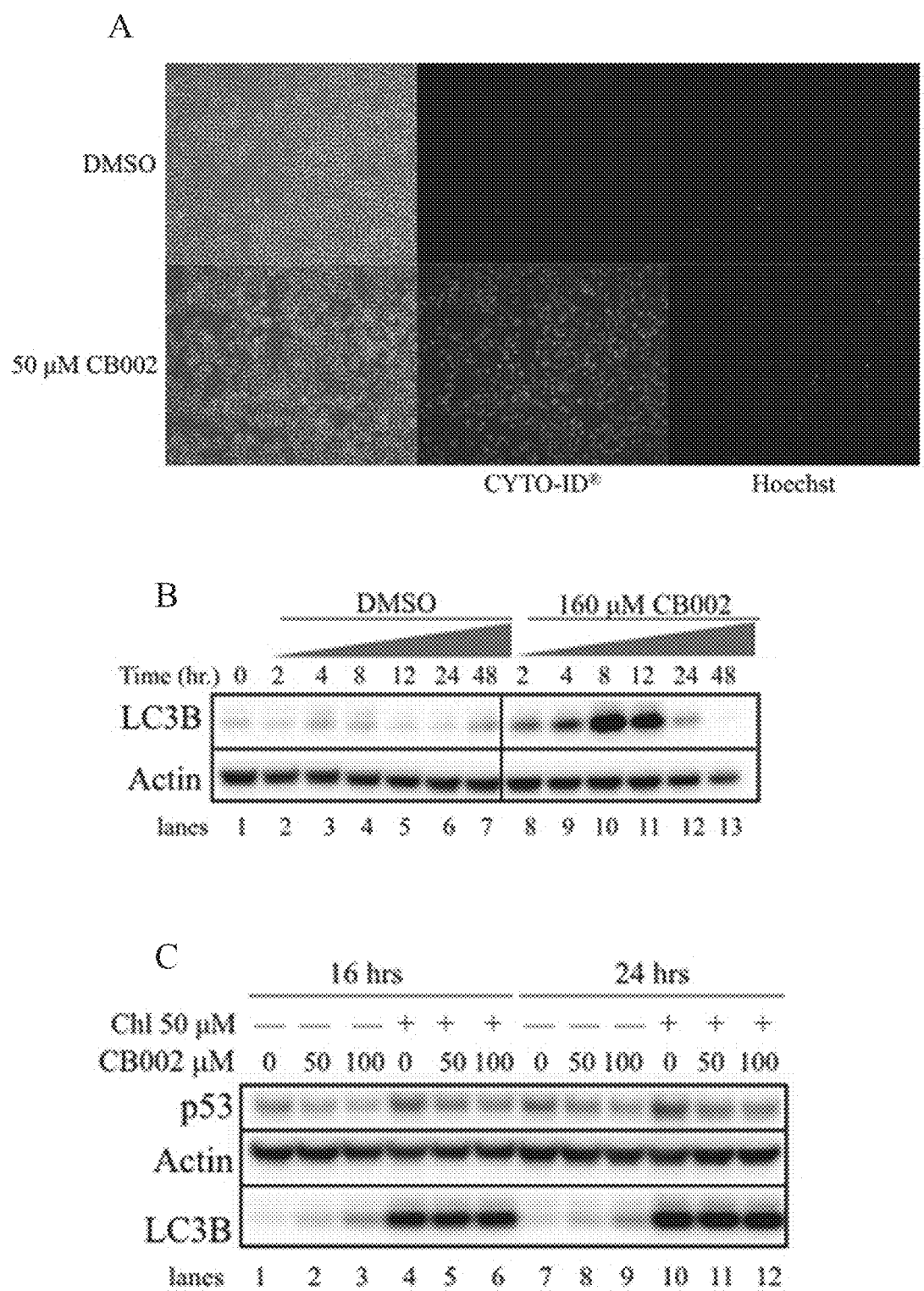
FIG. 8 (Panels A-F) shows CB002-mediated autophagy contributes to apoptotic cell death in drug treated cells.
Figure 8:
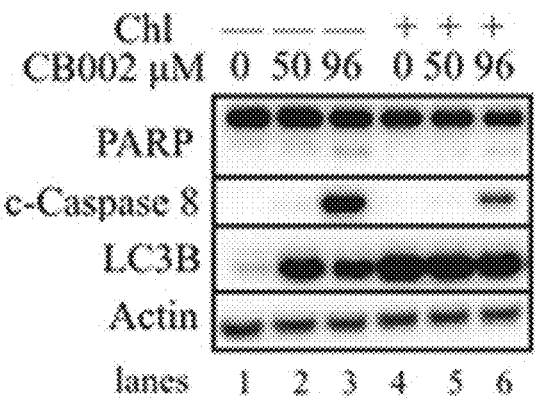
Figure 8:
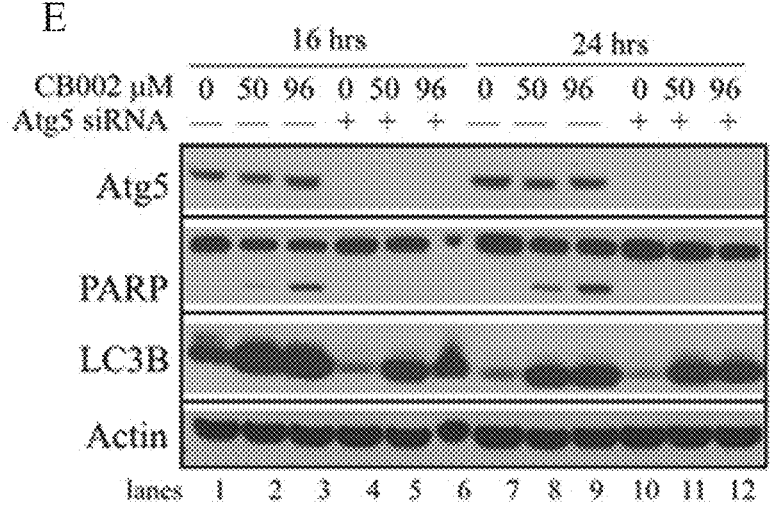
Figure 8:
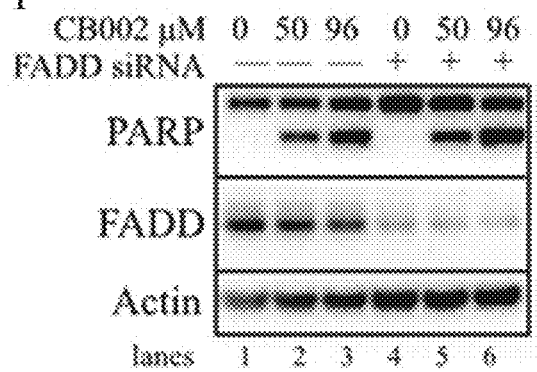

Example 10: Autophagy does not Play a Role in Mutant p53 Degradation but it Appears to be Required for Apoptotic Cell Death During CB002 treatment, cells formed vacuoles suggesting an involvement of an autophagy process. In addition, because it has been recently reported that mutant p53 can be degraded through the lysosome, whether CB002 may induce autophagy as a potential mechanism for R175H mutant p53 degradation was investigated. Using an autophagy detection kit (CYTO-ID® autophagy detection kit, Enzo® Life sciences) an increase in autophagic vacuole-specific staining upon 50 µM CB002 treatment compared to the DMSO control in DLD-1 cells was observed (see, FIG. 8, panel A). To confirm these findings, a Western blot was probed for accumulation of LC3B, a well-known marker used in autophagy studies. Because accumulation of LC3B can indicate a blockage of autophagy, LC3 conversion was evaluated during a time course from 0-48 hours of treatment with 160 µM CB002 in DLD-1 cells. FIG. 8, panel B shows that following CB002 treatment there is an initial increase of LC3B and not in the DMSO treatment (compare lane 1 (0 hr) to lane 2, and 8). LC3B expression increases to a maximum in CB002 treated (see, FIG. 8, panel B, lane 10) followed by a drop of its protein expression. No change in expression of LC3B was observed over time in DMSO control treated cells (see, FIG. 8, Panel B, lanes 2-7). LC3B initially increases in the process of autophagy, and later it is degraded in the lysosomes. Thus, the data indicates that autophagy is being induced by CB002 treatment.

To explore if the R175H mutant p53 was getting degraded through the autophagy mechanism, autophagy was blocked using the autophagosome/lysosome fusion inhibitor, chloroquine (Chl). As expected, treatment with CB002 in HCT116 p53 R175H cells for 16 and 24 hours decreased mutant p53 expression (see, FIG. 8, Panel C, compare lanes 1 to 2 and 3, and 7 to 8 and 9). Co-treatment of CB002 and Chl for 16 and 24 hours did not rescue R175H mutant p53 protein expression, indicating that autophagy does not play a role in CB002 mediated R175H mutant p53 degradation (see, FIG. 8, Panel C, compare lanes 4 to 5 and 6, and 10 to 11 and 12).

As autophagy can be induced for cell survival during cellular stress, its contribution to CB002-induced cell death was investigated. Autophagy was blocked using Chl added to CB002 to treat cells and the effects on apoptotic cell death markers were evaluated. CB002 induced the expression of cleaved caspases and PARP (see, FIG. 8, Panel D, lanes 2 and 3). Upon combination treatment using CB002 and Chl, cleaved caspase 8 and cleaved PARP were reduced compared to CB002 alone (see, FIG. 8, Panel D, compare lanes 2 and 3 to 5 and 6). To further validate this result, autophagy was down-regulated by efficient siRNA-mediated knockdown of the autophagy related 5 (atg5) gene (see, FIG. 8, Panel E, lanes 4-6, and 10-12). Ablation of atg5 resulted in complete loss of PARP cleavage upon treatment of CB002 for 16 and 24 hours (see, FIG. 8, Panel E, lanes 5-6 and 11-12). Although autophagy is mostly thought to be an adaptive process allowing the cell to survive during stress, here it seems to be required for CB002 mediated apoptotic cell death. Other investigators have demonstrated atg5 is implicated in autophagic cell death induced by IFN-γ via interaction with Fas-associated protein with death domain (FADD), a particular scenario that requires caspases. Since the data suggests that atg5 is required for apoptosis, whether the atg5-FADD axis was an interaction required for CB002 mediated cell death was explored. As shown in FIG. 8, Panel F, lane 4-6, suitable knockdown of FADD was achieved. CB002 treatment was able to induce the expression of cleaved PARP in FADD knockdown cells (see, FIG. 8, Panel F, lane 5 and 6) as efficient as the scrambled siRNA (see, FIG. 8, Panel F, lane 2 and 3). Thus, FADD is not crucial in CB002 mediated cell death.

Referring to FIG. 8, CB002 induced autophagy as indicated by specific recognition of autophagic vacuoles (detection using the CYTO-ID® autophagy detection kit at 24 hours) (Panel A) and LC3B protein expression levels in DLD-1 cells (cells were treated with 160 μM CB002 or DMSO control for a period of 2-48 hours (Panel B). Autophagy inhibition by Chl does not rescue mutant p53 protein expression in HCT116 R175H p53 (Panel C). Blocking the autophagy process in SW480 cells with 50 μM chloroquine (Chl) reduced the expression of apoptotic markers cleaved caspase 8 (c-Caspase 8) and cleaved PARP (24 hours) (Panel D). Inhibition of autophagy by Atg5 siRNA completely abolished PARP cleavage in SW480 cells (Panel E). Atg5-FADD apoptosis axis was not involved in CB002 mediated apoptosis in SW480 cells (24 hours) (Panel F).

Example 11: CB002 Restores p53 Pathway in Colorectal Cancer Cells

To identify p53-restoring small molecules, 50000 small molecular compounds of Chembridge library were screened using a functional cell-based assay in SW480 cells which carry a p53-luc reporter. One compound CB002 (ID is 7745998, IPUA name is 8-anilino-1,3-dimethyl-3,7-dihydro-1H-purine-2,6-dione) was found to increase p53 responsive bioluminescence (see, FIG. 9, Panels A, B and C). A CB002-related compound (Analog 11; ID is 849102, IPUA name is 8-anilino-1,3,7-trimethyl-3,7-dihydro-1Hpurine-2,6-dione) in hembridge library (see, FIG. 9, Panel A) was identified. Similar to CB002, Analog 11 increased p53 responsive bioluminescence in a dose dependent manner in SW480 cells (see, FIG. 9, Panels B and C).

Figure 9:
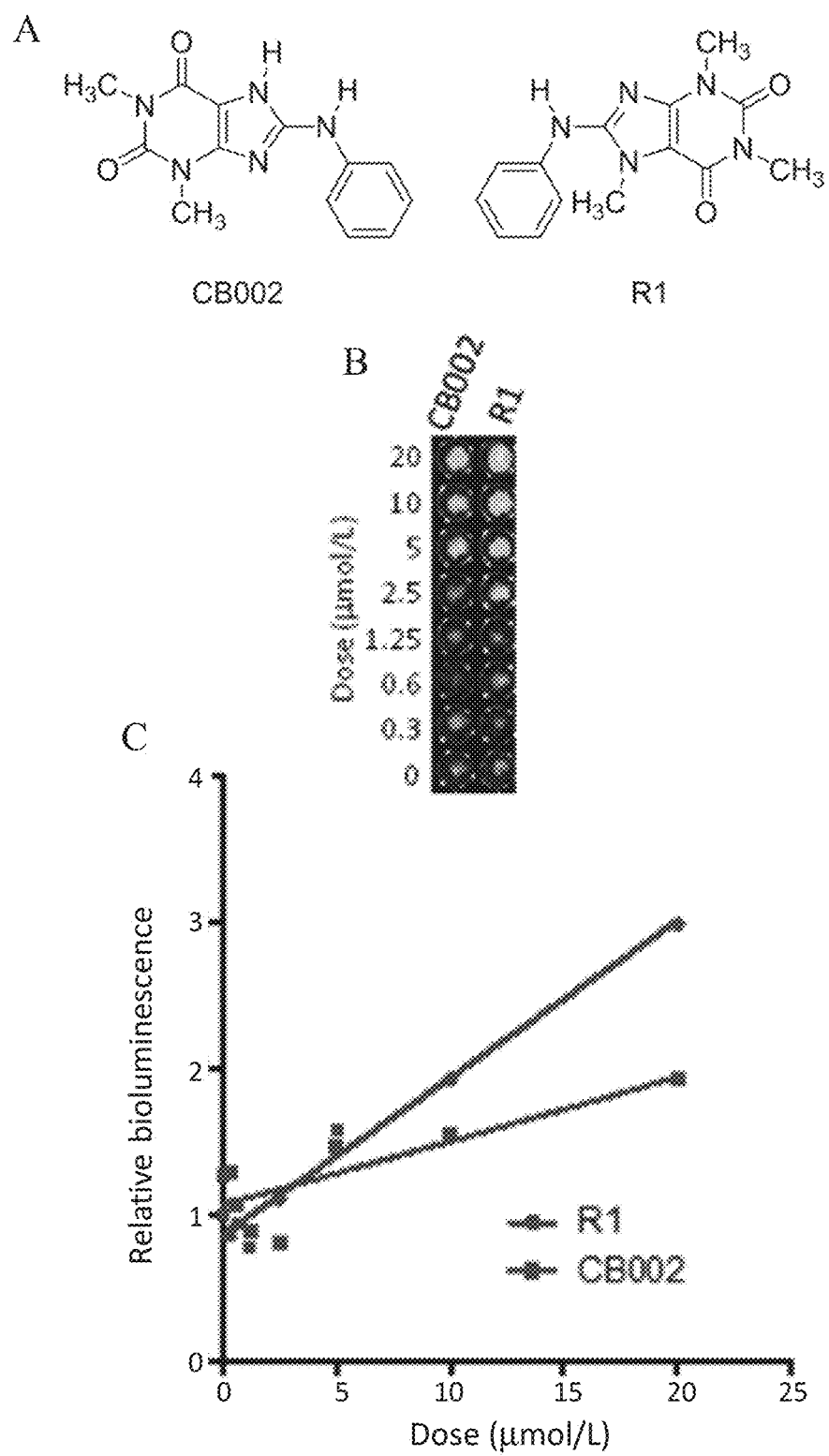
FIG. 9 (Panels A-F) shows screening experimental compounds CB002 and Analog 11 for transcriptional activation by p53 in cancer cells.
Figure 9:
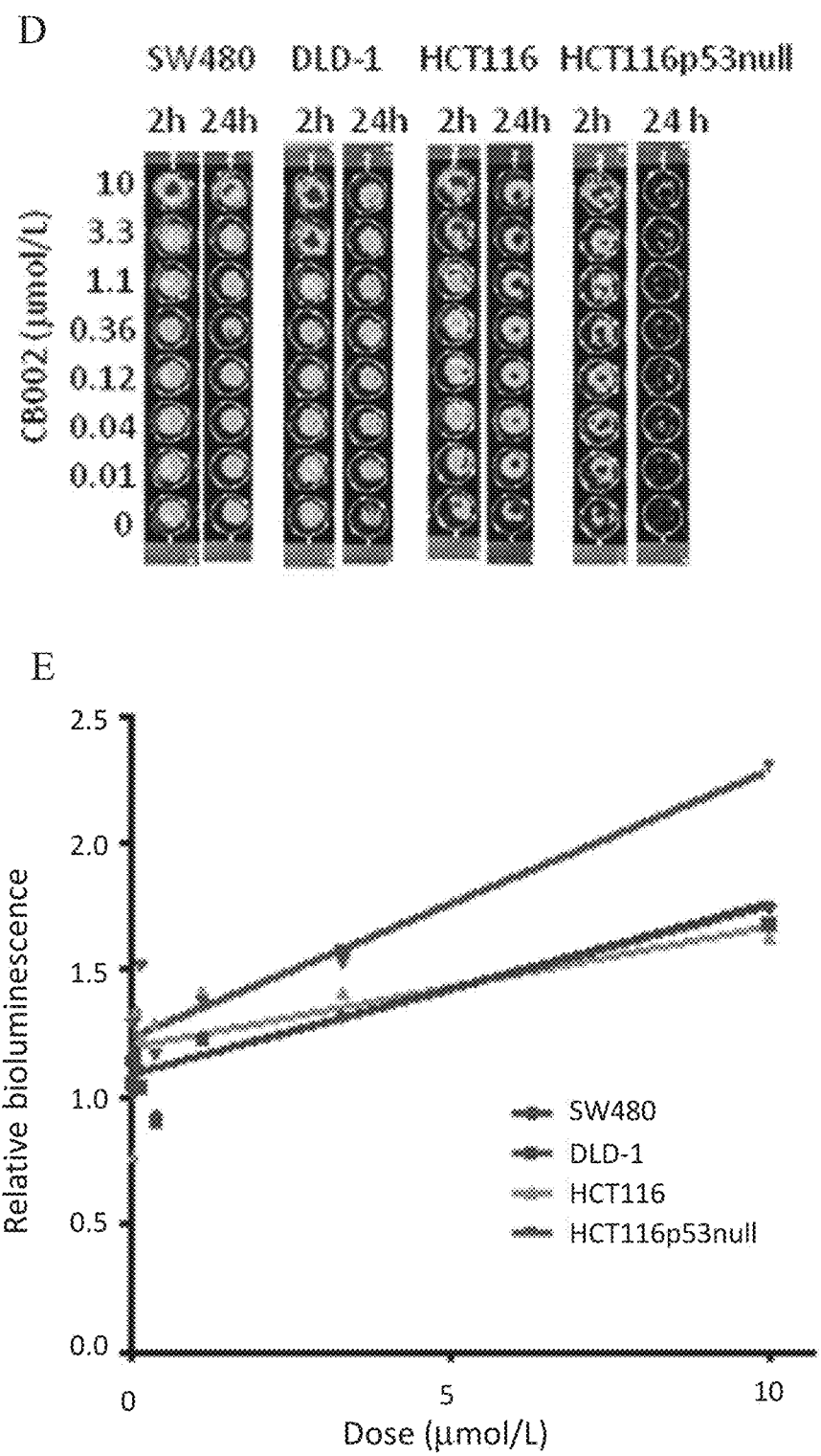
Figure 9:
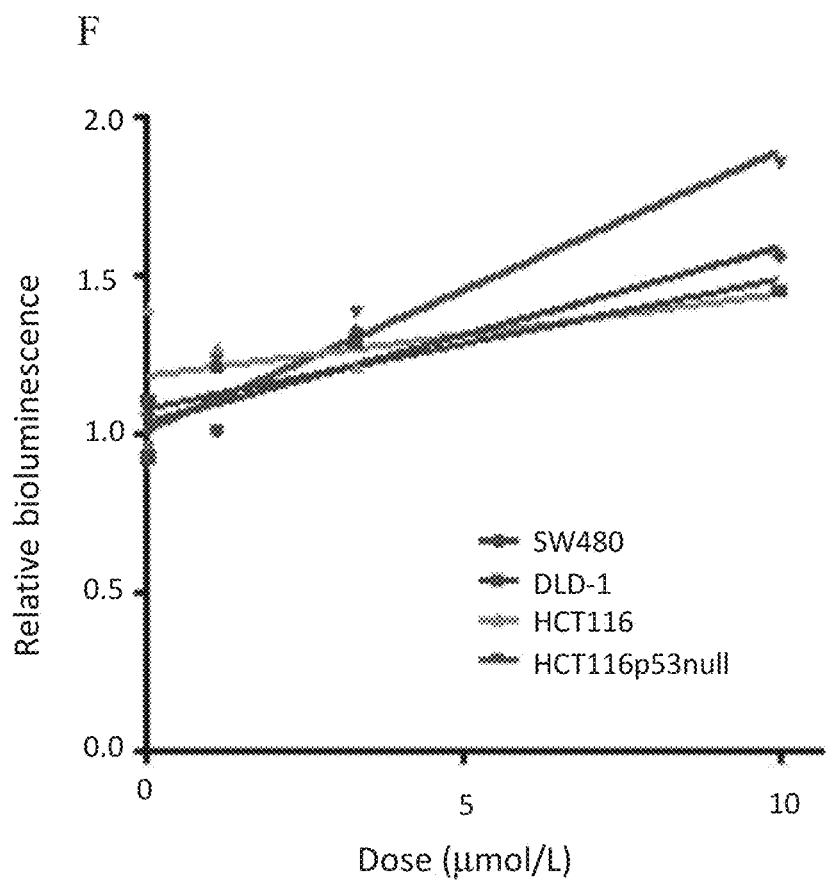

Referring to FIG. 9, the molecular structure of CB002 and Analog 11 (R1) are shown (Panel A). SW480 with p53 reporter cells were treated with CB002 and Analog 11 in doses ranging from 0 to 20 μmol/L (Panel B). p53 responsive bioluminescence was imagined by IVIS. Data are representative of triplicate wells. The relative increase of bioluminescence in panel B is shown (Panel C). Colorectal cancer SW480, DLD-1, HCT116 and HCT116 p53-null cells were treated with CB002 and Analog 11 for 2 and 24 hours (Panel D). p53 responsive bioluminescence was imagined by IVIS. The relative increased bioluminescence in panel D at 2 hours is shown (Panel E). The relative increased bioluminescence in Panel D at 24 hours is shown (Panel F).

CB002 and Analog 11 were further applied to four colorectal cancer cell lines consisting of SW480, DLD1, HCT116, and HCT116 p53 null. As shown in FIG. 9, CB002 increased p53 responsive bioluminescence in both SW480 (mutant p53 R273H, P309S) and DLD-1 (mutant p53 S241F) cells in a dose-dependent manner at 2 and 24 hours, as well as in HCT116 p53 null cells (see, FIG. 9, Panels D, E and F).

Figure 10:
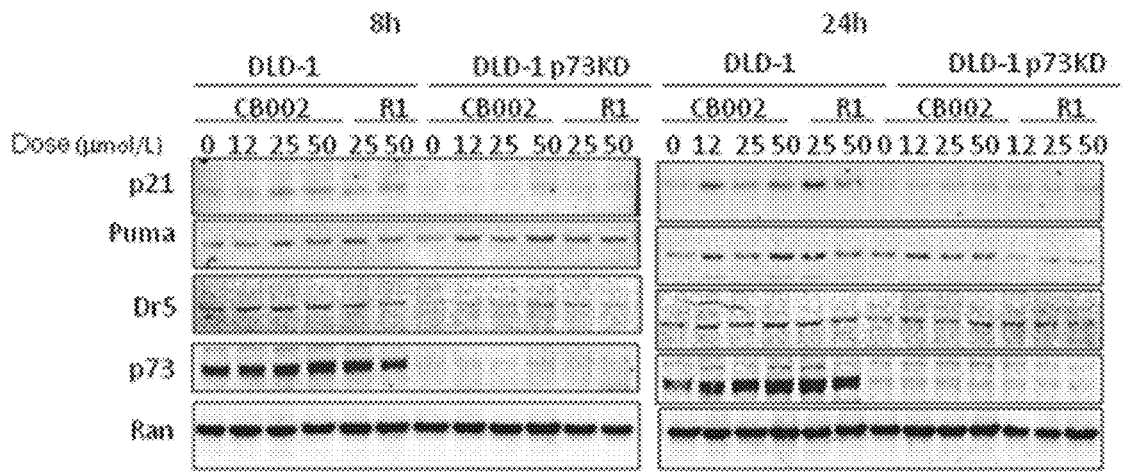
FIG. 10 (Panels A-C) shows the effect of CB002 and Analog 11 on p53 pathway signaling in cancer cells.
Figure 10:
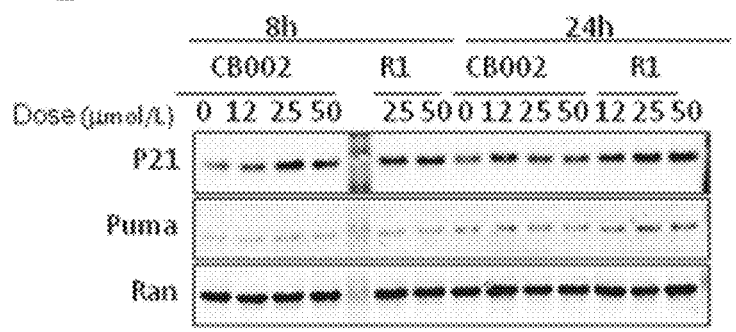
Figure 10:
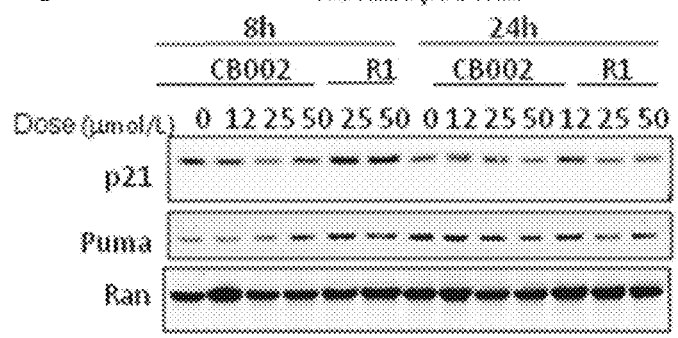

For verification of bioluminescence data, Western blot analysis of endogenous protein levels of p21, PUMA and DR5 (as representative p53 targets) was conducted by varying drug dose and a time course experiment. Referring to FIG. 10, DLD-1 and DLD-p73 knockdown cells (Panel A), HCT116 (Panel B), and HCT116 p53-null cells (Panel C) were treated with CB002 and Analog 11 for 8 and 24 hours. Protein levels of p53 target genes were determined by Western blot analysis. In DLD-1 cells (see, FIG. 10, Panel A), a minor increase in p21 was observed at 8 hours in both CB002 and Analog 11 at doses of 25 μmol/L and 50 μmol/L. At 24 hours there was a moderate increase in p21 with the moderate dose of 12 μmol/L of CB002 and 25 μmol/L of Analog 11. A minor increase in PUMA was observed at the 25 μmol/L and 50 μmol/L doses for CB002, and an increase at the 25 μmol/L but not the 50 μmol/L of Analog 11 at 8 hours. At 24 hours, an increase in PUMA was observed with exposure to CB002 and Analog 11. DR5 was slightly increased in cells treated with CB002 at 8 and 24 hours, but no change of DR5 was observed in cells treated with Analog 11 in DLD-1 cells.

CB002 and Analog 11 were further applied to HCT116 p53-null cells. As shown in FIG. 10, Panel C, in p53-null HCT116, p21 appeared to increase moderately with Analog 11 and CB002 at 8 hours. At 24 hours no consistent difference was observed for both CB002 and Analog 11 at all dosages with an increase at the single 12 μmol/L dose in Analog 11. PUMA appeared to increase at the 50 μmol/L dose at 8 hours and in both the 25 μmol/L and 50 μmol/L doses of Analog 11. At 24 hours no consistent difference in PUMA was observable except a slight decrease in the two Analog 11 dosages. On the basis of the data with p53 responsive bioluminescence and p53 target gene expression, CB002 and Analog 11 restore p53 pathway responses in DLD-1 and HCT116 p53-null cells.

The p53 pathway signaling in HCT116 cells which carry with wild-type p53 was also examined. CB002 increased p53 responsive bioluminescence at 2 hours (see, FIG. 9, Panels D, E and F). Consistent with the data using bioluminescence, p21 appeared to increase moderately in a dose dependent fashion for both CB002 and Analog 11. PUMA expression appeared to increase only at 24 hours with Analog 11 in HCT116 cells (see, FIG. 10, Panel B). These data suggest that CB002 reactivates the p53 pathway in wild-type p53 expressing HCT116 cells.

Figure 11:
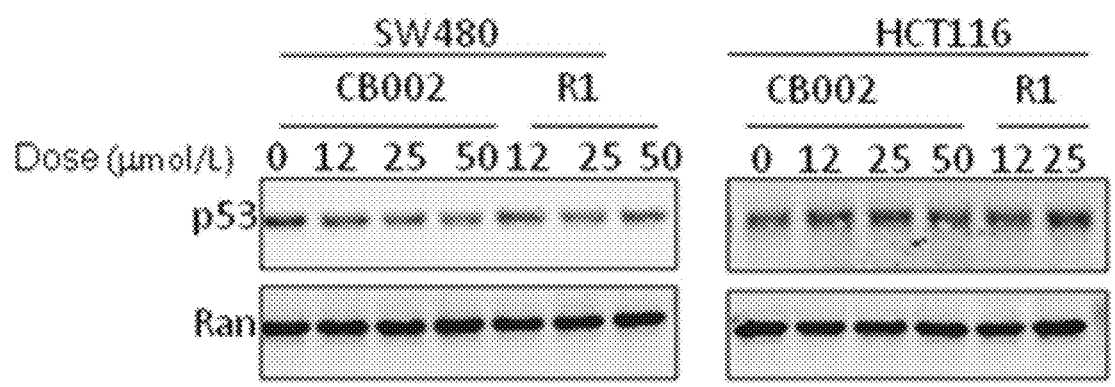
FIG. 11 shows p53 protein level in cancer cells upon CB002 and Analog 11 treatment.

Example 12: CB002 Decreases Mutant p53 Protein Levels in Colorectal Cancer Cells The effect of CB002 and Analog 11 on mutant p53 protein levels was examined in cancer cells. Mutant p53 protein in SW480 cells and wild-type p53 in HCT116 cells were examined via Western blot assay at 24 hours following treatment at varying doses with CB002 and Analog 11. Referring to FIG. 11, SW480 and HCT116 cells were treated with CB002 and Analog 11 for 24 hours. p53 protein was determined by Western blotting using anti-p53 (DO-1). As shown in FIG. 11, mutant p53 protein level appeared to decrease significantly with increasing dose of CB002, and decrease moderately with high dose Analog 11. In contrast, a moderate increase in wild-type p53 was observed with increasing dose of CB002 and Analog 11 in HCT116 cells.

Example 13: CB002 Restores p53 Pathway Signaling in Part Through Activation of p73 in Mutant p53-Expressing Colorectal Cancer Cells CB002 treatment was applied to DLD-1 and p73 knock-down DLD-1 cells at varying doses. Western blot analysis was conducted using DLD-1 and p73 knockdown DLD-1 at 8 hours and 24 hours post-exposure to low ascending doses of CB002 and Analog 11. As shown in FIG. 10, panel A, p21, PUMA and DR5 were increased in protein level at 8 and 24 hours in DLD-1 cells treated with CB002 and Analog 11. By contrast, p21 expression was absent for both CB002 and Analog 11 compounds in p73 knock-down DLD-1 cells. PUMA appeared to have increased expression at 8 hours for both compounds over control. At 24 hours, a reduction in PUMA was observed for Analog 11 with CB002 largely unchanged from control. DR5 appeared to be unchanged at 8 hours and at 24 hours with less protein level in p73 knockdown DLD-1 cells compared with that in DLD-1 cells. p73 protein level appeared to be unchanged in DLD-1 at 8 hours with a non-dose dependent moderate increase at 24 hours over control. p73 protein was not detected at both time points for both compounds in p73 knockdown DLD-1 cells. These results taken together suggest that knockdown of p73 may have some impact on CB002 and Analog 11-restoring p53 pathway signaling in mutant p53-expressing cancer cells.

Figure 12:
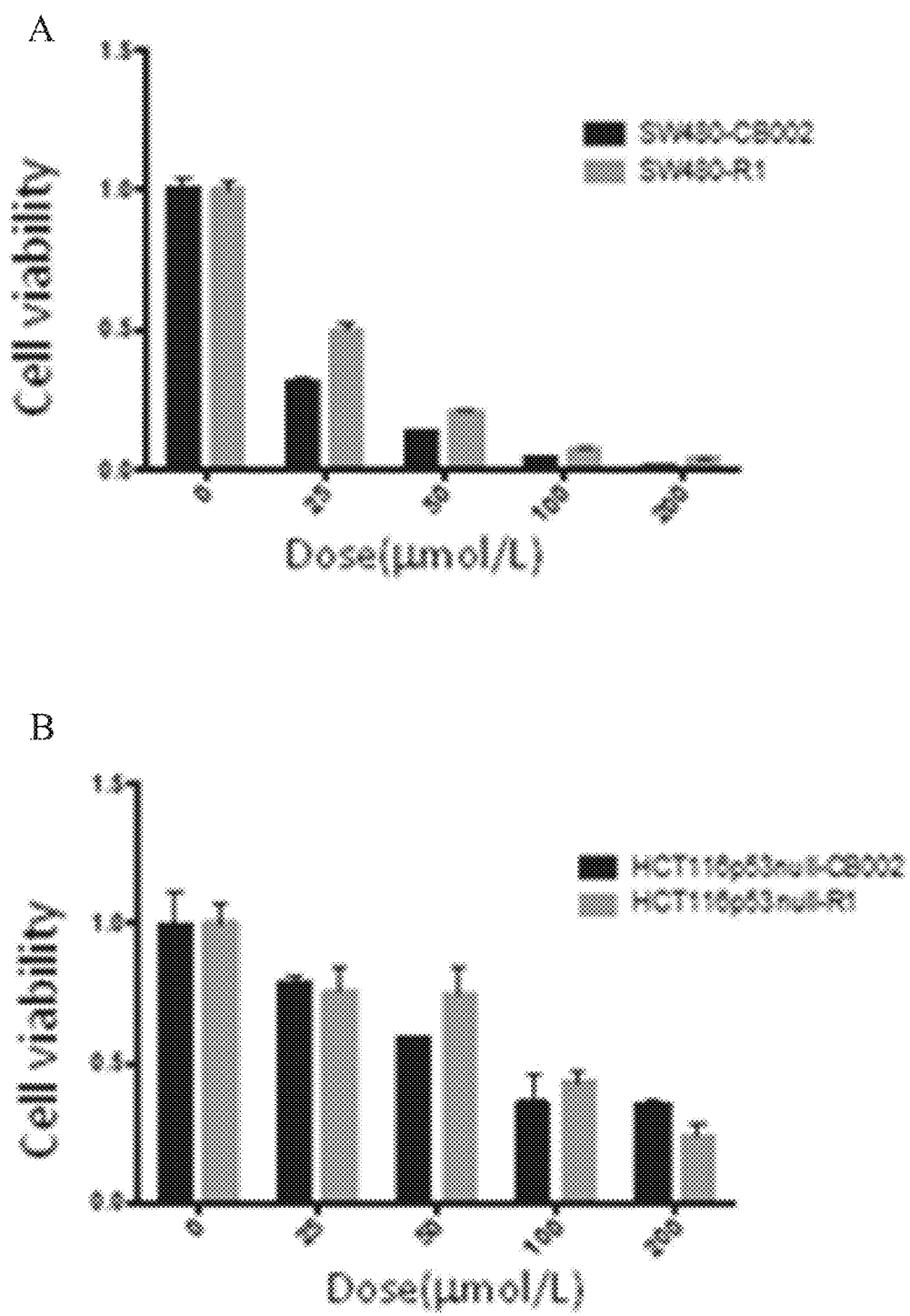
FIG. 12 (Panels A-D) shows CB002 and Analog 11 induce cell death in colorectal cancer cells.
Figure 12:
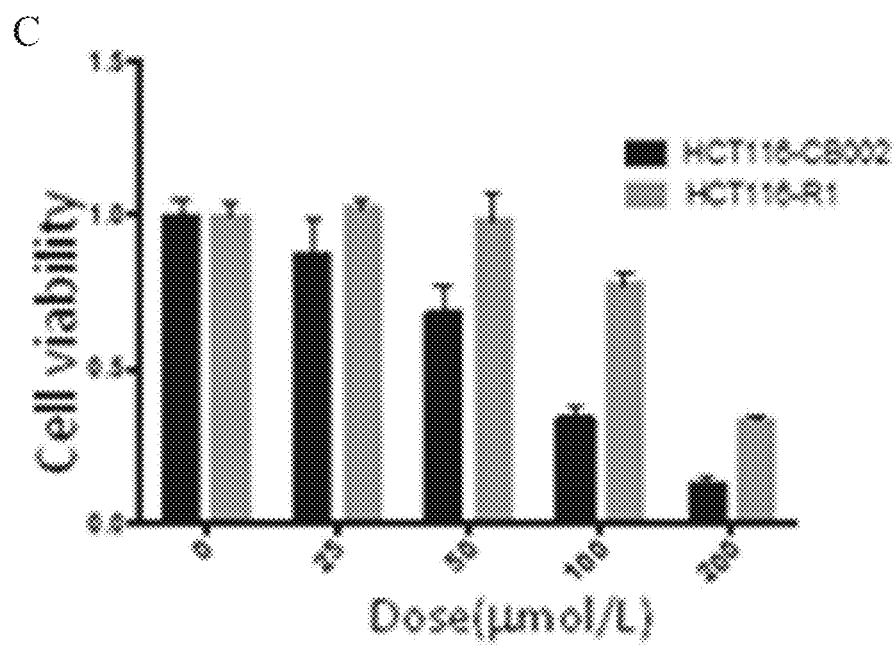
Figure 12:
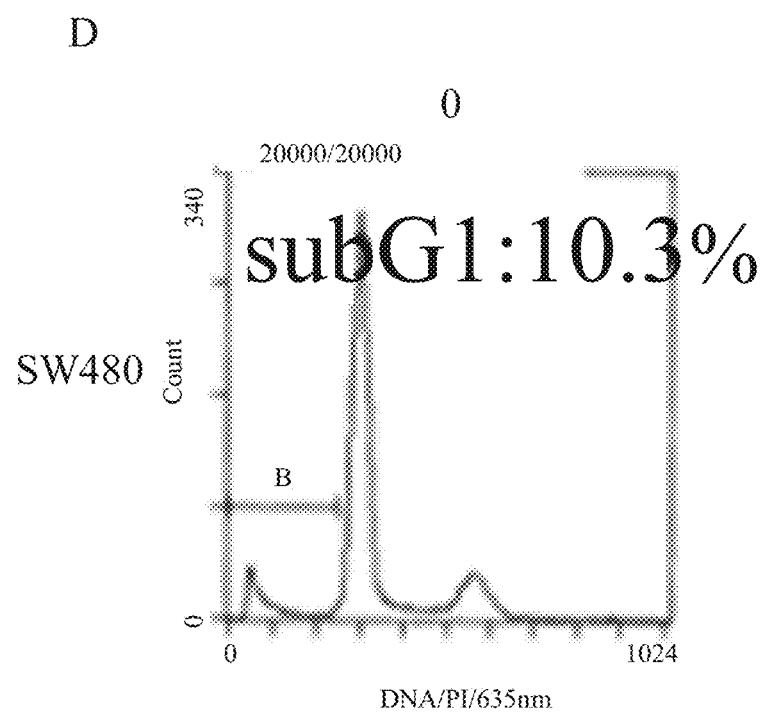
Figure 12:
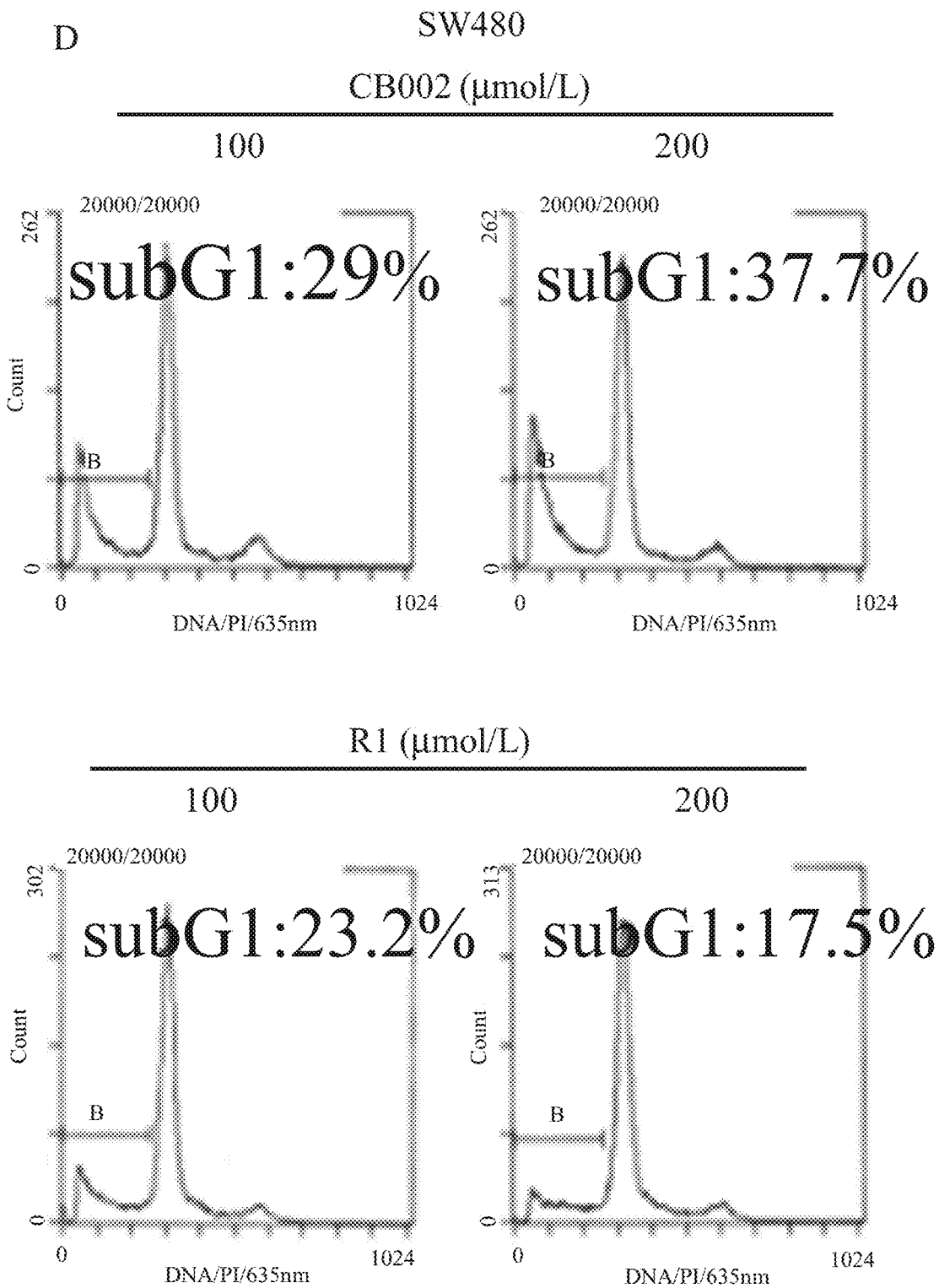
Figure 12:
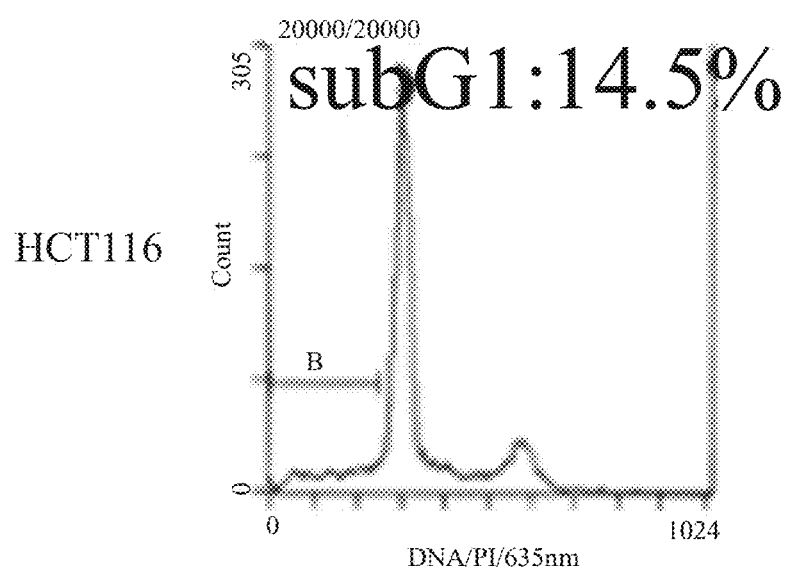
Figure 12:
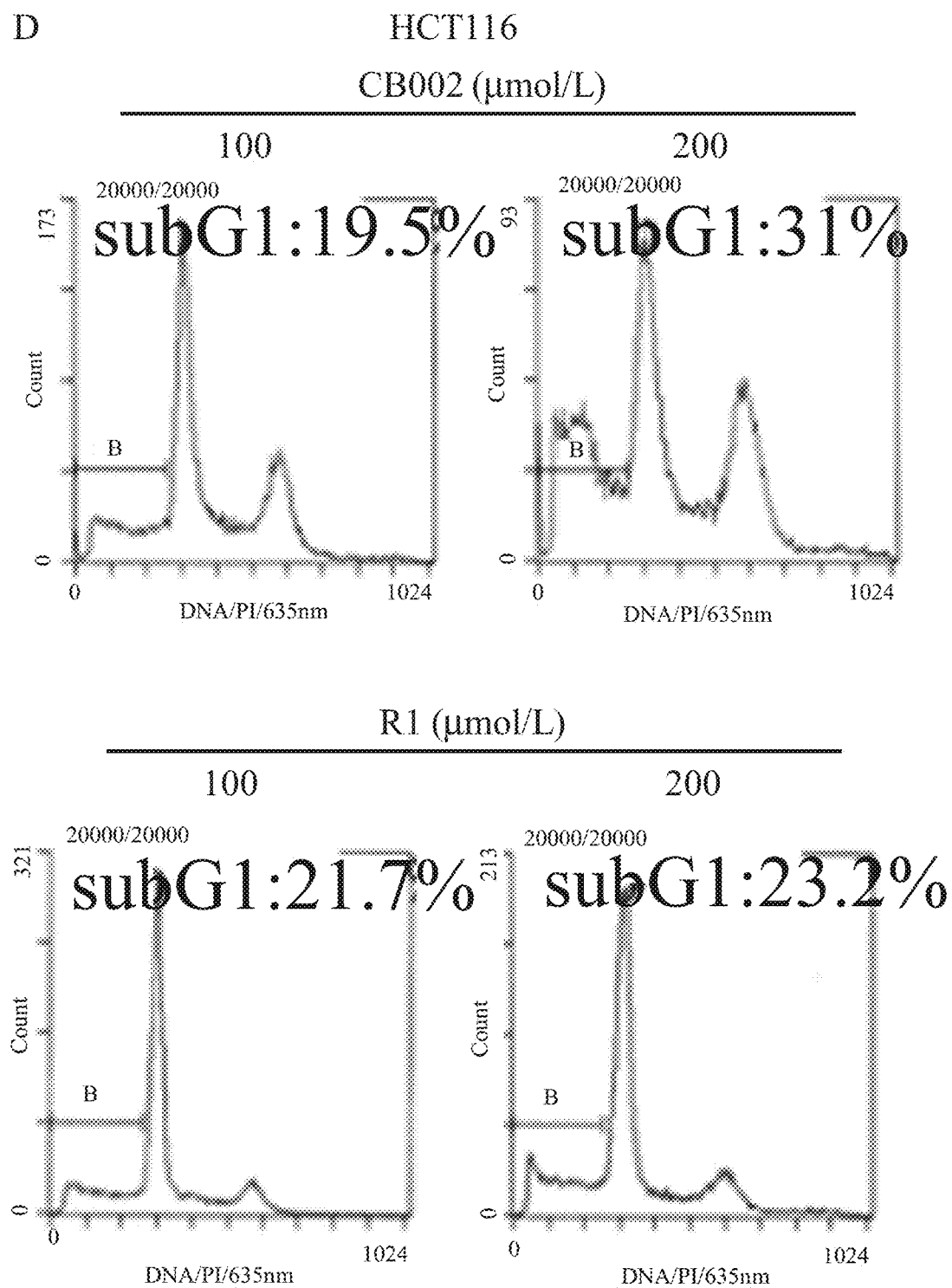
Figure 12:
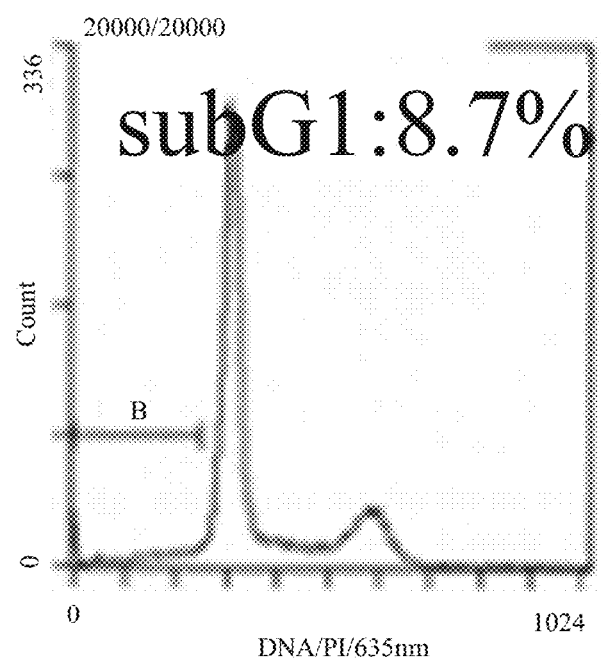
Figure 12:
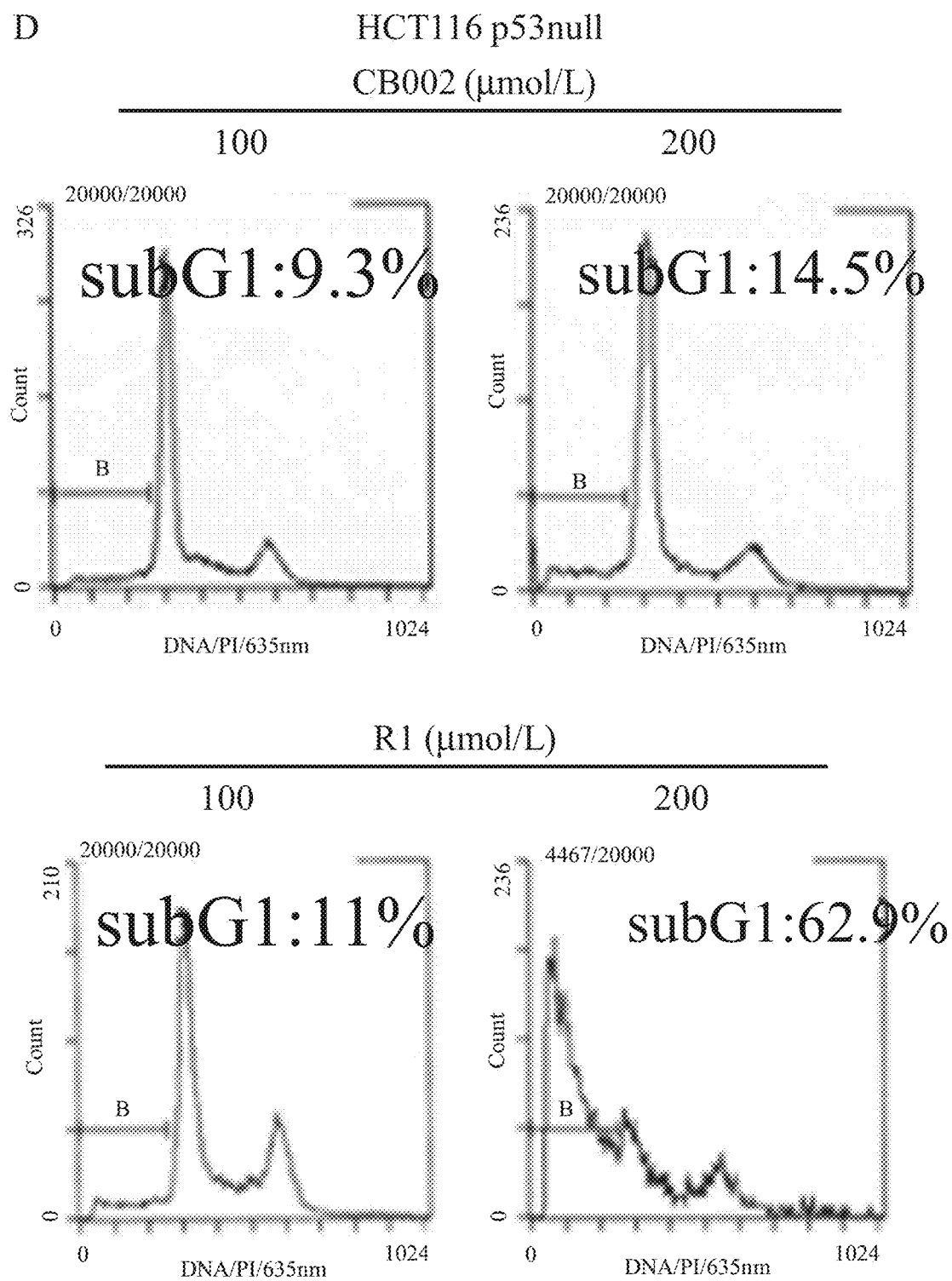

Example 14: CB002 Induces Cell Death in Tumor Cells with No Significant Effect on Normal Cells Whether CB002 and Analog 11 repress cancer cell growth was examined. To address this issue, cell viability and sub-G1 were determined in colorectal cancer cell lines SW480, HCT116, HCT116 p53$^{-/-}$ upon treatment with CB002 and Analog 11. As shown in FIG. 12 (Panels A, B, and C), CB002 and Analog 11 both reduced cell viability in SW480, HCT116 and HT116 p53-null cells in a dose dependent manner with CB002 having the greatest effect. Flow cytometry was conducted to assess sub-G1 fraction in SW480, HCT116 and HCT116 p53-null cells at 72 hours post-treatment. Both CB002 and Analog 11 resulted in increased cells in sub-G1 fraction over untreated controls in SW480, HCT116 and HCT116 p53-null cells in a dose dependent manner. CB002 resulted in a greater percentage of cells in sub-G1 fraction than Analog 11 in SW480 and HCT116 at a dose of 200 μM (see, FIG. 12, Panel D). These results suggest that CB002 and Analog 11 induce cell death in colorectal cancer cells. CB002 has higher anti-tumor efficacy as compared to Analog 11.

Referring to FIG. 12, cell viability of SW480 cells treated with CB002 and Analog 11 at 72 hours is shown (Panel A). Cell viability of HCT116 p53-null cells treated with CB002 and Analog 11 at 72 hours is shown (Panel B). Cell viability of HCT116 cells treated with CB002 and Analog 11 at 72 hours is shown (Panel C). Cell cycle profiles of cancer cells SW480, HCT116 and HCT116 p53-null cells are shown (Panel D). Cells were treated with CB002 and Analog 11 for 72 hours. Cell viability (Panels A, B, and C) was normalized to DMSO as control. Data are expressed as mean±SD.

CB002 was applied to human normal fibroblast Wi38 cells. IC$_{50}$ of CB002 in Wi38 cells was much higher than those in colorectal cancer cells, SW480, DLD-1, HCT116 and HCT116 p53-null cells (see, FIG. 13, Panels A and B), suggesting that there is a favorable therapeutic index between normal cells and cancer cells. Flow cytometry showed relatively unchanged sub-G1 fraction in normal Wi38 cells treated at the dose (200 μM) of CB002 that effectively increased 20% of cells in sub-G1 in SW480 cancer cells at 72 hours (see, FIG. 13, Panel C).

Figure 13:
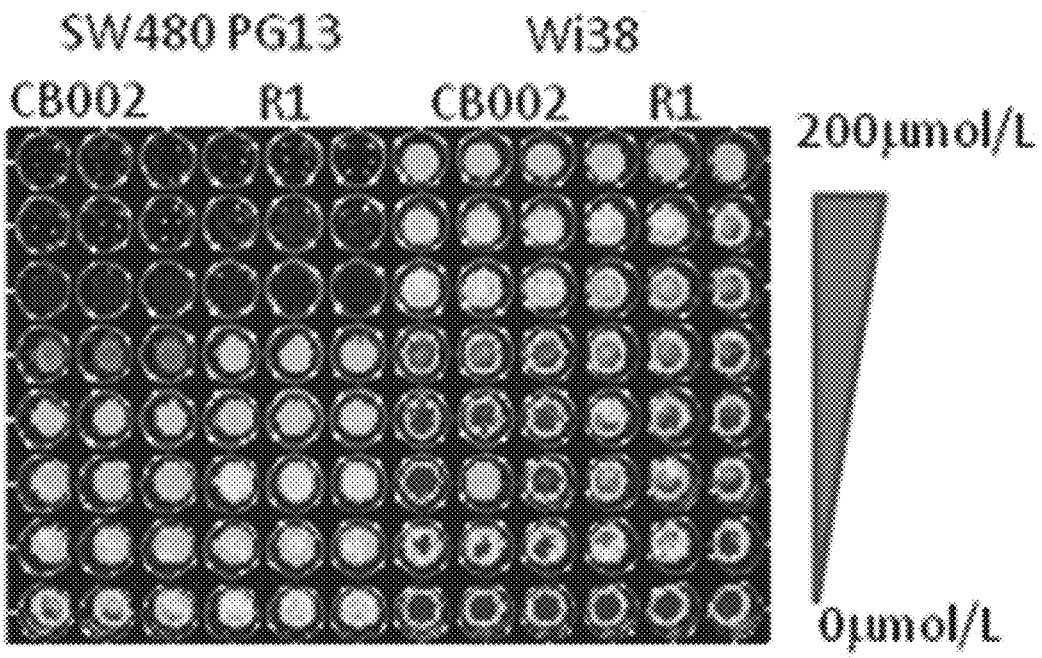
FIG. 13 (Panels A-C) shows CB002 induces cell death in tumor cells with no significant effect on normal cells.
Figure 13:
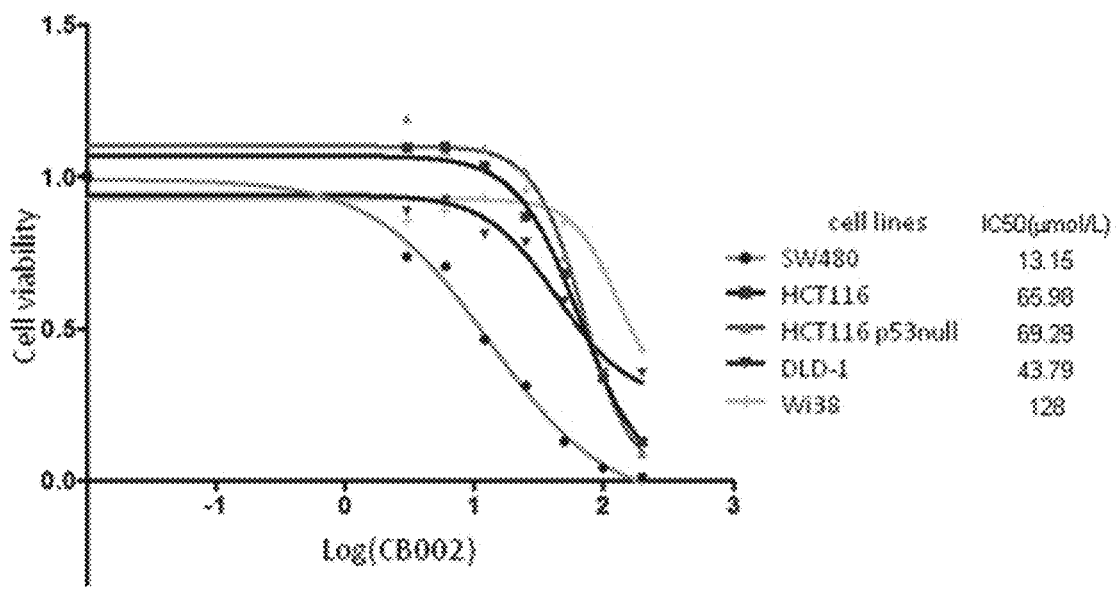
Figure 13:
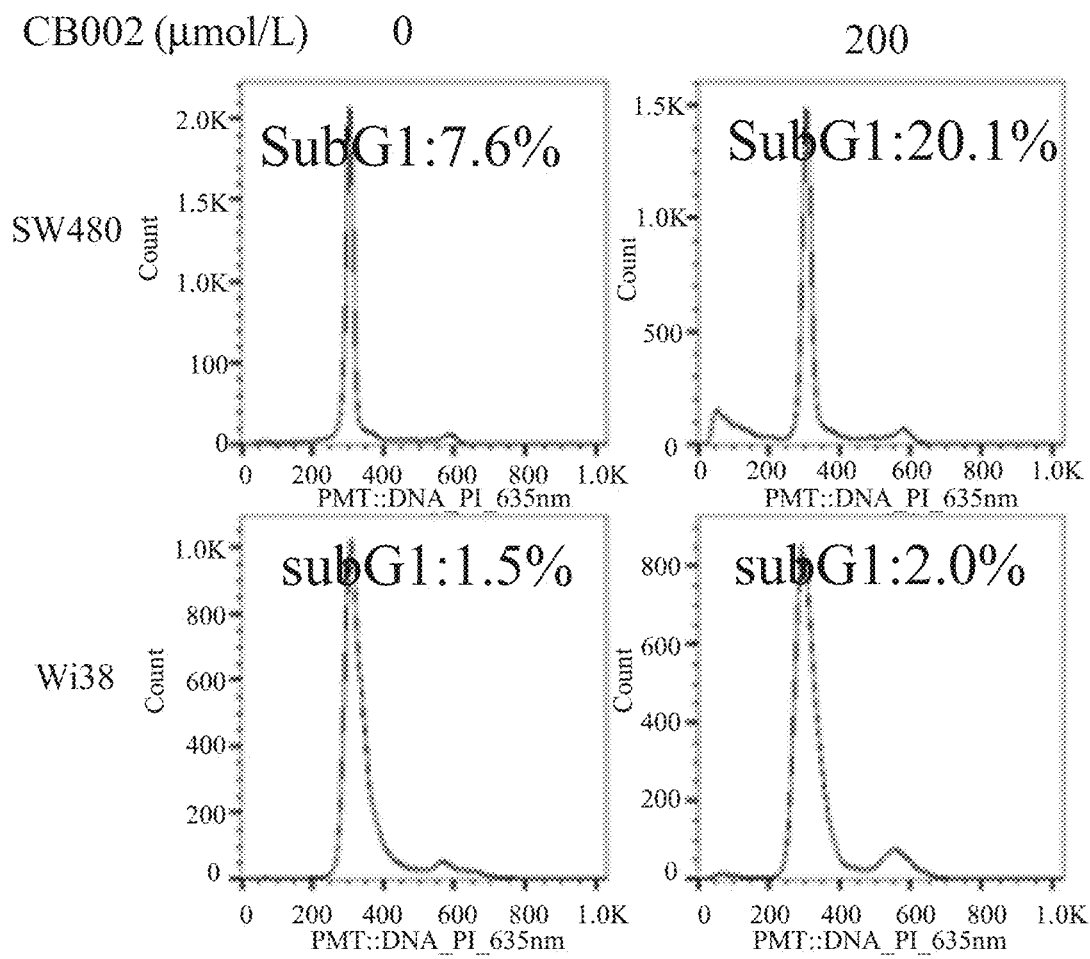

Referring to FIG. 13, imaging of Cell Titer-Glo as a cell viability assay of SW480 and Wi38 cells treated with CB002 and Analog 11 for 72 hours is shown (Panel A). IC$_{50}$ of CB002 in cancer cells and normal fibroblast Wi38 cells based on the cell viability is shown (Panel B). The cells were treated with CB002 for 72 hours. Cell cycle profiles of SW480 and Wi38 cells treated with CB002 for 72 hours are shown (Panel C).

Figure 14:
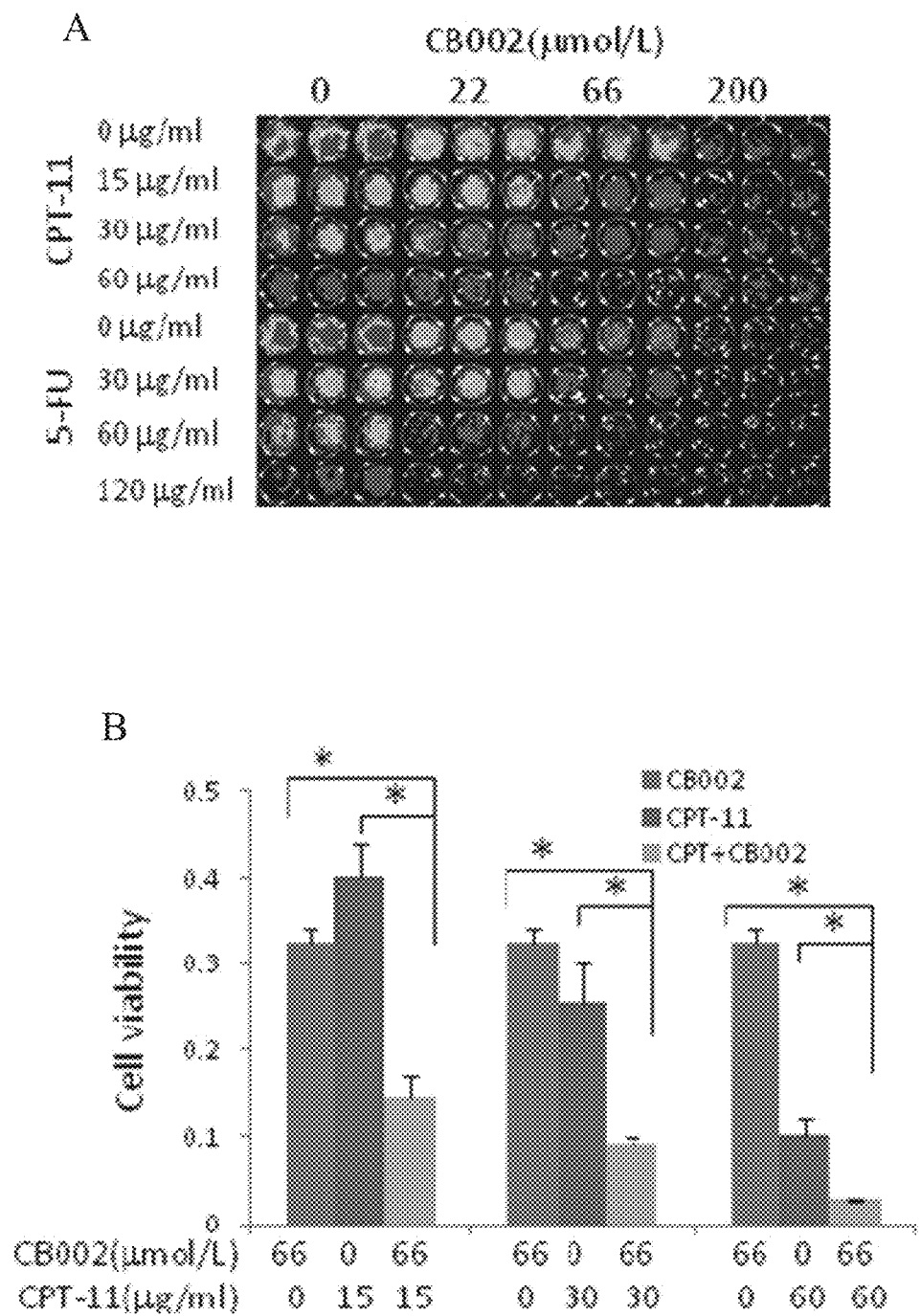
FIG. 14 (Panels A-E) shows synergistic effects of CB002 and CPT-11 or 5-FU in treated cancer cells.
Figure 14:
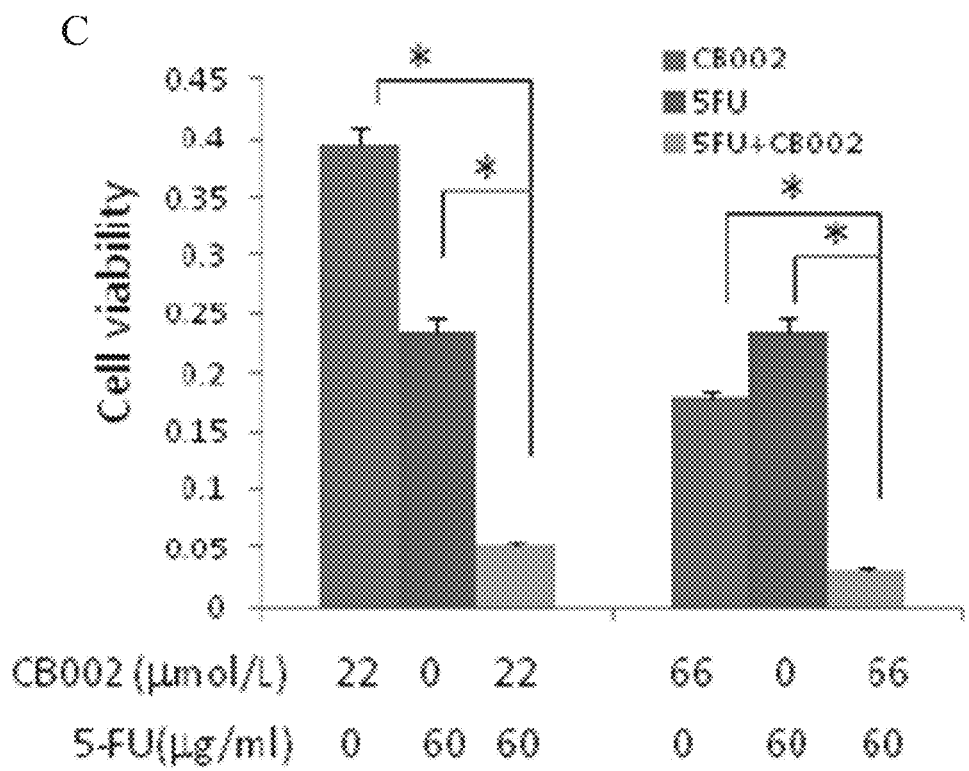

Example 15: CB002 Synergizes with CPT-11 and 5-FU to Suppress Cell Growth in Colorectal Cancer Given that 5-FU and CPT-11 are traditional chemotherapy for colorectal cancer patients often used in combination treatment, whether CB002 can synergize with CPT-11 or 5-FU in inducing cell death in colorectal cancer cells was examined. To address this question, combination treatment of CB002 with CPT-11 or 5-FU was assessed with escalating doses in SW480 cells. Referring to FIG. 14, SW480 cells were treated with CB002 and CPT-11 or 5-FU for 72 hours. Imaging of CellTiter-Glo cell viability of SW480 treated with CB002 and CPT-11 or 5-FU I shown (Panel A). Cell viability of SW480 cells treated with CB002 and CPT-11 is shown (Panel B). Cell viability of SW480 cells treated with CB002 and 5-FU is shown (Panel C). Combination Index of CB002 and CPT-11 is shown (Panel D). Combination Index of CB002 and 5-FU is shown (Panel E). Cell viability was normalized to DMSO as control. *p<0.05. Combination index (CI)<1, =1 and >1 indicate synergism, additive effect, and antagonism in drug combination treatment.

As shown in FIG. 14, cell viability of cancer cells had greater reduction with ascending doses of each agent with greater toxicity observed in 5-FU over CPT-11 (see, FIG. 14, Panel A). Combination treatment with CB002 (66 µM) and CPT-11 (a series of doses) significantly reduced cell viability in SW480 as compared to the single agent treatments alone (see, FIG. 14, Panel B). Further combination index (CI) analysis indicates a synergism of this combination of CB002 and CPT-11 (see, FIG. 14, Panel D). Similar to the combination treatment of CB002 and CPT-11, CB002 synergized with 5-FU-induced cell death. As shown in FIG. 14, Panels C and E, combinational treatment of CB002 (22 µM and 66 µM) with 5-FU (60 µg/ml) significantly reduced cell viability in SW480 cells as compared with the single agent treatment alone. Combinational index (CI<1.0) indicates a synergism of CB002 and 5-FU in cancer cells.

Figure 15:
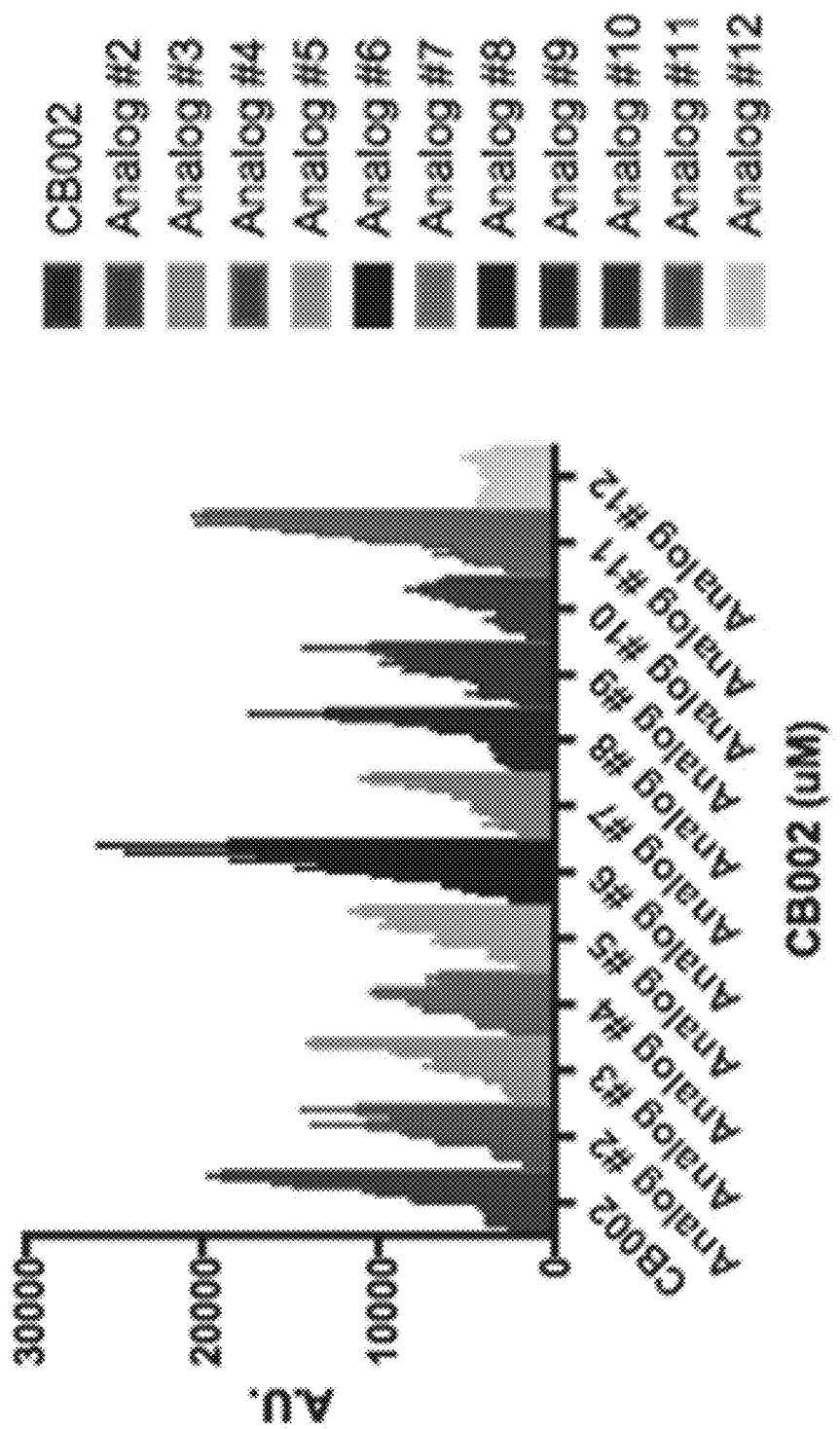
FIG. 15 shows structural analogs activate p53 reporter activity in SW480 cells in a dose dependent manner (6 hours).

Example 16: CB002 and Structural Analogs Activate the p53 Reporter Activity in Colorectal Cancer Cells Referring to FIG. 15, $2\times10^4$ cells/well were seeded in a 96-well plate. A serial dilution of 1-100 µM of the indicated CB002 analog was used to treat SW480 cells carrying the luciferase p53 reporter. The data indicates that the luciferase p53 reporter activity is induced in a dose dependent manner by the treatment of various structural analogs (6 hours).

Figure 16:
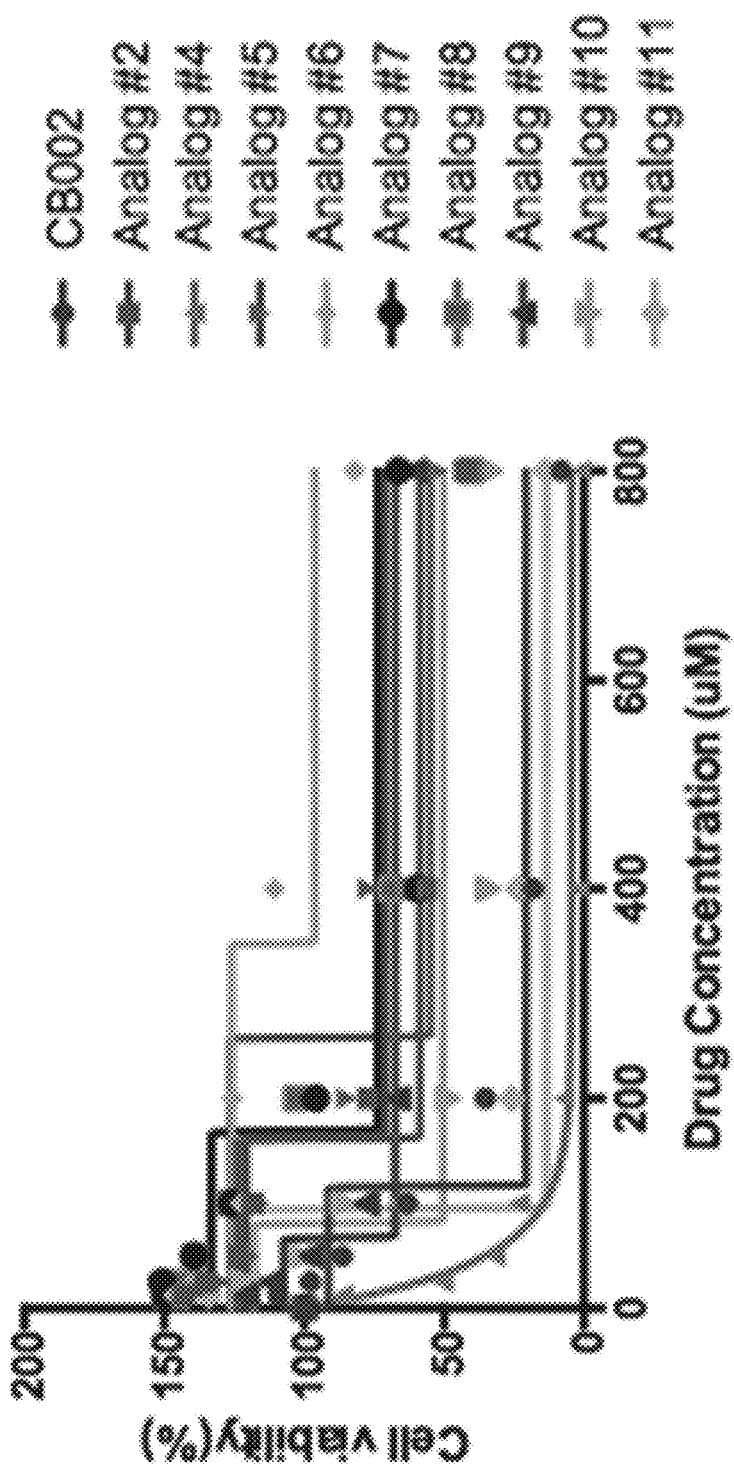
FIG. 16 shows therapeutic indexes for structural analogs was determined in SW480 cells.

Referring to FIG. 16, $1\times10^4$ cells/well were seeded in a 96-well plate. A serial dilution was performed to determine the dose response for each indicated CB002 analog. The $IC_{50}$ for each CB002 analog was determined in SW480 cells by the Cell Titer-Glo® Assay. Analog 4 was the most potent compound.

Figure 17:
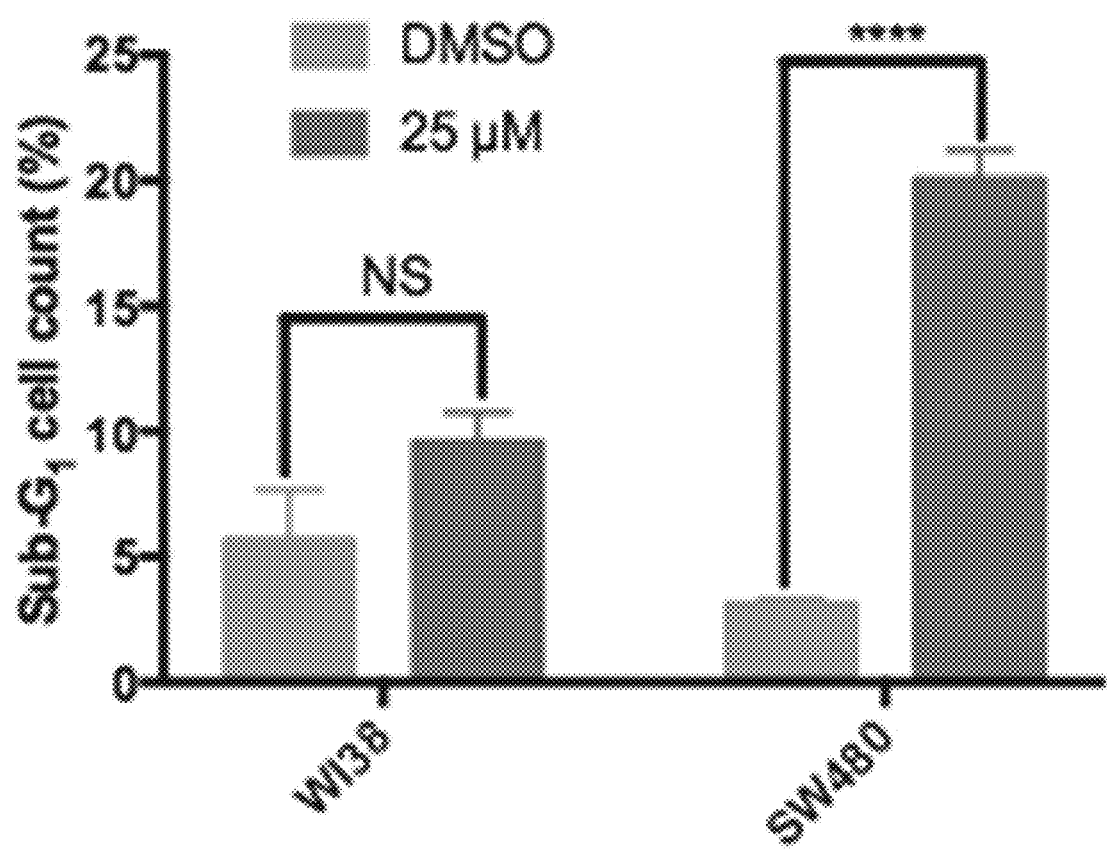
FIG. 17 shows Analog 4 increased apoptotic cells as indicated by the Sub-$G_1$ content. Two-way ANOVA, *p<0.05, **p<0.0001.

Example 17: CB002 Promotes Mutant p53 Degradation which is Enhanced by Ganetespib Treatment Referring to FIG. 17, $2.5\times10^5$ cells/well were seeded in a 6-well plate and treated with either vehicle control or 25 µM Analog 4 for a 48 hour treatment. Cells were then subjected to propidium iodide staining cell cycle analysis. Sub-G1 content indicates that only SW480 cancer cells treated with analog 4 underwent apoptosis and not normal human fibroblast WI38 cells. Two-way ANOVA, **** p<0.0001.

Figure 18:
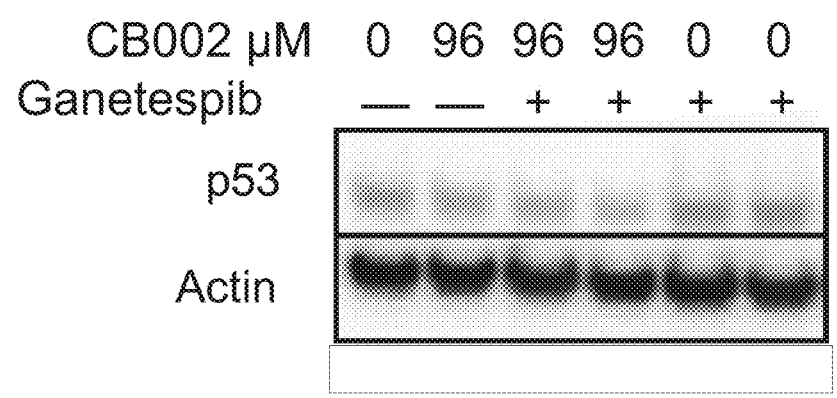
FIG. 18 shows ganetespib treatment enhances CB002 mediated mutant p53 degradation in RXF393 cells (16 hours).

Referring to FIG. 18, $5\times10^5$ cells/well were seeded in a 12 well plate. RXF393 cells were treated with 96 µM CB002 and/or 0.1 µM Ganetesbip for 16 hours. p53 expression was analyzed by Western Blot analysis and showed that Ganetespib treatment enhanced CB002-mediated mutant p53 degradation in RXF393 cells.

Figure 19:
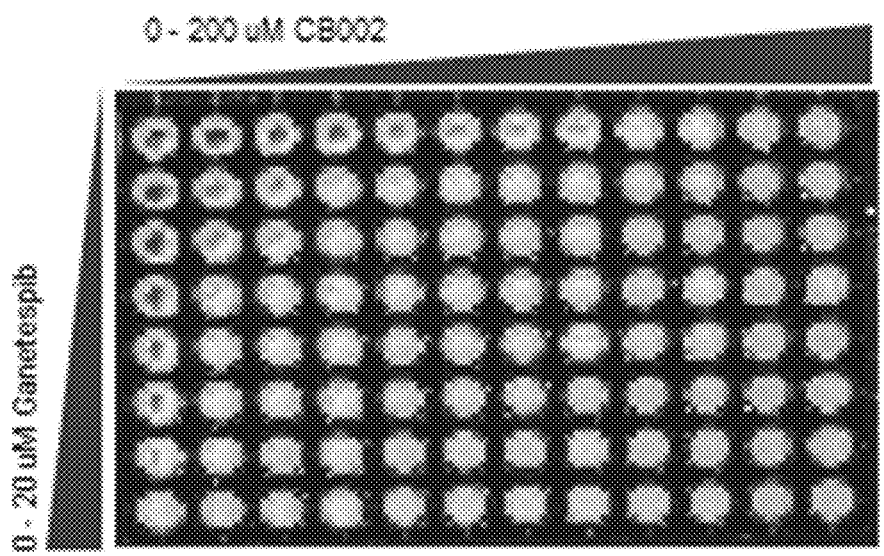
FIG. 19 (Panels A and B) shows CB002 and Analog 11 synergize with ganetespib (Panel A) and Irinotecan (Panel B), respectively. SW480 cells were treated as indicated for 24 hours.
Figure 19:
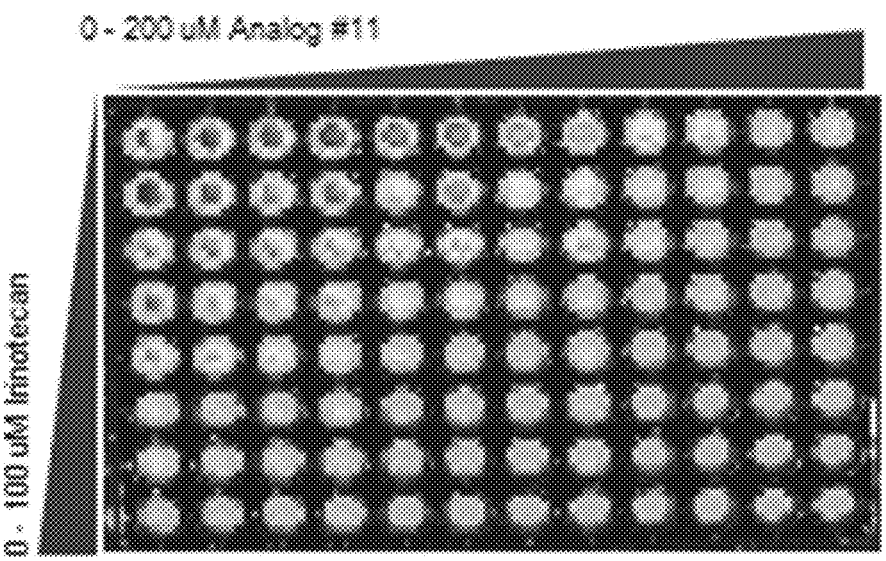

Referring to FIG. 19 (panels A and B), $1\times10^4$ cells/well of SW80 cells were seeded in a 96-well plate. The cells were treated for 24 hours with a combination of 0-20 µM Ganetestib with 0-200 µM CB002 (panel A), and 0-100 µM Irinotecan with 0-200 µM Analog 11 (panel B). CompuSyn software was used to analyze the combination index (CI) of both drugs. The results suggest that CB002 synergizes with Ganetespib (see, panel A) and Analog 11 synergizes with Irinotecan (see, panel B).

Example 18: CB002 and Derivatives Induce NOXA Protein Expression in Colorectal and Multiple Myeloma Cancer Cells Referring to FIG. 20 (panels A and B), $6\times10^5$ cells/well were seeded in a 12-well plate. SW480 cells were treated with either 12 or 25 µM Analog 4 for 16 and 24 hours. The expression of p53 targets DR5 and Noxa, p53 and apoptotic marker cleaved Parp were analyzed by Western Blot analysis. Analog 4 appeared to restore the p53 pathway as indicated by increased expression of DR5, Noxa, and cleaved Parp (see, panel A). Induction of Noxa expression was a property shared by the 24 hour treatment of 100 µM CB002, 25 NM Analog 4, and 100 µM Analog 11 in SW480 cells (see, panel B).

Figure 20:
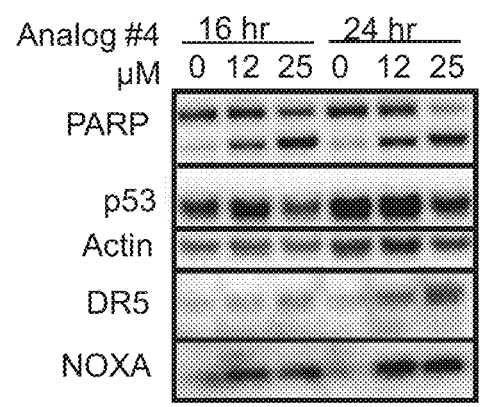
FIG. 20 (Panels A-C) shows Analog 4 restores the p53 pathway in SW480 cells, resulting in PARP cleavage (Panel A); NOXA expression is increased by CB002 and derivatives at 24 hours in SW480 cells (Panel B); 8226 bortezomib resistant multiple myeloma cells (Panel C).
Figure 20:
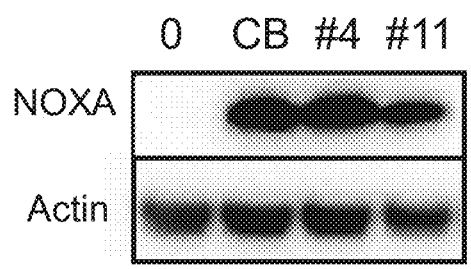
Figure 20:
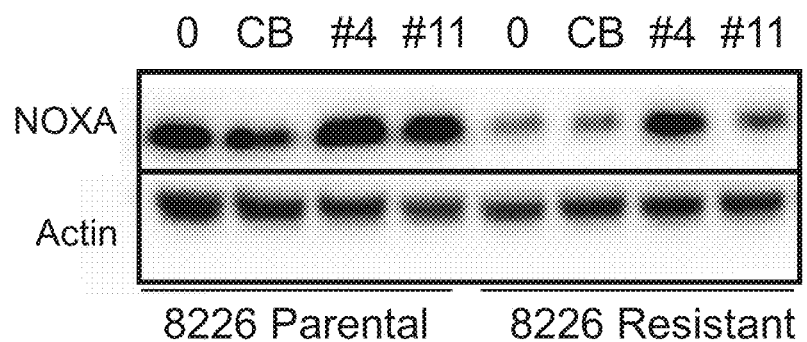

Referring to FIG. 20 (panel C), $1\times10^6$ cells/well were seeded in a 12-well plate. 8226 parental and resistant multiple myeloma cell lines were treated with 100 µM CB002, 25 µM Analog 4, or 100 µM Analog 11. Western Blot analysis showed that Analog 4 and Analog 11 were able to induce Noxa expression in 8226 bortezomib resistant cell line.

Example 19: CB002 Derivatives Sensitize Resistant Cells to Bortezomib

Figure 21:
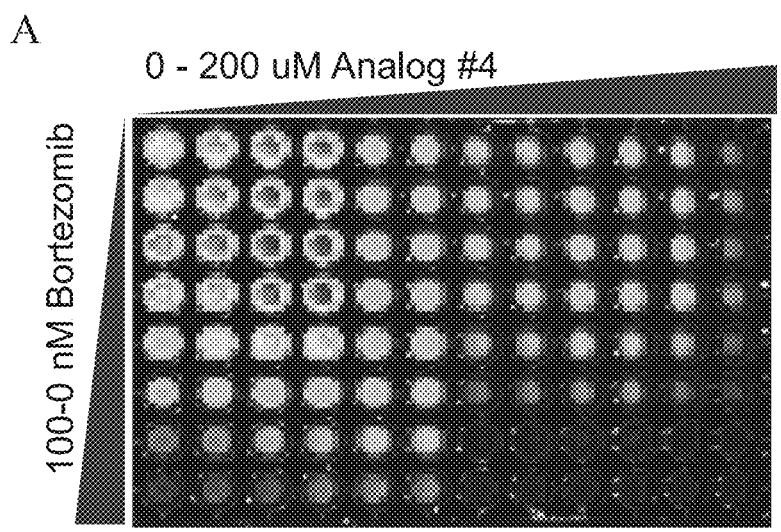
FIG. 21 (Panels A-C) shows 24 hours treatment of bortezomib in combination with structural Analog 4 (Panel A); Analog 11 (Panel B); synergistic cell death by Analog 4 and bortezomib at 48 hours as indicated by the CI. Bortezomib therapeutic indexes for MM1S cell line at 36 hours (Panel C).
Figure 21:
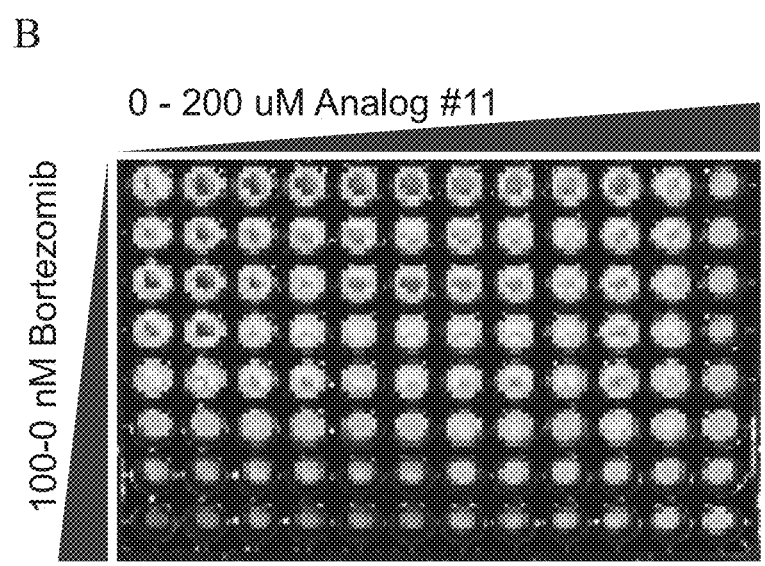
Figure 21:
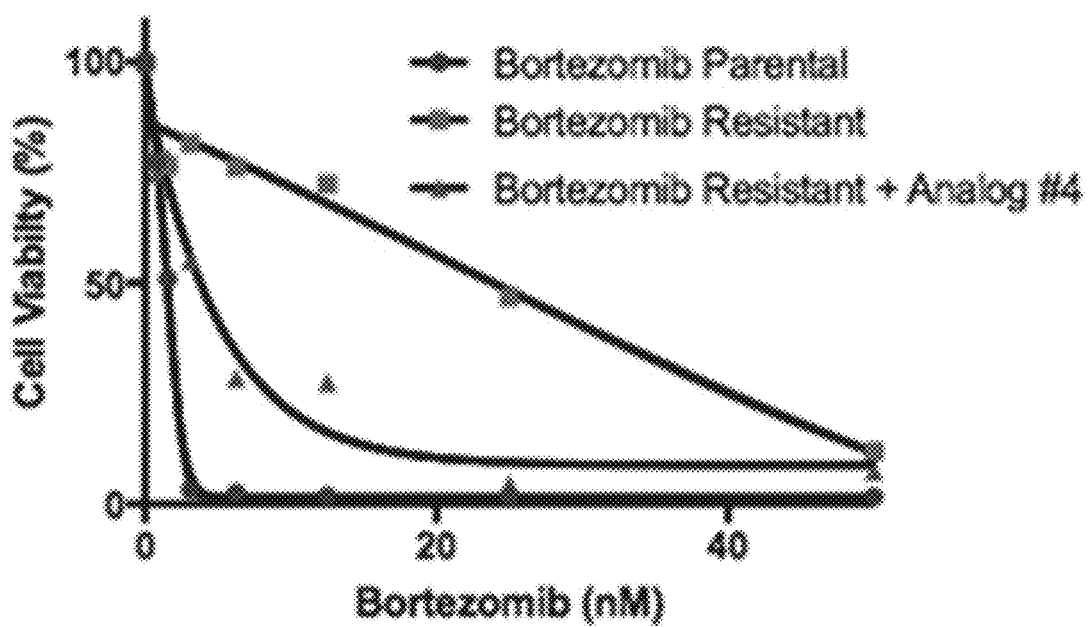

Referring to FIG. 21 (panels A and B), $3\times10^4$ cells/well of 8226 cells were seeded in a 96-well plate. The cells were treated for 48 hours with a combination of 0-100 nM Bortezomib with 0-200 µM Analog 4 (see, panel A) and 0-100 nM Bortezomib with 0-200 µM Analog 11 (see, FIG. 21, panel B). CompuSyn software was used to analyze the combination index of both drugs. The results indicate that Analog 4 was able to synergyze the most with Bortezomib when compared to Analog 11.

Referring to FIG. 21 (panel C), $3\times10^4$ cells/well of MM1S parental and Bortezomib MM1S resistant cells were seeded in a 96-well plate. Cell viability was determined by the Cell Titer-Glo® Assay. The results suggest that treating MM1S Bortezomib resistant cells with 25 µM Analog 4 is able to sensitize MM1S resistant cells to Bortezomib treatment.

Figure 22:
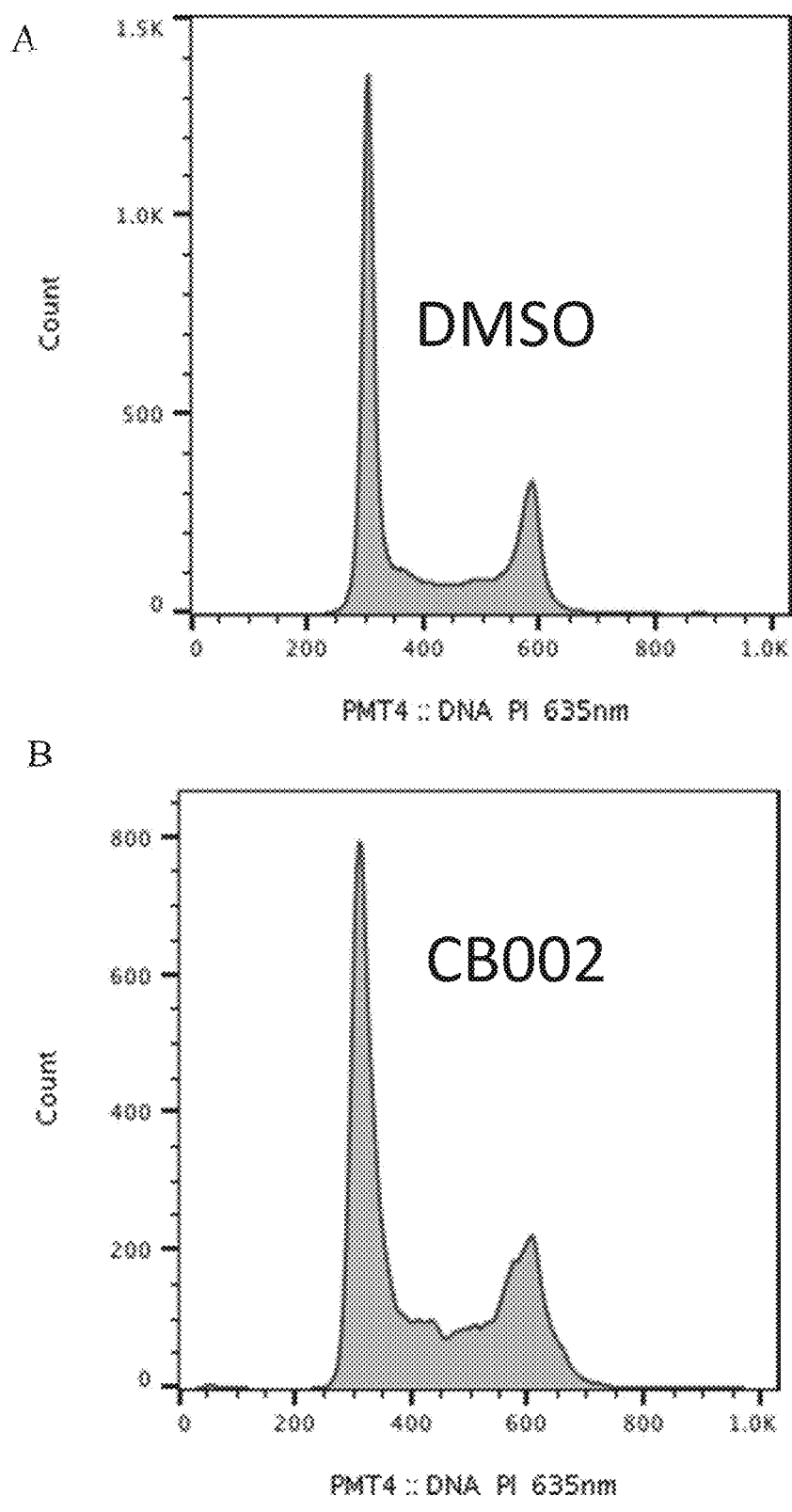
FIG. 22 (Panels A-F) shows propidium iodide stating cell cycle analysis of CB002, etoposide, and caffeine treatment.
Figure 22:
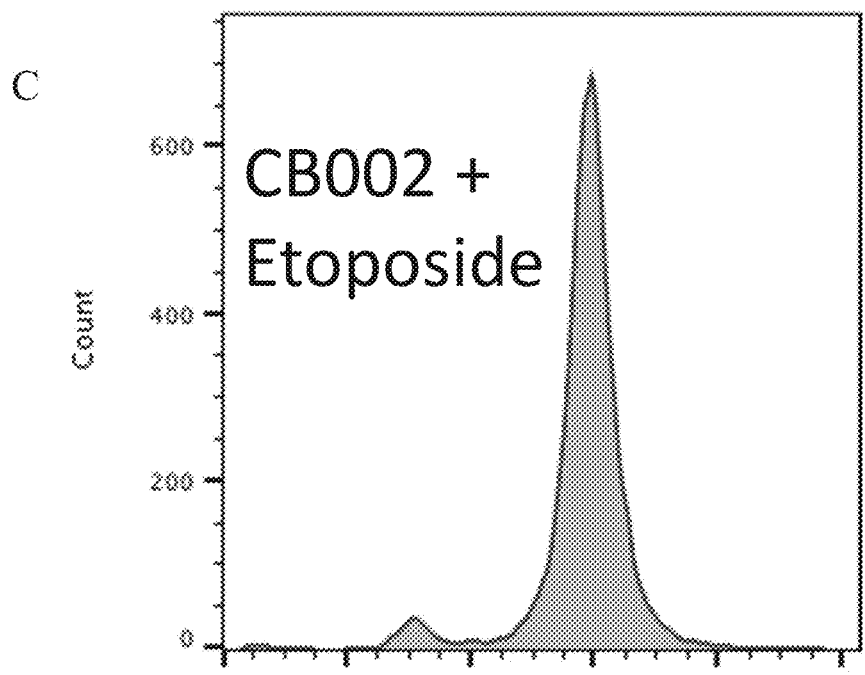
Figure 22:
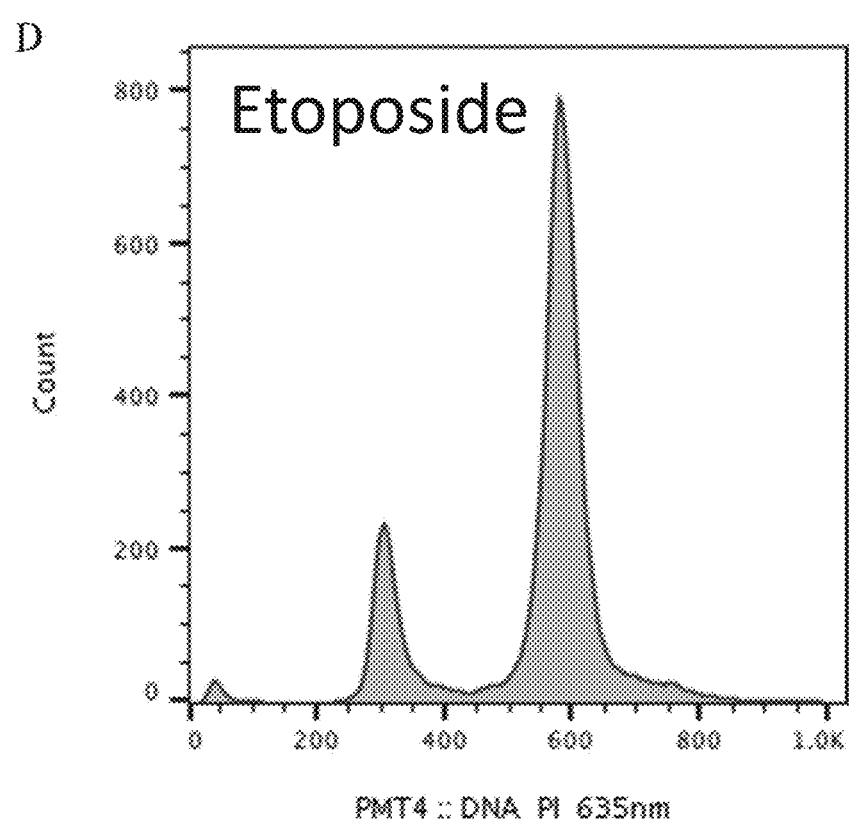
Figure 22:
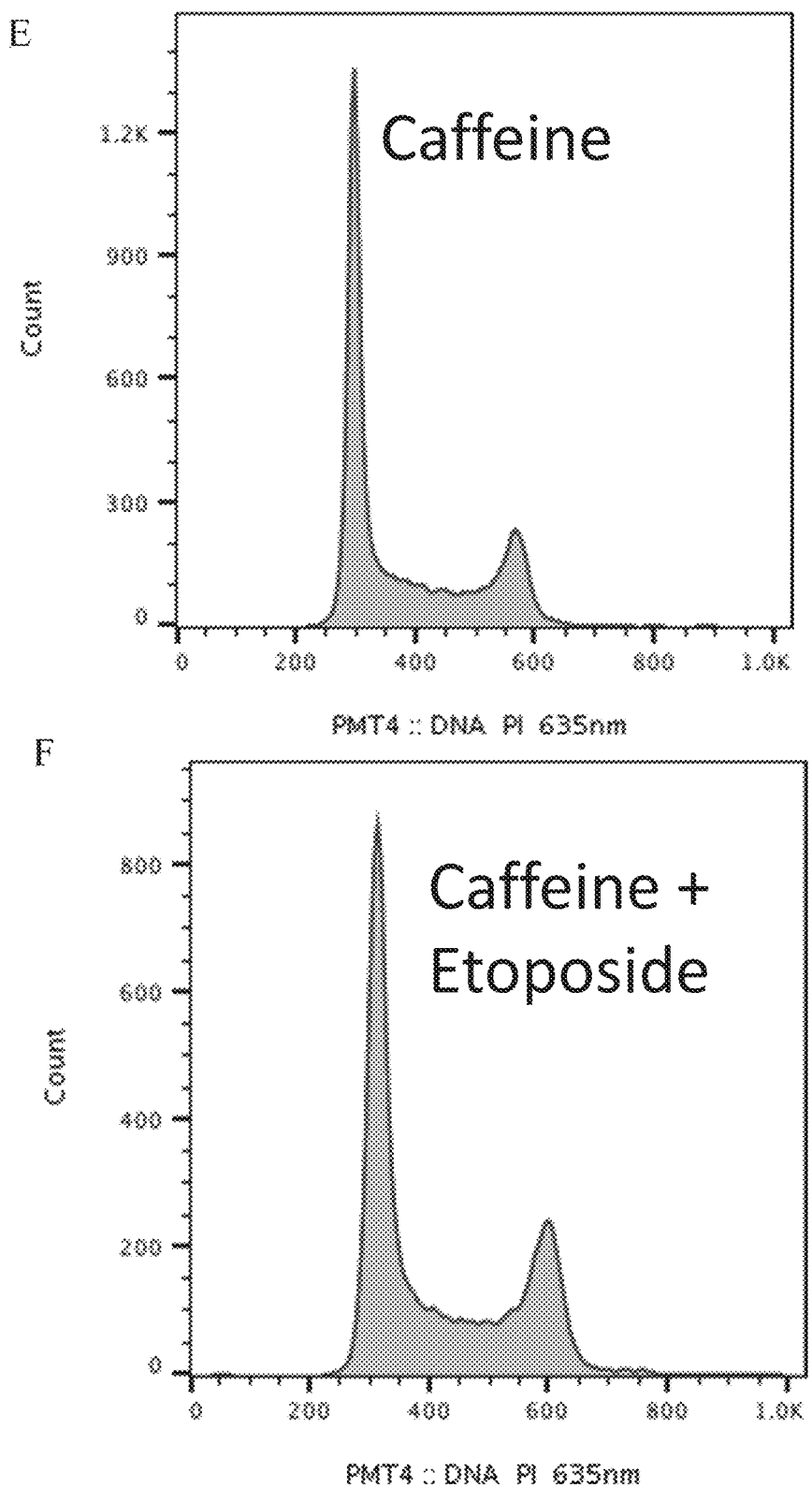

Example 20: CB002/Caffeine and Etoposide Combination have Different Cell Cycle Effects Referring to FIG. 22 (panels A-F), propidium iodide staining cell cycle analysis for 24 hour treatment with DMSO (panel A), CB002 (panel B), CB002 and etoposide (panel C), etoposide (panel D), caffeine (panel E), and caffeine and etoposixe (panel F). These results demonstrate that caffeine can deregulate the cell cycle G2 checkpoint. On the contrary to caffeine, CB002 does not appear to deregulate the G2 cell cycle checkpoint. The deregulation of the G2 checkpoint as a mechanism by caffeine prevents p53-expressing tumor cells that are treated with DNA damaging drugs, such as etoposide, from arresting to have time to repair, and thus sensitizes cancer cells to cell death. As such, the mechanism of CB002 does not involve deregulation of the G2 checkpoint.

Example 21: Noxa Induction is a Unique Property of CB002 and its Analogs

Figure 23:
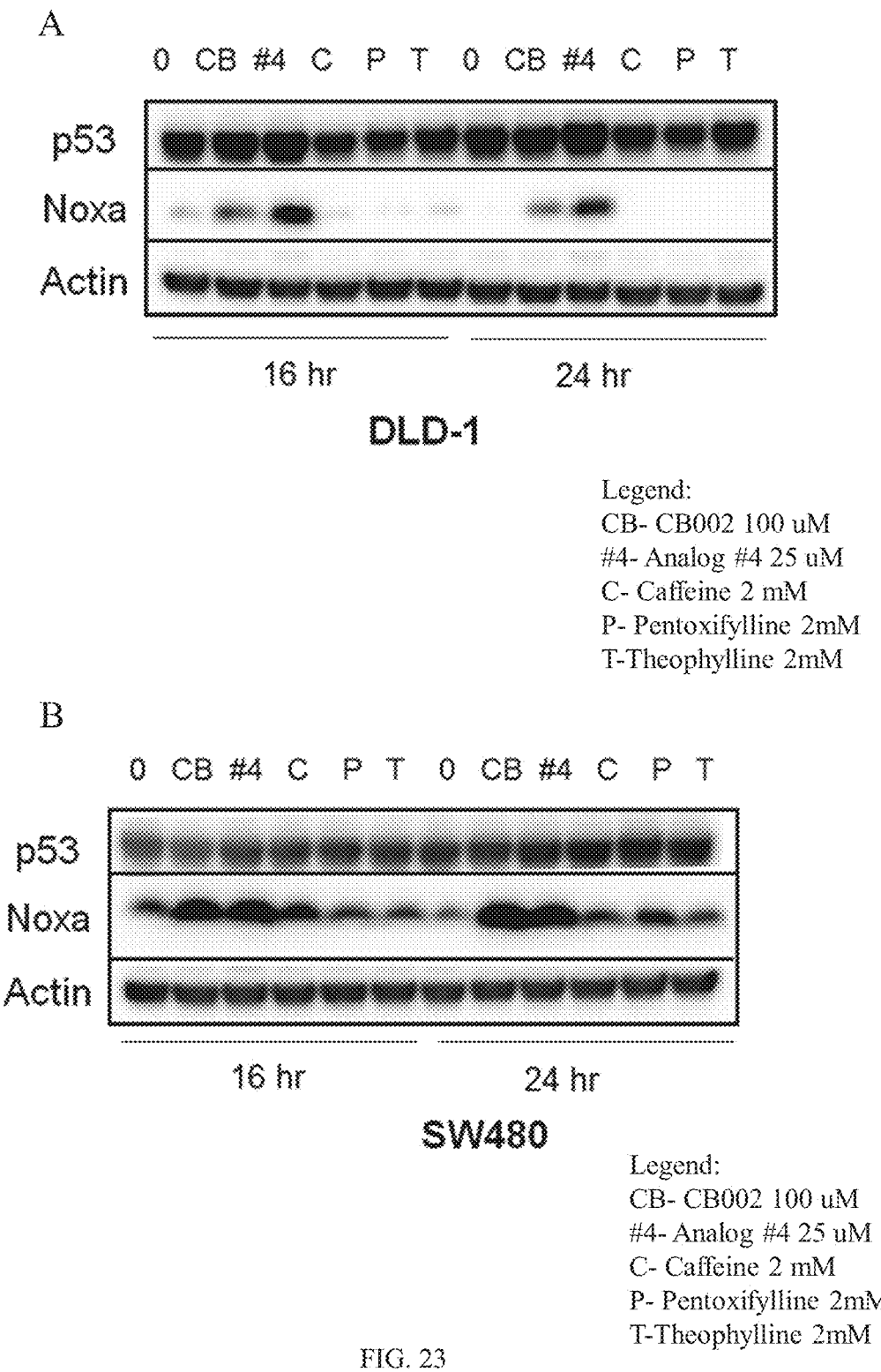
FIG. 23 (Panels A and B) shows Noxa induction in SW80 and DLD-1 cells treated with CB002, Analog 4, caffeine, pentoxifylline, or theophylline.

Referring to FIG. 23 (panels A and B), DLD-1 cells (panel A) and SW80 cells (panel B) were treated for 24 hours with the indicated agents. Noxa protein expression was analyzed by Western blot and showed that only the CB002 analogs were capable of inducing Noxa expression, whereas caffeine, pentoxifylline, and theophylline dis not induce Noxa expression.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A method of treating colon cancer in a mammal comprising administering to the mammal in need thereof a compound of Formula I:

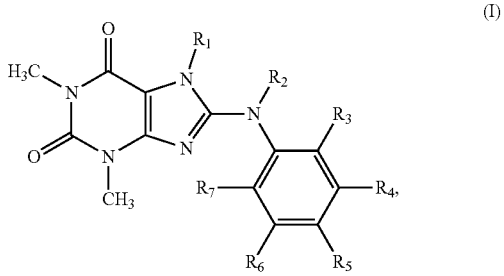

(I)

or a pharmaceutically acceptable salt thereof, wherein:
$R_1$ is hydrogen or a haloalkyl group;
each $R_2$, $R_3$, $R_4$, $R_5$, $R_6$, and $R_7$ is, independently, hydrogen, halogen, hydroxyl, alkyl, or alkoxy.

2. The method of claim 1, wherein $R_1$ is —$CF_3$, —$C_2F_5$, —$CHF_2$, —$CCl_3$, —$CHCl_2$, —$C_2Cl_5$, or —$CH_2CF_3$.

3. The method of claim 1, wherein the mmal is a human and is also administered radiation therapy, a chemotherapeutic agent, an immunotherapeutic agent, a lysosome inhibitor, or a calpain inhibitor, or any combination thereof.

4. The method of claim 1, wherein $R_1$ is —$CF_3$; and each of $R_2$, $R_3$, $R_4$, $R_5$, $R_6$, and $R_7$ is hydrogen.

* * * * *